US012686664B2

(12) United States Patent
Bazureau et al.

(10) Patent No.: US 12,686,664 B2
(45) Date of Patent: Jul. 21, 2026

(54) SOCE INHIBITORS AND THERAPEUTIC USES THEREOF

(71) Applicants: Institut National de la Santé et de la Recherche Médicale (INSERM), Paris (FR); Universite de Bretagne Occidentale, Brest (FR); Ecole Nationale Superieure de Chimie de Rennes, Rennes (FR); Institut National des Sciences Appliquees de Rennes, Rennes (FR); Universite Nangui Abrogoua, Abidjan (CI); Centre National de la Recherche Scientifique, Paris (FR); Universite de Rennes 1, Rennes (FR)

(72) Inventors: Jean Pierre Bazureau, La Chapelle des Fouegeretz (FR); Déliko Camille Dago, Rennes (FR); Lou Anna Voli, Rennes (FR); Olivier Mignen, Logonna Daoulas (FR); Christophe Brigaudeau, Lampaul Plouarzel (FR); Yves-Alain Berko, Abidjan (CI)

(73) Assignees: Institut National de la Sante et de la Recherche Medicale, Paris (FR); Universite de Bretagne Occidentale, Brest (FR); Ecole Nationale Superieure de Chimie de Rennes, Rennes (FR); Institut National des Sciences Appliquees de Rennes, Rennes (FR); Universite Nangui Abrogoua, Abidjan (FR); Centre National de la Recherche Scientifique, Paris (FR); Universite de Rennes, Rennes (FR)

( * ) Notice: Subject to any disclaimer, the term of this patent is extended or adjusted under 35 U.S.C. 154(b) by 674 days.

(21) Appl. No.: 17/925,738

(22) PCT Filed: May 19, 2021

(86) PCT No.: PCT/EP2021/063284

§ 371 (c)(1),
(2) Date: Nov. 16, 2022

(87) PCT Pub. No.: WO2021/233994

PCT Pub. Date: Nov. 25, 2021

(65) Prior Publication Data

US 2024/0116876 A1 Apr. 11, 2024

(30) Foreign Application Priority Data

May 19, 2020 (EP) .................................... 20175509

(51) Int. Cl.
*A61P 35/00* (2006.01)
*C07D 235/04* (2006.01)

(52) U.S. Cl.
CPC ............ *C07D 235/04* (2013.01); *A61P 35/00* (2018.01)

(58) Field of Classification Search
CPC .. C07D 235/04; C07D 231/12; C07D 231/56; C07D 235/10; C07D 249/08;
(Continued)

(56) References Cited

FOREIGN PATENT DOCUMENTS

WO 2010/048559 A2 4/2010
WO 2011/139765 A2 11/2011
(Continued)

OTHER PUBLICATIONS

Machin et al ,Beta1-Selective Adrenoceptor Antagonists. 3. 4-Azolyl-Linked Phenoxypropanolamines Journal of Medicinal Chemistry (1984), 27(4), 503-9 (Year: 1984).*
(Continued)

*Primary Examiner* — Taylor V Oh
(74) *Attorney, Agent, or Firm* — Morgan, Lewis & Bockius LLP

(57) ABSTRACT

The present invention provides SOCE inhibitors that are useful as therapeutic agents in a variety of applications. The present invention also relates to pharmaceutical compositions, products and kits comprising such SOCE inhibitors, and methods of using the SOCE inhibitors in the treatment of a variety of diseases.

8 Claims, 14 Drawing Sheets

(58) Field of Classification Search
CPC ..... C07D 405/12; C07D 235/06; A61P 35/00; A61P 1/18; A61P 7/02; A61P 9/00; A61P 11/00; A61P 11/06; A61P 17/06; A61P 19/00; A61P 19/02; A61P 21/00; A61P 25/28; A61P 29/00; A61P 37/00; A61P 37/08; A61K 45/06
USPC .......................................................... 514/396
See application file for complete search history.

(56) References Cited

FOREIGN PATENT DOCUMENTS

| | | | |
|---|---|---|---|
| WO | 2013/059677 | A1 | 4/2013 |
| WO | 2017/027400 | A1 | 2/2017 |

OTHER PUBLICATIONS

Guardia et al , N-Benzyl-4-((heteroaryl)methyl)benzamides: A New Classof Direct NADH-Dependent 2-trans Enoyl-Acyl Carrier Protein Reductase (InhA) Inhibitors with Antitubercular Activity, ChemMedChem 2016, 11, 687-701 (Year: 2016).*

Azimi et al., “Evaluation of known and novel inhibitors of Orai1-mediated store operated Ca2+ entry in MDA-MB-231 breast cancer cells using a Fluorescence Imaging Plate Reader assay,” Bioorganic & Medicinal Chemistry, 25:440-449 (2017).

International Search Report issued in corresponding International Patent Application No. PCT/EP2021/063284 dated Aug. 24, 2021.

Written Opinion issued in corresponding International Patent Application No. PCT/EP2021/063284 dated Aug. 24, 2021.

* cited by examiner

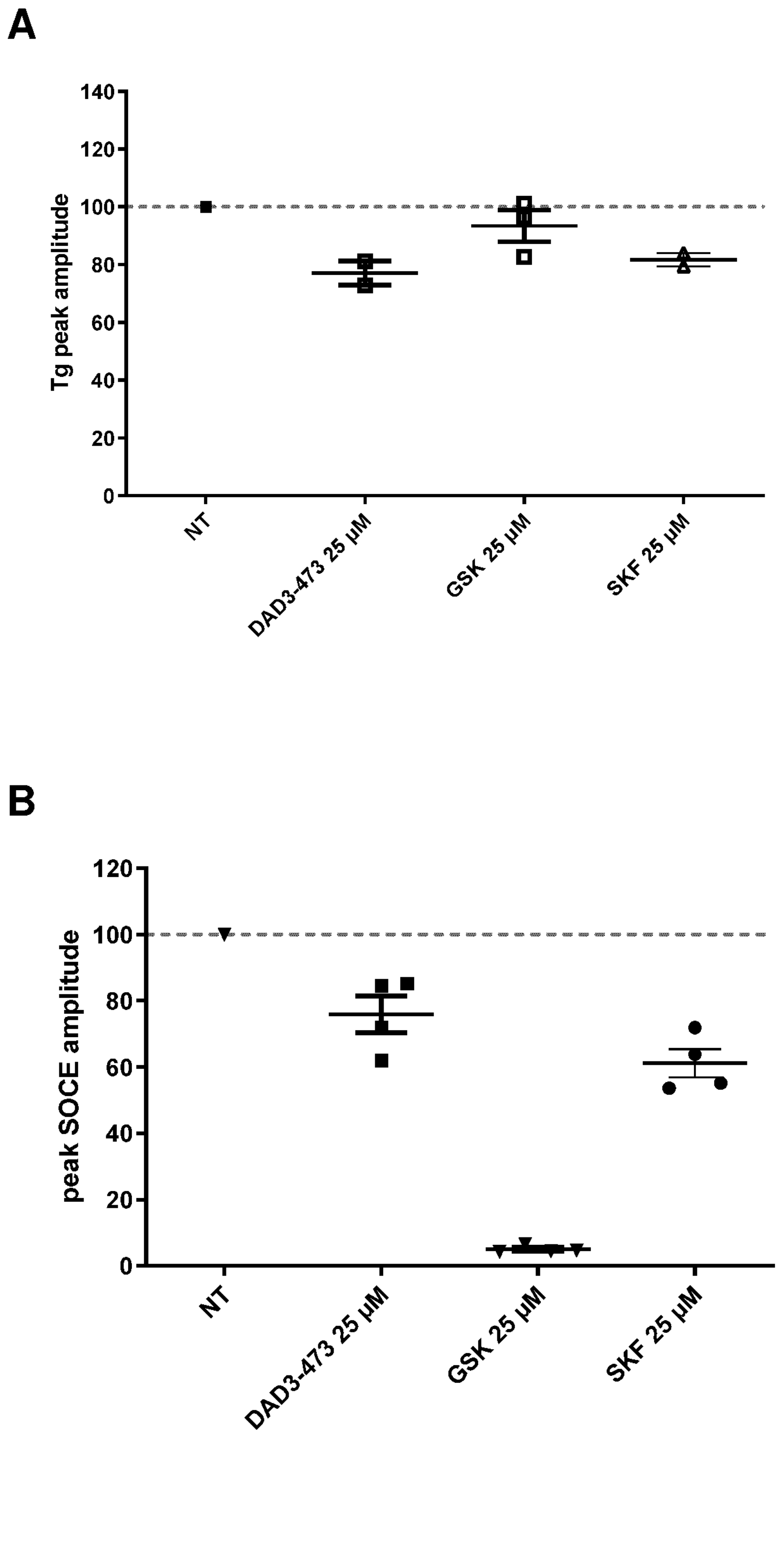
Figure 4 (A-B)

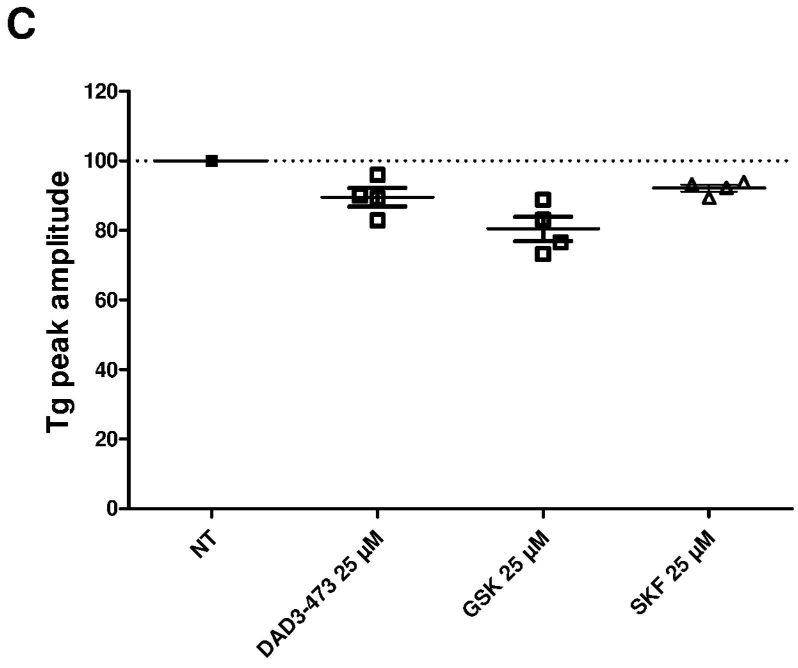
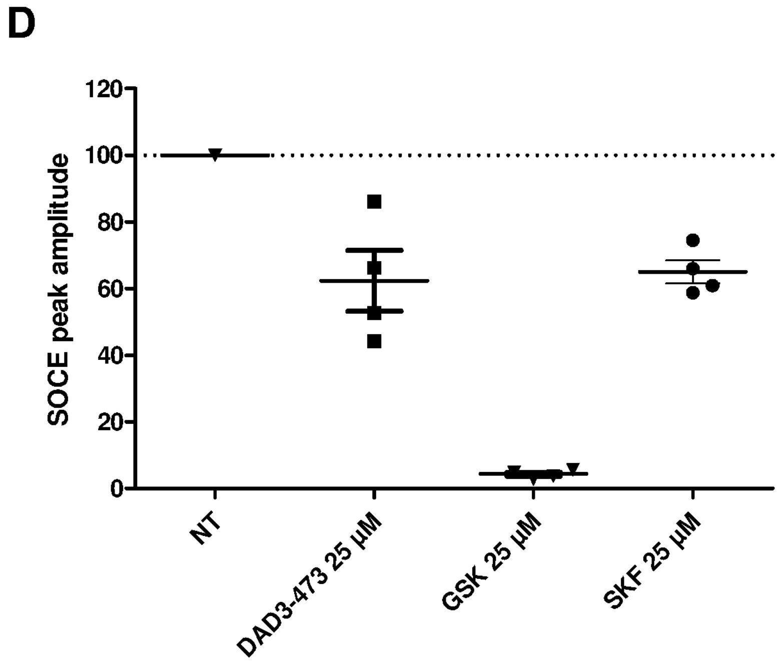
Figure 4 (C-D)

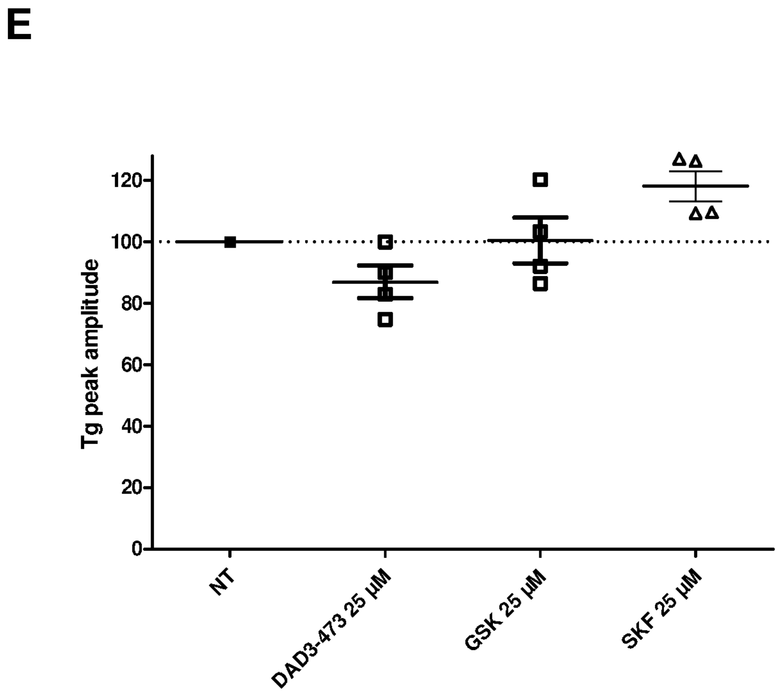
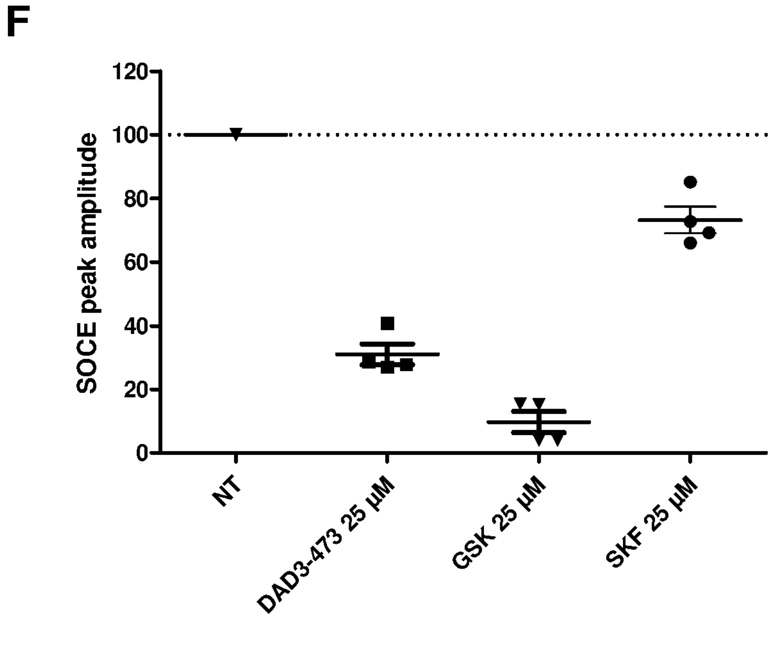
Figure 4 (E-F)

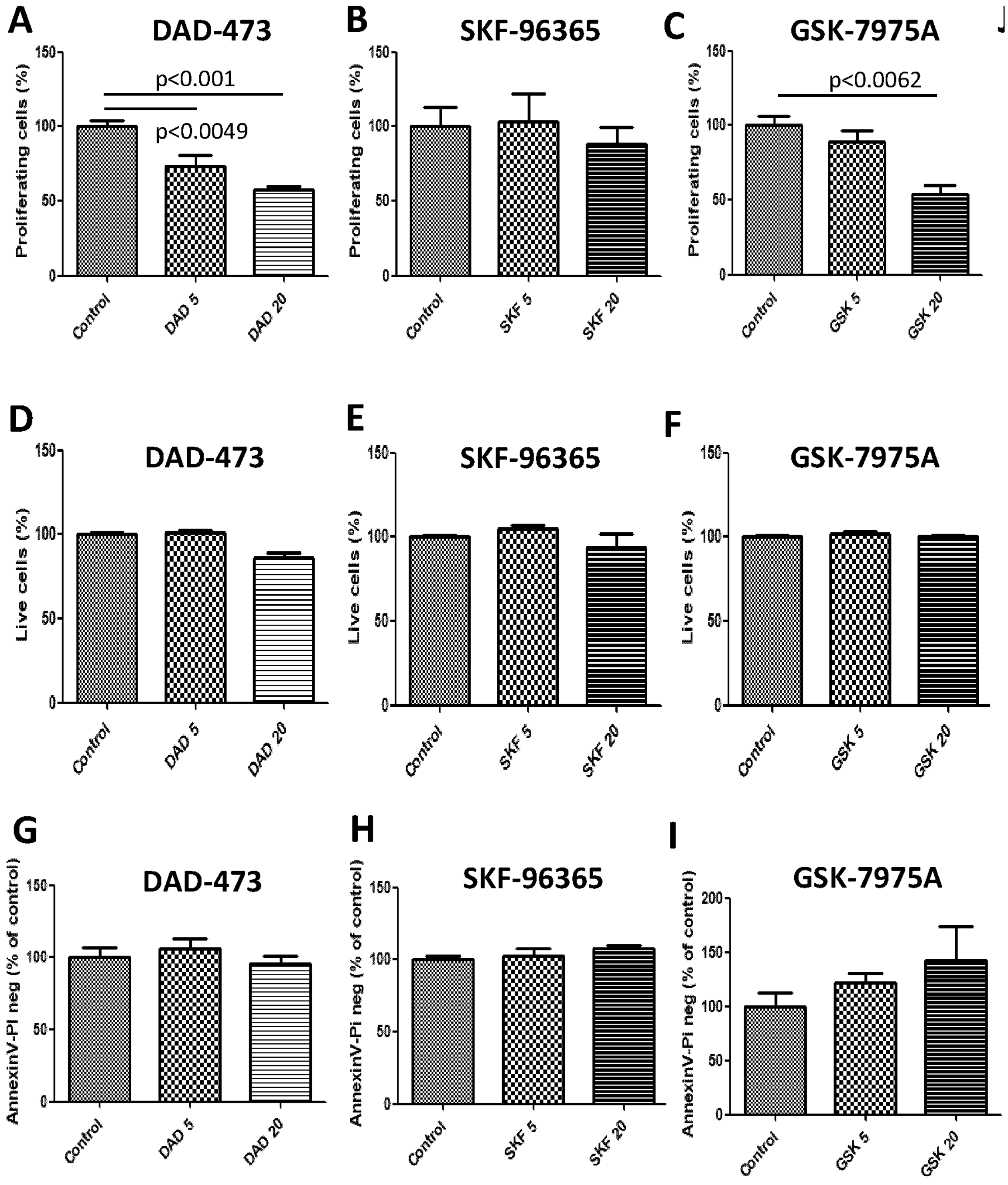
Figure 5 (A-I)

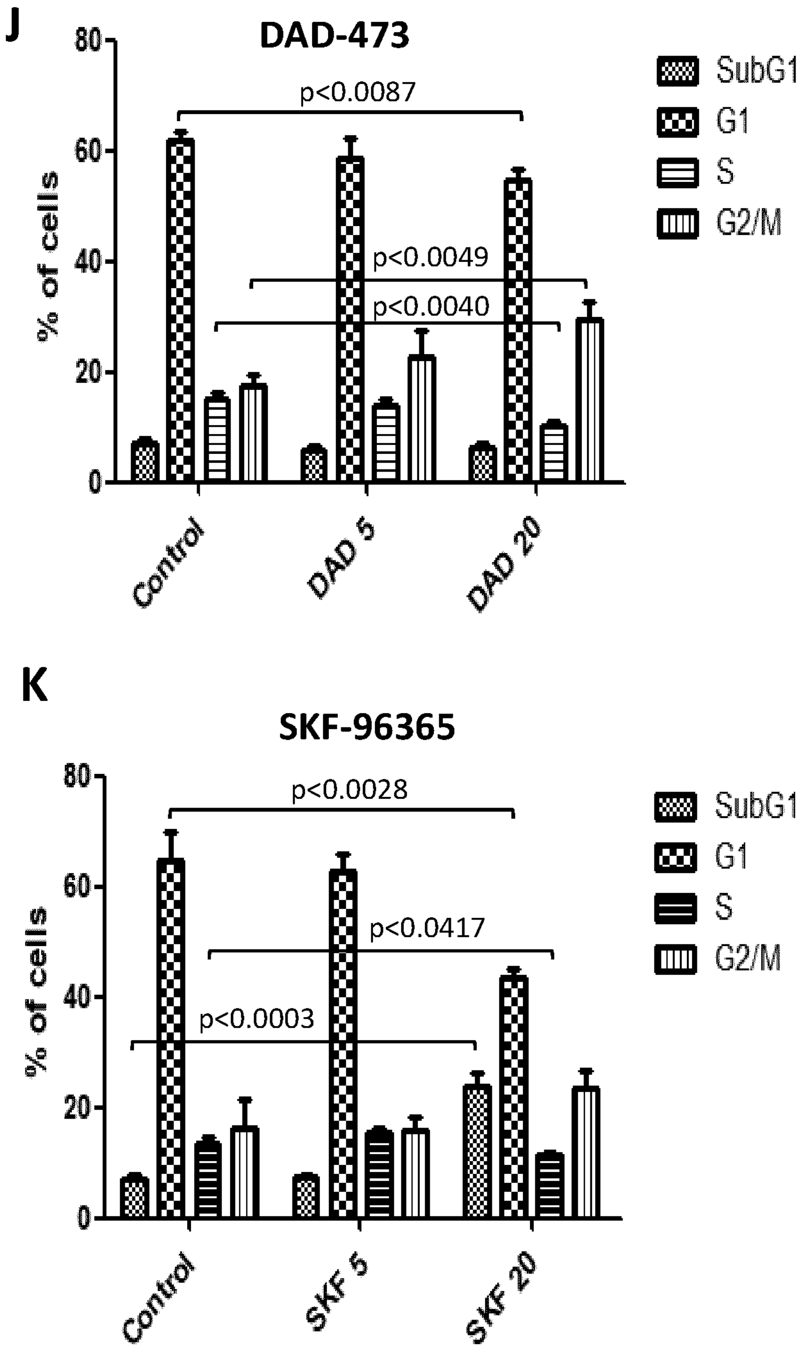
Figure 5(J-K)

A

B

C

SOCE INHIBITORS AND THERAPEUTIC USES THEREOF

RELATED APPLICATION

The present application claims priority to European Patent Application No. EP 20 175509.7 filed on Mai 19, 2020, which is incorporated herein by reference in its entirety.

BACKGROUND OF THE INVENTION

Store-operated calcium entry (SOCE) is a central mechanism in cellular calcium signaling and in maintaining cellular calcium balance. Its role is both to provide an increase in cytoplasmic $Ca^{2+}$ concentration and to refill intracellular $Ca^{2+}$ stores content. The elevation of intracellular $Ca^{2+}$ concentration due to SOCE is induced by the activation of a large variety of plasma membrane receptors and results from the depletion of intracellular $Ca^{2+}$ stores that subsequently triggers an extracellular $Ca^{2+}$ influx by the opening of plasma membrane $Ca^{2+}$ channels.

There are two main families of proteins involved in SOCE: The Stromal-Interacting Molecule family (STIM1 and STIM2) and ORAI, (Orai1, Orai2 and Orai3) family. TRPC (Transient Receptor Potential Canonical) channels from the large family of TRP channels have also been described as $Ca^{2+}$ permeable channels involved in SOCE. Depletion of endoplasmic reticulum (ER) $Ca^{2+}$ stores is sensed by STIM triggering translocation of this protein to ER-plasma membrane junctions, where STIM1 interacts with Orai/TRPC channels and subsequently allowing the extracellular $Ca^{2+}$ influx. In almost all cell types, SOCE plays an important role in many physiological processes. The opening of SOCE channels leads to the activation of many diverse downstream signaling pathways that regulate, among others, cytokine production, gene expression, as well as cell growth, proliferation, differentiation, migration and even apoptosis.

Deregulated SOCE has been implicated in a large number of human disorders, including immunodeficiency, autoimmunity, skeletal and vascular diseases, cardiorespiratory and neurodegenerative diseases, allergy, asthma, thrombosis, pancreatitis, inflammatory bowel disease, cardiovascular disorders, and cancer, thus placing SOC channels as very attractive targets for the treatment of these disorders.

The strongest rationale for SOCE inhibitors is for treating inflammatory and immunological disorders, which are typically chronic disorders (e.g., rheumatoid arthritis, psoriasis, multiple sclerosis and asthma) and cancers. As an example, SOCE plays an important role in cancer development and progression including tumor cell proliferation, migration, metastasis, invasion, and resistance to apoptosis. Dysregulation of $Ca^{2+}$ entry allows cancer cells to gain the adaptive advantages that result in tumor development, vascularization and metastasis throughout the organism. The role of SOCE, and more specifically of STIM1 and Orai1, was first reported in breast cancer migration and metastasis. It has now been reported in many other types of cancers, such as melanoma, esophageal carcinoma, pancreatic adenocarcinoma, prostate cancer, liver and renal cancers, hepatocellular carcinoma, stomach and colorectal cancers. There is undoubtedly an interest in developing molecules that modulate SOCE.

Since SOCE was described almost three decades ago, a number of molecules inhibiting this calcium entry process have been identified. The discovery of ORAI and STIM as major components of SOCE a decade and a half ago has greatly contributed to strengthen the interest in SOCE as a drug target and has led to the development of SOC channels inhibitors. Several classes of SOCE inhibitors (mainly ORAI inhibitors) that might hold promise for further drug development have been developed. However, only very few of them have reached clinical trials mainly because of the challenges associated with SOCE inhibitors, such as pharmacological, safety and toxicological profiles of the compounds.

A concern often stated is that the ubiquitous expression of SOCE components (Orai1 and STIM1) and the large spectrum of cellular functions of this $Ca^{2+}$ entry may result in many undesirable effects of SOCE inhibition in a variety of tissues. In vivo experimental data in mice models with global Orai1 or STIM1 deletions and clinical phenotype of SCID (Severe Combined ImmunoDeficiency) patients carrying loss-of-function or null mutations in ORAI1 or STIM1 confirm that full inhibition of SOCE may have deleterious effects. However, beyond the immunological dysfunction, the clinical phenotype of SCID patients seems to be limited to skeletal muscle, sweat glands, dental enamel and ocular smooth muscles. Heterozygous patients for any of the null or loss of functions mutations in ORA1 or STIM1 are moreover mostly asymptomatic. Altogether, it is suggested that partial reduction of SOCE may be well tolerated and these SOCE channel blockers may not adversely affect functions.

Thus, there is still a need in the art for SOCE modulators that sufficiently reduce the $Ca^{2+}$ influx but that have nevertheless significant functional biological effects without inducing adverse effects.

SUMMARY OF THE INVENTION

The present invention relates to new SOCE inhibitors, to their use as therapeutic agents, to pharmaceutical compositions thereof, and to methods of treatment using the SOCE inhibitors. More specifically, the present invention is based on the development of new small molecules that exhibit an inhibitory action on calcium signaling in different cell lines but without affecting other cellular processes such as cell survival, cell proliferation and cell migration.

Consequently, the present invention provides an aromatic azole compound having chemical formula (I)

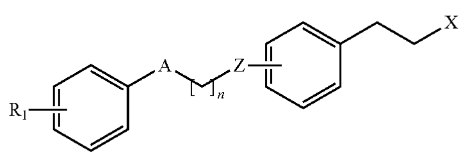

(I)

wherein:

- $R_1$ is one, two, three, four or five substituents, wherein each of the substituents is independently selected from H, OH, a halogen, $NH_2$, an alkoxy, an aryloxy, $OCH_2OR$, wherein R is an alkyl group, and O-THP, wherein THP is tetrahydropyranyl;
- A is $CH_2$ or O;
- if A is $CH_2$, then n=0, 1 or 2, and if A is O, then n=2 or 3;
- Z is O, NH, NHCO or CONH, NR, wherein R is an alkyl group, $NHSO_2$ or $SO_2NH$;

X is one of the following groups:

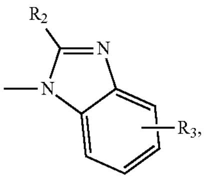
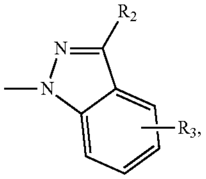
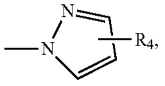
and
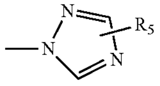

wherein:

$R_2$ is H, Cl, Br or $CF_3$;

$R_3$ is one, two, three or four substituents, wherein each of the substituents is independently selected from H, OH, $CF_3$, F, Cl, $NH_2$, COOH, and $CONH_2$;

$R_4$ is one, two or three substituents, wherein each of the substituents is independently selected from H, F, $CF_3$ and an alkyl group; and $R_5$ is one or two substituents, wherein each of the substituents is independently selected from H, F, and $CF_3$, or a pharmaceutically acceptable salt, solvate or hydrate thereof, or derivative thereof, or a prodrug thereof.

In the aromatic azole compound, the second phenyl ring may be ortho-, meta-, or para-substituted. In certain embodiments, in this aromatic azole compound, the second phenyl ring is meta- or para-substituted.

In certain embodiments, the aromatic azole compound has the chemical formula (I), wherein Z═O.

In certain embodiments, the aromatic azole compound, wherein Z═O, has the chemical formula (II):

(II)

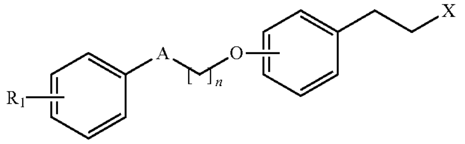

wherein $R_1$, A, n, and X are as described above.

In the aromatic azole compound of chemical formula (II), the second phenyl ring may be ortho-, meta-, or para-substituted. In certain embodiments, in this aromatic azole compound, the second phenyl ring is meta- or para-substituted.

In certain embodiments, the aromatic azole compound, wherein Z═O, has the chemical formula (III):

(III)

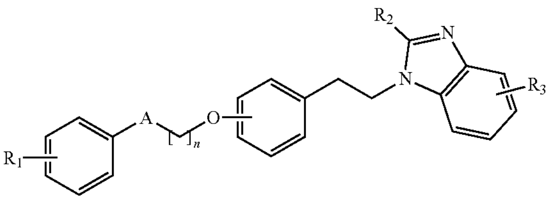

wherein $R_1$, A, n, $R_2$ and $R_3$ are as described above.

In the aromatic azole compound of chemical formula (III), the second phenyl ring may be ortho-, meta-, or para-substituted. In certain embodiments, in this aromatic azole compound, the second phenyl ring is meta- or para-substituted.

In certain embodiments, the aromatic azole compound has the chemical formula of one of the compounds presented in any one of Tables A, B and C, in particular Table A.

In certain embodiments, the aromatic azole compound is selected from the group consisting of

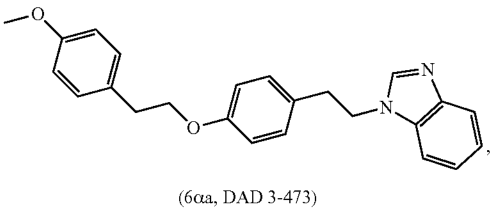

(6αa, DAD 3-473)

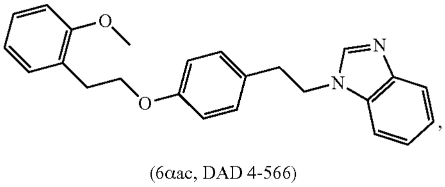
, and (6αac, DAD 4-566)

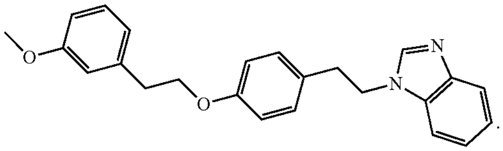

(6αad, DAD 4-567)

In other embodiments, the aromatic azole compound has the chemical formula (I), wherein Z═CONH.

In certain embodiments, the aromatic azole compound, wherein Z═CONH, has the chemical formula (II'):

(II')

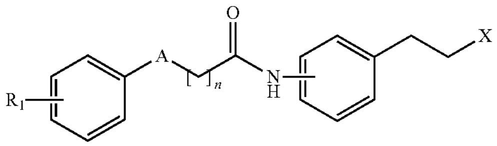

wherein $R_1$, A, n, and X are as described above.

In the aromatic azole compound of chemical formula (II'), the second phenyl ring may be ortho-, meta-, or para-substituted. In certain embodiments, in this aromatic azole compound, the second phenyl ring is meta- or para-substituted.

In certain embodiments, the aromatic azole compound, wherein Z═CONH, has the chemical formula (III')

(III')

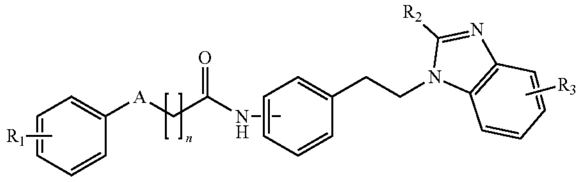

wherein $R_1$, A, n, $R_2$ and $R_3$ are as described above.

In the aromatic azole compound of chemical formula (III'), the second phenyl ring may be ortho-, meta-, or para-substituted. In certain embodiments, in this aromatic azole compound, the second phenyl ring is meta- or para-substituted.

In certain embodiments, the aromatic azole compound has the chemical formula of one of the amido analogues (7a, 7b, 7c and 7d) presented in Table 8.

In other embodiments, the aromatic azole compound has the chemical formula (I), wherein $Z{=}SO_2NH$.

In certain embodiments, the aromatic azole compound, wherein $Z{=}SO_2NH$, has the chemical formula (II")

(II")

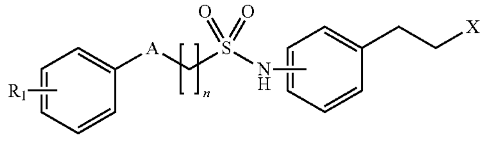

wherein $R_1$, A, n, and X are as described above.

In the aromatic azole compound of chemical formula (II"), the second phenyl ring may be ortho-, meta-, or para-substituted. In certain embodiments, in this aromatic azole compound, the second phenyl ring is meta- or para-substituted.

In certain embodiments, the aromatic azole compound, wherein $Z{=}SO_2NH$, has the chemical formula (III"), (III")

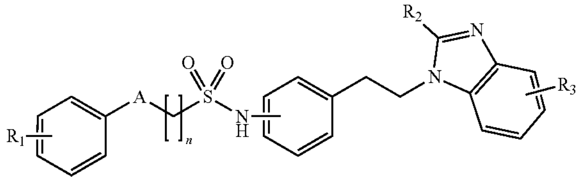

wherein $R_1$, A, n, $R_2$ and $R_3$ are as described above.

In the aromatic azole compound of chemical formula (III"), the second phenyl ring may be ortho-, meta-, or para-substituted. In certain embodiments, in this aromatic azole compound, the second phenyl ring is meta- or para-substituted.

In certain embodiments, the aromatic azole compound has the chemical formula of one of the sulfamido analogues (9a, 9b, 9c and 9d) presented in Table 9.

An aromatic azole compound as described herein, wherein said aromatic azole compound is a SOCE inhibitor.

The present invention also provides an aromatic azole compound as defined above for use as a therapeutic agent.

The present invention also provides an aromatic azole compound as defined above for use in the treatment of a disease associated with SOCE dysregulation or dysfunction.

In certain embodiments, the disease associated with SOCE dysregulation or dysfunction is selected from the group consisting of inflammatory diseases, immunodeficiency diseases, autoimmune diseases, allergies, cardiovascular diseases, cardiorespiratory diseases, vascular diseases, neurodegenerative diseases, skeletal muscle diseases, thromboses, and cancers.

In particular, the disease associated with SOCE dysregulation or dysfunction may be selected from the group consisting of inflammatory bowel diseases, pancreatitis, rheumatoid arthritis, multiple sclerosis, asthma, psoriasis, and cancers.

The present invention further provides a pharmaceutical composition comprising an effective amount of an aromatic azole compound as defined above, and a pharmaceutical acceptable carrier or excipient.

The present invention further provides the pharmaceutical composition for use as a therapeutic agent, in particular for the treatment of a disease associated with SOCE dysregulation or dysfunction, such as those defined herein.

The present invention also relates to the use of an aromatic azole compound as defined above for the manufacture of a medicament, in particular a medicament for the treatment of a disease associated with SOCE dysregulation or dysfunction, such as those defined herein.

The present invention further relates to a method of treatment of a disease associated with SOCE dysregulation or dysfunction in subject, the method comprising a step of administering to the subject a therapeutically effective amount of an aromatic azole compound as defined above. The disease associated with SOCE dysregulation or dysfunction is as defined herein.

These and other objects, advantages and features of the present invention will become apparent to those of ordinary skill in the art having read the following detailed description of the preferred embodiments.

BRIEF DESCRIPTION OF THE DRAWING

FIG. 4. SOCE Inhibition by 6αa, GSK-7975-A and SKF-93365 in a B Cell Line. SOCE inhibition of JOK B cells after ER $Ca^{2+}$ store depletion using thapsigargin, when the inventive compound 6αa (DAD 3-473), the SOCE inhibitor GSK-7975A, and the SOCE inhibitor SKF-93365 were added at different times before thiapsigargin addition. Each compound was incubated at a final concentration of 25 μM for 5 minutes (A), 15 minutes (B) or 30 minutes (C).

FIG. 5. Effects of 6αa, GSK-7975-A and SKF-93365 on B Cells (JOK) Growth, Apoptosis and Cell Cycle. JOK cells were treated for 24 hours with increasing concentration of the inventive compound 6αa (DAD 3-473) (A, D and G), the SOCE inhibitor GSK-7975A, (B, E and H), or the SOCE inhibitor SKF-93365 (C, F and I). Cell proliferation, cell death and apoptosis assays were performed using a CCK-8 cell proliferation assay, a LIVE/DEAD cell viability assay and an Annexin V/FITC-PI staining, respectively. Data represent the mean±S.E.M. (n=3). The values of control cells were considered as 100%. Cell cycle distribution results for cells treated with indicated concentration of 6αa (J), SKF-96365 (K) with treatment end points at 48 hours using PI staining followed by FACS analysis. Data represent the mean±S.E.M. (n=2). Statistical analyses were performed by using Unpaired t test, Two-tailed.

DETAILED DESCRIPTION OF CERTAIN PREFERRED EMBODIMENTS

Figure 1:
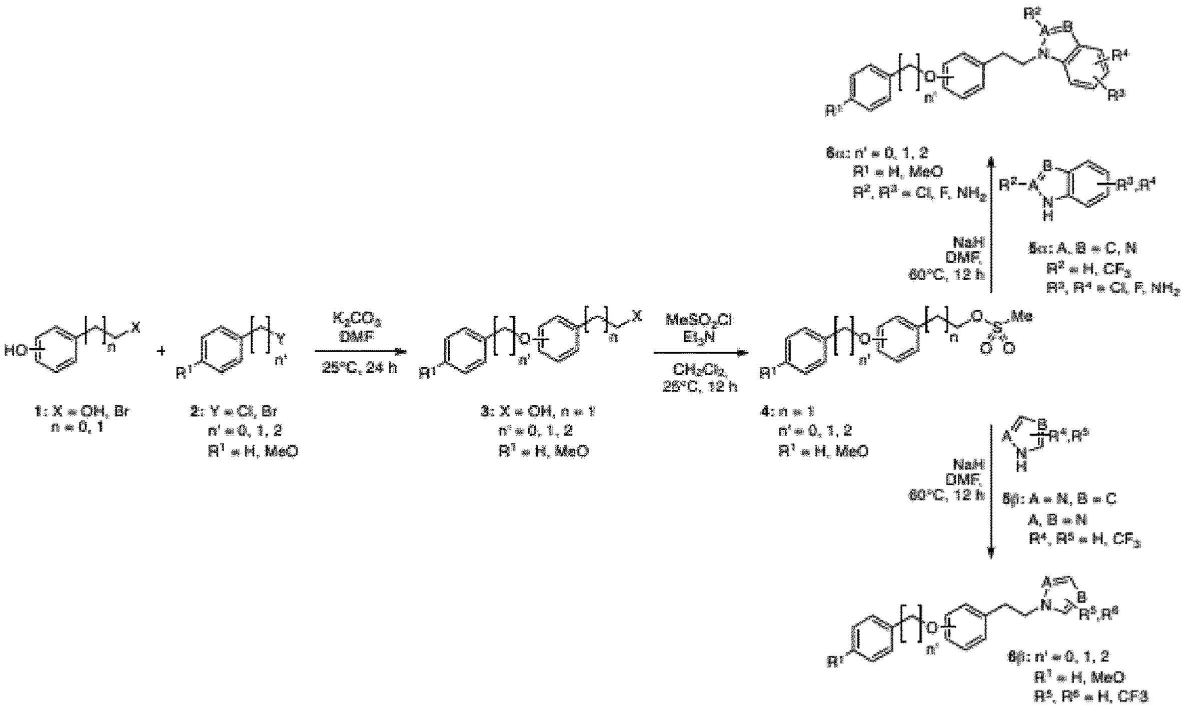
FIG. 1. Chemical Scheme used for the preparation of N-phenylalkyl azole SOCE inhibitors bearing benzimidazole, indazole, pyrazole and triazole platforms bearing no free hydroxyl functions on the terminal side chain.

As mentioned above, the present invention provides SOCE inhibitors, pharmaceutical compositions thereof, and uses thereof in a variety of therapeutic applications.

I—SOCE Inhibitors

The present invention provides several SOCE inhibitors. As used herein, the term "Store operated calcium entry" (or "SOCE") refers to the mechanism by which release of calcium ions from intracellular calcium stores induces a calcium influx across the plasma membrane. The terms "SOCE inhibitor" and "SOCE blocker" are used herein interchangeably; and refer to a compound, molecule or agent that reduces, blocks, inhibits, or eliminates $Ca^{2+}$ influx or $Ca^{2+}$ entry activated after calcium store depletion irrespective of the specific mechanism of action used to achieve this result. The terms "$Ca^{2+}$ influx" and "$Ca^{2+}$ entry" are used herein interchangeably and refer to entry of $Ca^{2+}$ from the extracellular medium into the cytoplasm of a cell. Movement of calcium into the cytoplasm from an intracellular organelle serving as a calcium storage site is also referred to as "calcium release" from the store.

A. SOCE Inhibitors

In particular, the present invention provides N-phenylalkyl azole derivatives which exhibit an inhibitory action on calcium signaling but do not significantly affect other cellular processes such as cell survival, cell proliferation and cell migration. The N-phenylalkyl azole derivatives comprise one of: benzimidazole, indazole, pyrazole and triazole groups and have or do not have a free hydroxyl function on the terminal chain. More specifically, the present invention provides aromatic azole compounds having chemical formula (I):

(I)

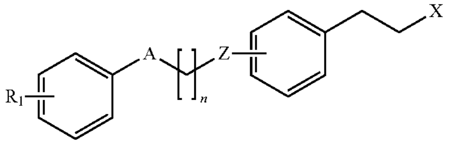

wherein:

$R_1$ is one, two, three, four or five substituents, wherein each of the substituents is independently selected from H, OH, a halogen (F, Cl, Br, or I), $NH_2$, an alkoxy, an aryloxy, $OCH_2OR$, wherein R is an alkyl group, and O-THP, wherein THP is tetrahydropyranyl;

A is $CH_2$ or O;

if A is $CH_2$, then n=0, 1 or 2, and if A is O, then n=2 or 3;

Z is O, NH, NHCO, NR, wherein R is an alkyl group, $NHSO_2$ or $SO_2NH$;

X is one of the following groups:

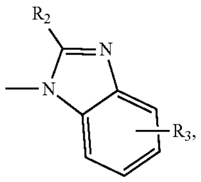

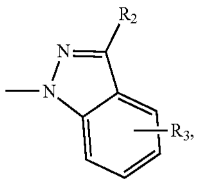

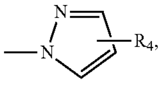

and

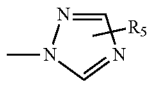

wherein:

$R_2$ is H, Cl, Br or $CF_3$;

$R_3$ is one, two, three or four substituents, wherein each of the substituents is independently selected from H, OH, $CF_3$, F, Cl, $NH_2$, COOH, and $CONH_2$;

$R_4$ is one, two or three substituents, wherein each of the substituents is independently selected from H, F, $CF_3$ and an alkyl group; and $R_5$ is one or two substituents, wherein each of the substituents is independently selected from H, F, and $CF_3$.

As used herein, the term "alkyl" refers to a monovalent straight or branched chain group saturated hydrocarbon of one to ten carbon atoms (C1-C10 alkyl), for example of one to eight carbon atoms (C1-C8 alkyl) or from one to five carbon atoms (C1-C5 alkyl). Representative saturated straight chain alkyls include methyl, methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethyl-butyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethyl-hexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group may be optionally substituted, as defined below.

As used herein, the term "optionally substituted" indicates that the particular group being described can have one or more hydrogen substituents replaced by a non-hydrogen substituent. In the context of the present invention, an alkyl group is substituted to the extent to that such substitution makes sense chemically. Examples of substituents include, but are not limited to, nitro ($—NO_2$), sulfo ($—SO_4—$), cyano (—CN), halogen (F, Br, Cl, I), amine ($—NR''_2$, where each R" is independently H or an alkyl), hydroxyl (—OH), aldehyde (—CHO), ketone ($R_i—CO—R_{ii}$), ester ($—R_i—COO—R_{ii}$ or $—R_i—OCO—R_{ii}$), amide ($—R_i—CO—NR_{ii}R_{iii}$ or $R_i—NR_{iii}—CO—R_i$), carboxylic acid (—COOH or —COOM, where M is a suitable cation, such as sodium or potassium) or sulfonic acid ($—SO_3H$ or $—Ri\text{-}SO_3H$) groups.

As used herein, the term "alkoxy" refers to a straight or branched —OR group, wherein R is an alkyl group. Preferred alkoxy groups include methoxy, ethoxy, n-propoxy, isopropoxy, t-butoxy, and the like.

As used herein, the term "aryloxy" refers to straight or branched —OAr group, wherein Ar is an aryl group. The term 'aryl group" refers an aromatic radical such as phenyl, biphenyl or naphthyl, wherein said phenyl, biphenyl or naphthyl group may be optionally substituted by one, two or three groups independently selected from nitro, sulfo, cyano, halogen, amine, hydroxyl, aldehyde, ketone, ester, amide, carboxylic acid, or sulfonic acid groups (as described above). In certain embodiments, the preferred aryloxy group is phenoxy.

The second phenyl ring of the aromatic azole compound of formula (I) may be ortho-, meta- or para-substituted. In certain embodiments, the second phenyl ring of the aromatic azole compound of formula (I) is meta- or para-substituted.

In other embodiments, the aromatic azole compound of chemical formula (I) is such that Z═O, i.e., has the chemical formula (II):

(II)

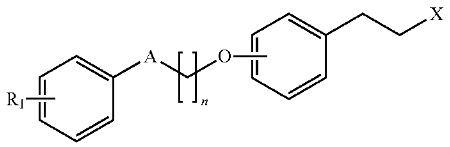

wherein $R_1$, A, n, and X are as described above.

The second phenyl ring of the aromatic azole compound of formula (II) may be ortho-, meta- or para-substituted. In certain embodiments, the second phenyl ring of the aromatic azole compound of formula (II) is meta- or para-substituted.

In certain embodiments, the aromatic azole compound has the chemical formula (III):

(III)

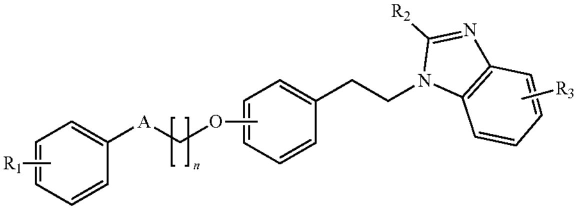

wherein $R_1$, A, n, $R_2$ and $R_3$ are as described above.

The second phenyl ring of the aromatic azole compound of formula (III) may be ortho-, meta- or para-substituted. In certain embodiments, the second phenyl ring of the aromatic azole compound of formula (III) is meta- or para-substituted.

In certain embodiments, the aromatic azole compound is selected from the group consisting of compounds presented in Table A, Table B and Table C.

TABLE A

| Chemical structures of 1-[4-(phenylalkoxy)phenylethyl]-1H-benzo[d]imidazole 6α and substituted 1-[4-(phenylalkoxy)-phenylethyl]-1H-indazoles 6αf, 6α(x,y). | |
|---|---|
| 6αc<br>DAD 4-546 | 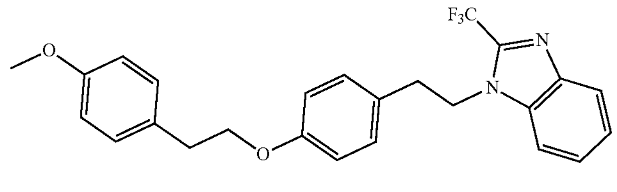 [SMILES: COc1ccc(CCOc2ccc(CCn3c(C(F)(F)F)nc4ccccc43)cc2)cc1] |
| 6αt<br>VAL 1-76 | 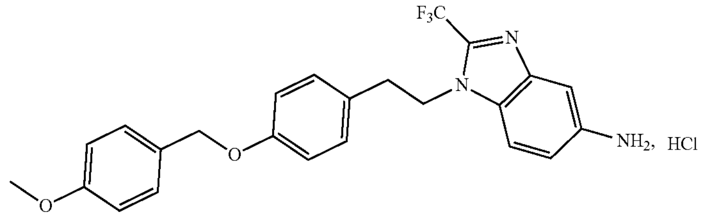 [SMILES: COc1ccc(COc2ccc(CCn3c(C(F)(F)F)nc4cc(N)ccc43)cc2)cc1 ; Cl] |
| 6αm<br>VAL 1-77 | 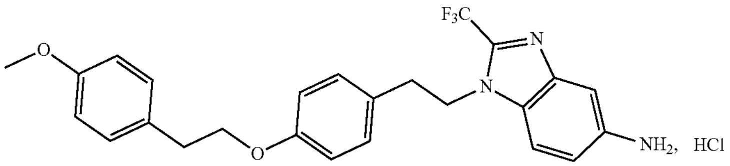 [SMILES: COc1ccc(CCOc2ccc(CCn3c(C(F)(F)F)nc4cc(N)ccc43)cc2)cc1 ; Cl] |
| 6αu<br>VAL 1-75 | 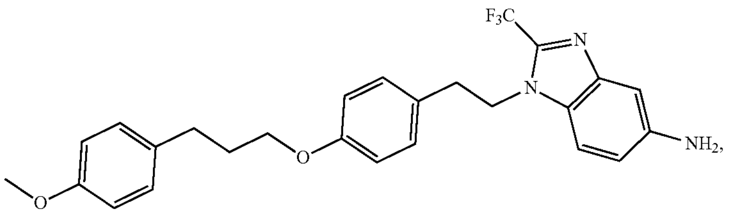 [SMILES: COc1ccc(CCCOc2ccc(CCn3c(C(F)(F)F)nc4cc(N)ccc43)cc2)cc1] |
| 6αv<br>VAL 1-64 | 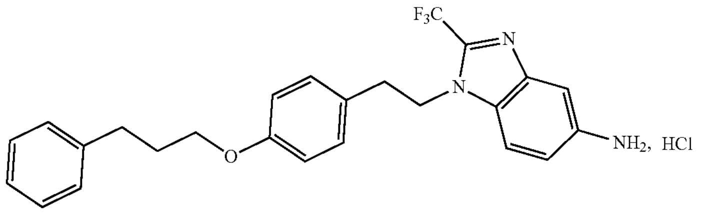 [SMILES: Nc1ccc2c(c1)nc(C(F)(F)F)n2CCc1ccc(OCCCc2ccccc2)cc1 ; Cl] |
| 6αe<br>DAD 4-548 | 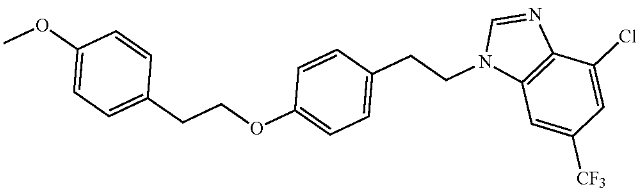 [SMILES: COc1ccc(CCOc2ccc(CCn3cnc4c(Cl)cc(C(F)(F)F)cc43)cc2)cc1] |
| 6αd<br>DAD 4-547 | 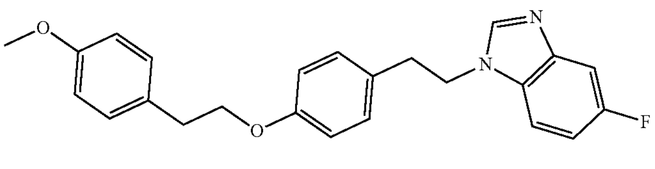 [SMILES: COc1ccc(CCOc2ccc(CCn3cnc4cc(F)ccc43)cc2)cc1] |

TABLE A-continued
Chemical structures of 1-[4-(phenylalkoxy)phenylethyl]-1H-benzo [d]imidazole 6α and substituted 1-[4-(phenylalkoxy)-phenylethyl]-1H-indazoles 6αf, 6α(x,y).
| | |
|---|---|
| 6αo<br>DAD 4-551 | 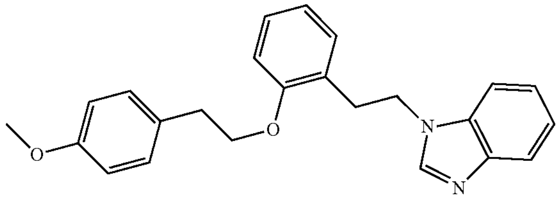 [SMILES: COc1ccc(CCOc2ccccc2CCn2cnc3ccccc32)cc1] |
| 6αp<br>DAD 4-552 | 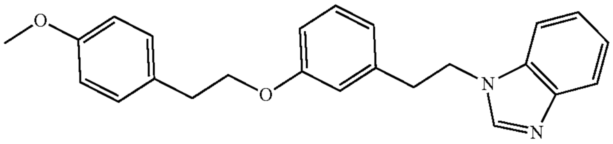 [SMILES: COc1ccc(CCOc2cccc(CCn3cnc4ccccc43)c2)cc1] |
| 6αab<br>DAD 4-553 | 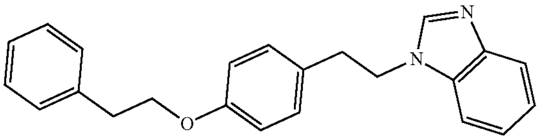 [SMILES: c1ccc(CCOc2ccc(CCn3cnc4ccccc43)cc2)cc1] |
| 6αac<br>DAD 4-566 | 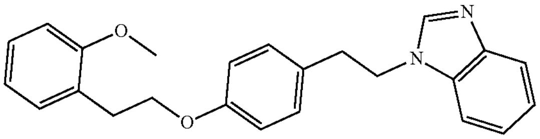 [SMILES: COc1ccccc1CCOc1ccc(CCn2cnc3ccccc32)cc1] |
| 6αad<br>DAD 4-567 | 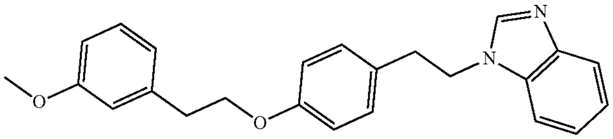 [SMILES: COc1cccc(CCOc2ccc(CCn3cnc4ccccc43)cc2)c1] |
| 6αd<br>DAD 4-568 | 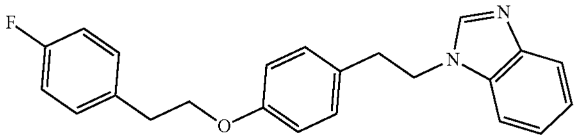 [SMILES: Fc1ccc(CCOc2ccc(CCn3cnc4ccccc43)cc2)cc1] |
| 6αs<br>DAD 4-570 | 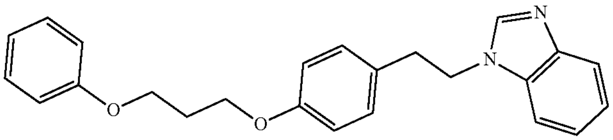 [SMILES: c1ccc(OCCCOc2ccc(CCn3cnc4ccccc43)cc2)cc1] |
| 6αae<br>DAD 4-569 | 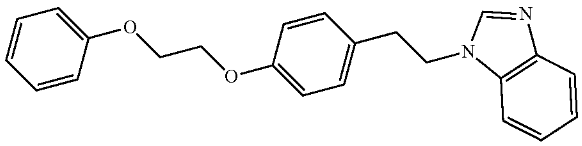 [SMILES: c1ccc(OCCOc2ccc(CCn3cnc4ccccc43)cc2)cc1] |
| 6αa<br>DAD 3-473 | 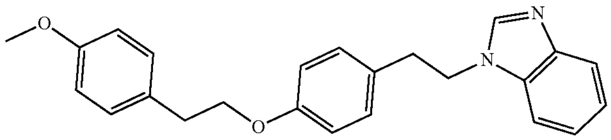 [SMILES: COc1ccc(CCOc2ccc(CCn3cnc4ccccc43)cc2)cc1] |

TABLE A-continued
| Chemical structures of 1-[4-(phenylalkoxy)phenylethyl]-1H-benzo [d]imidazole 6α and substituted 1-[4-(phenylalkoxy)-phenylethyl]-1H-indazoles 6αf, 6α(x,y). | |
|---|---|
| 6αm DAD 3-475 | 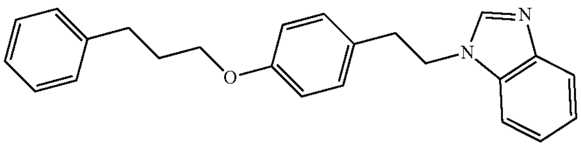 [SMILES: c1ccc(CCCOc2ccc(CCn3cnc4ccccc43)cc2)cc1] |
| 6αn DAD 3-474 | 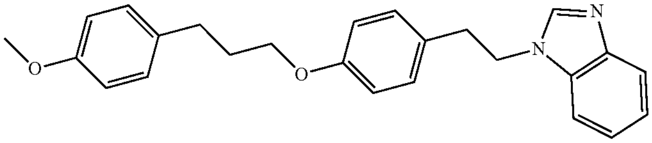 [SMILES: COc1ccc(CCCOc2ccc(CCn3cnc4ccccc43)cc2)cc1] |
| 6αz DAD 4-472 | 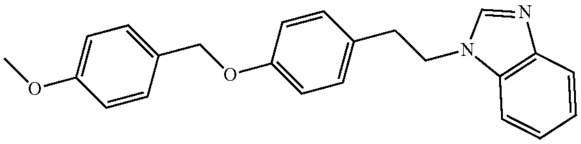 [SMILES: COc1ccc(COc2ccc(CCn3cnc4ccccc43)cc2)cc1] |
| 6αb DAD 4-573 | 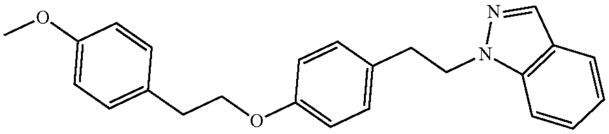 [SMILES: COc1ccc(CCOc2ccc(CCn3ncc4ccccc43)cc2)cc1] |
| 6αaa DAD 4-574 | 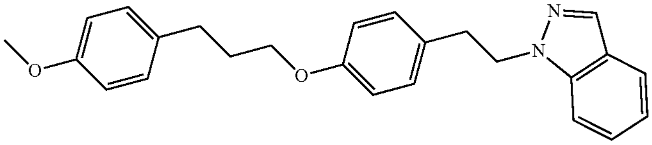 [SMILES: COc1ccc(CCCOc2ccc(CCn3ncc4ccccc43)cc2)cc1] |
| 6αab DAD 4-575 | 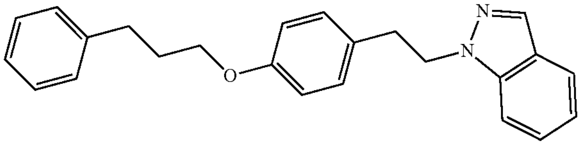 [SMILES: c1ccc(CCCOc2ccc(CCn3ncc4ccccc43)cc2)cc1] |
TABLE B
| Chemical structures of 1-[4-(phenylalkoxy)phenylethyl]-1H-pyrazole 6βc and substituted 1-[4-(phenylalkoxy)phenylethyl]-1H-1,2,4-triazoles 6β(j-l). | |
|---|---|
| 6βu DAD 2.334 | 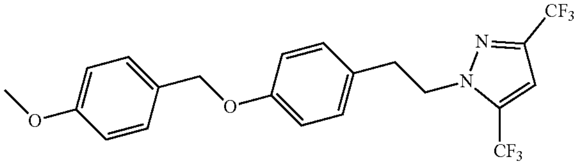 [SMILES: COc1ccc(COc2ccc(CCn3nc(C(F)(F)F)cc3C(F)(F)F)cc2)cc1] |
| 6βq DAD 2.333 | 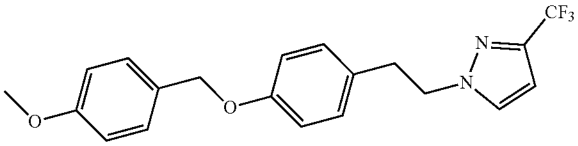 [SMILES: COc1ccc(COc2ccc(CCn3ccc(C(F)(F)F)n3)cc2)cc1] |

TABLE B-continued
| Chemical structures of 1-[4-(phenylalkoxy)phenylethyl]-1H-pyrazole 6βc and substituted 1-[4-(phenylalkoxy)phenylethyl]-1H-1,2,4-triazoles 6β(j-l). | |
|---|---|
| 6ßm<br>DAD 2.306 | 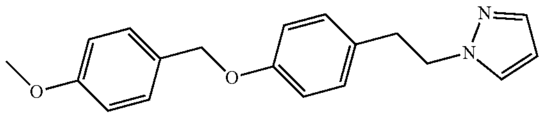 [SMILES: COc1ccc(COc2ccc(CCn3cccn3)cc2)cc1] |
| 6βg<br>DAD 3.472 | 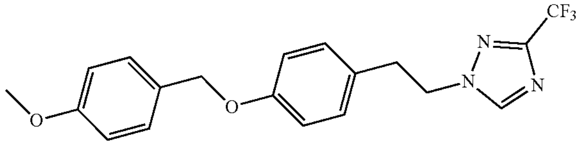 [SMILES: COc1ccc(COc2ccc(CCn3cnc(C(F)(F)F)n3)cc2)cc1] |
| 6βd<br>DAD 3.468 | 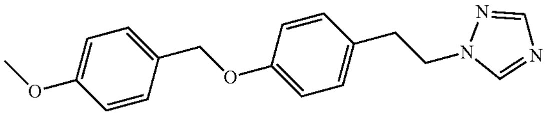 [SMILES: COc1ccc(COc2ccc(CCn3cncn3)cc2)cc1] |
| 6βv<br>DAD 2.266 | 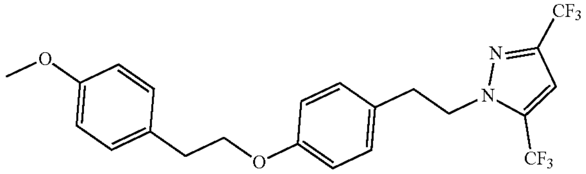 [SMILES: COc1ccc(CCOc2ccc(CCn3nc(C(F)(F)F)cc3C(F)(F)F)cc2)cc1] |
| 6βr<br>DAD 3.362 | 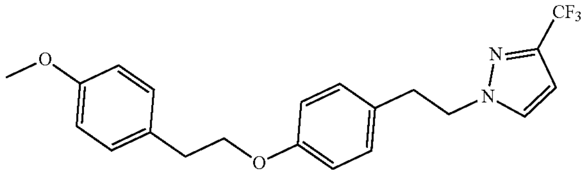 [SMILES: COc1ccc(CCOc2ccc(CCn3ccc(C(F)(F)F)n3)cc2)cc1] |
| 6βn<br>DAD 2.307 | 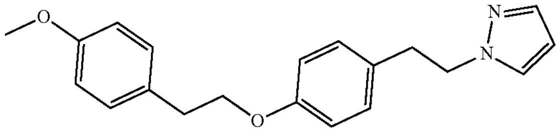 [SMILES: COc1ccc(CCOc2ccc(CCn3cccn3)cc2)cc1] |
| 6βr<br>DAD 3.473 | 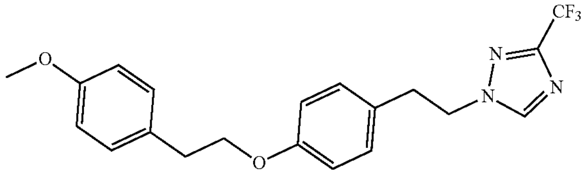 [SMILES: COc1ccc(CCOc2ccc(CCn3cnc(C(F)(F)F)n3)cc2)cc1] |
| 6βd<br>DAD 3.469 | 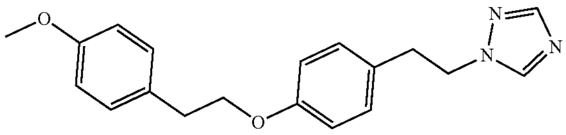 [SMILES: COc1ccc(CCOc2ccc(CCn3cncn3)cc2)cc1] |
| 6βw<br>DAD 2.335 | 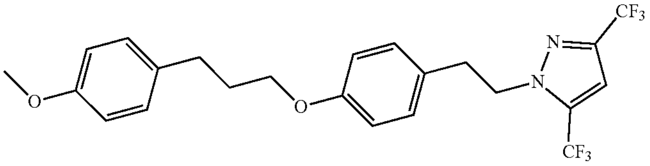 [SMILES: COc1ccc(CCCOc2ccc(CCn3nc(C(F)(F)F)cc3C(F)(F)F)cc2)cc1] |
| 6βs<br>DAD 2.276 | 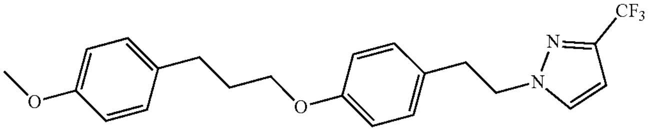 [SMILES: COc1ccc(CCCOc2ccc(CCn3ccc(C(F)(F)F)n3)cc2)cc1] |

TABLE B-continued
| Chemical structures of 1-[4-(phenylalkoxy)phenylethyl]-1H-pyrazole 6βc and substituted 1-[4-(phenylalkoxy)phenylethyl]-1H-1,2,4-triazoles 6β(j-l). | |
|---|---|
| 6βp<br>DAD 2.308 | 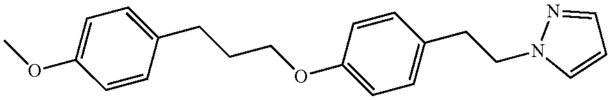 [SMILES: COc1ccc(CCCOc2ccc(CCn3cccn3)cc2)cc1] |
| 6βs<br>DAD 3.474 | 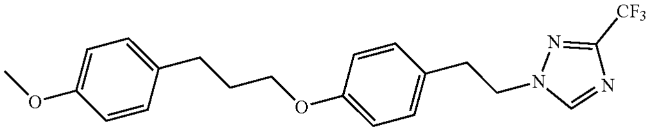 |
| 6βe<br>DAD 3.470 | 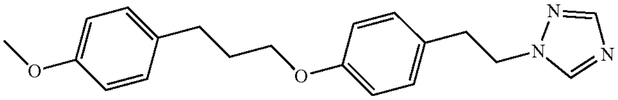 [SMILES: COc1ccc(CCCOc2ccc(CCn3cncn3)cc2)cc1] |
| 6βf<br>DAD 2.300 | 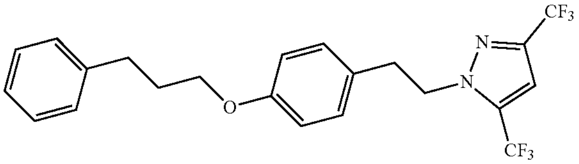 [SMILES: FC(F)(F)c1cc(C(F)(F)F)n(CCc2ccc(OCCCc3ccccc3)cc2)n1] |
| 6βt<br>DAD 3.363 | 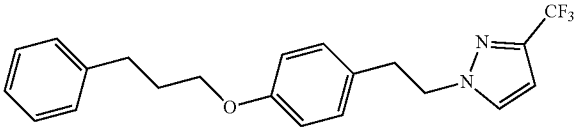 [SMILES: FC(F)(F)c1ccn(CCc2ccc(OCCCc3ccccc3)cc2)n1] |
| 6βp<br>DAD 2.299 | 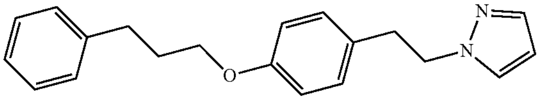 [SMILES: c1ccc(CCCOc2ccc(CCn3cccn3)cc2)cc1] |
| 6βi<br>DAD 3.475 | 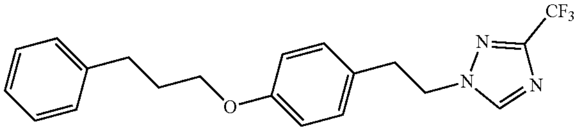 |
| 6βf<br>DAD 3.471 | 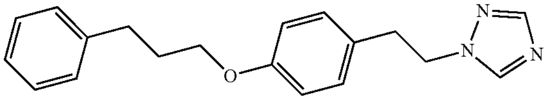 [SMILES: c1ccc(CCCOc2ccc(CCn3cncn3)cc2)cc1] |
| 6βy<br>DAD 3.531 | 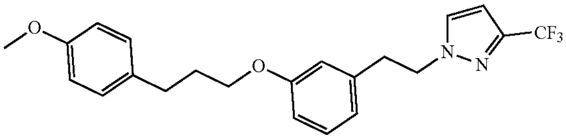 [SMILES: COc1ccc(CCCOc2cccc(CCn3ccc(C(F)(F)F)n3)c2)cc1] |
| 6βz<br>DAD 3.536 | 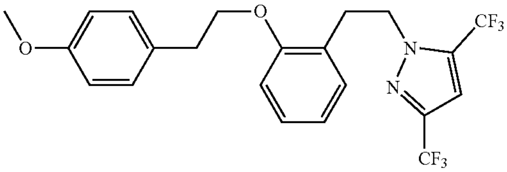 [SMILES: COc1ccc(CCOc2ccccc2CCn2nc(C(F)(F)F)cc2C(F)(F)F)cc1] |

TABLE B-continued

| Chemical structures of 1-[4-(phenylalkoxy)phenylethyl]-1H-pyrazole 6βc and substituted 1-[4-(phenylalkoxy)phenylethyl]-1H-1,2,4-triazoles 6β(j-l). | |
|---|---|
| 6βaa<br>DAD 3.535 | 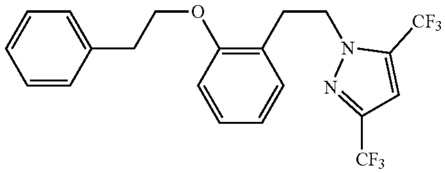 [SMILES: FC(F)(F)c1cc(C(F)(F)F)n(CCc2ccccc2OCCc2ccccc2)n1] |

TABLE C

| Chemical structures of 1-(4-hydroxyphenylalkyl)-1H-azoles 12α. | |
|---|---|
| 12αc<br>DAD<br>4.610 | 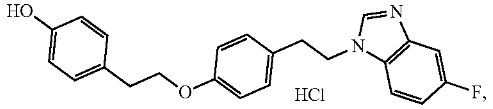 [SMILES: Oc1ccc(CCOc2ccc(CCn3cnc4cc(F)ccc43)cc2)cc1 ; Cl] |
| 12αb<br>DAD<br>4.609 | 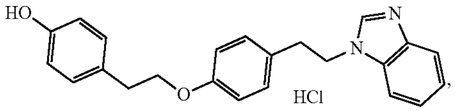 [SMILES: Oc1ccc(CCOc2ccc(CCn3cnc4ccccc43)cc2)cc1 ; Cl ; ","] |

In certain preferred embodiments, the aromatic azole compound is selected from the group consisting of:

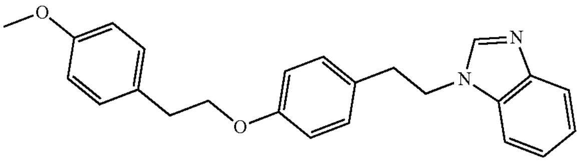

(6αa,DAD 3-473),

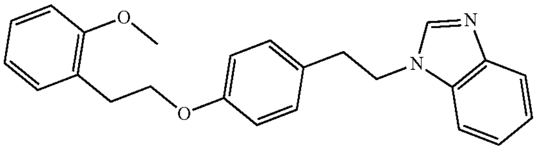

(6αac,DAD 4-566), and

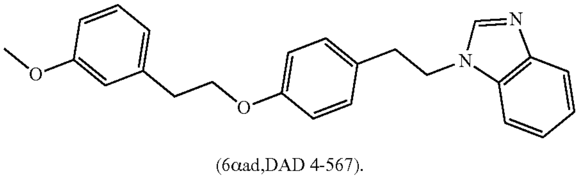

(6αad,DAD 4-567).

In certain embodiments, the aromatic azole compound of chemical formula (I) is such that Z═CONH, i.e., has the chemical formula (II').

In certain embodiments, the aromatic azole compound has the chemical formula (I), wherein Z═CONH and X is:

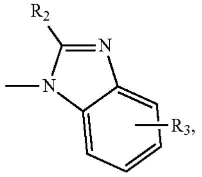

wherein $R_2$ is H, Cl, Br or $CF_3$ and $R_3$ is one, two, three or four substituents, wherein each of the substituents is independently selected from H, OH, $CF_3$, F, Cl, $NH_2$, COOH, and $CONH_2$. The aromatic azole compound then has chemical formula (III').

In certain embodiments, the aromatic azole compound has the chemical formula of one of the amido analogues (7a, 7b, 7c and 7d) presented in Table 8.

In certain embodiments, the aromatic azole compound has the chemical formula (I), wherein Z═$SO_2NH$, i.e., has chemical formula (II").

In certain embodiments, the aromatic azole compound has the chemical formula (I), wherein Z═$SO_2NH$ and X is:

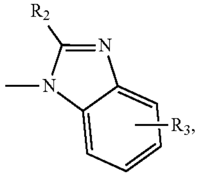

wherein $R_2$ is H, Cl, Br or $CF_3$ and $R_3$ is one, two, three or four substituents, wherein each of the substituents is independently selected from H, OH, $CF_3$, F, Cl, $NH_2$, COOH, and $CONH_2$. The aromatic azole compound then has chemical formula (III").

In certain embodiments, the aromatic azole compound has the chemical formula of one of the sulfamido analogues (9a, 9b, 9c and 9d) presented in Table 9.

B. Preparation of the SOCE Inhibitors

Figure 2:
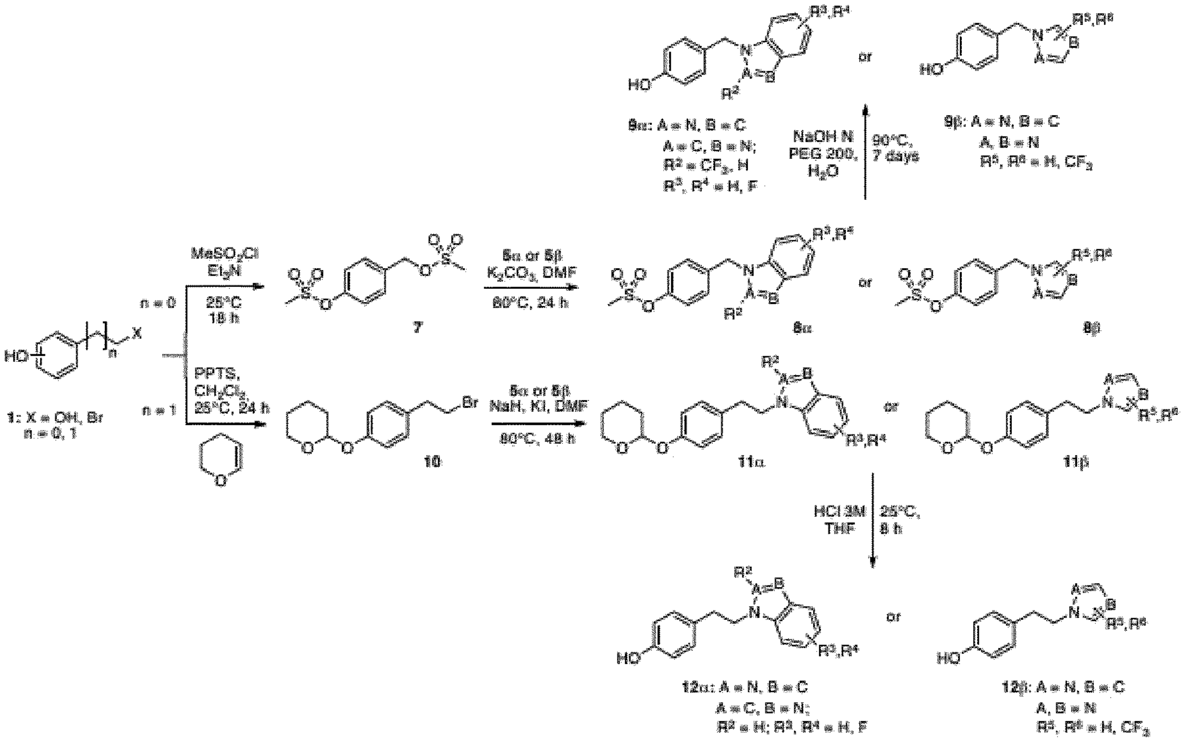
FIG. 2. Chemical Scheme used for the preparation of N-phenylalkyl azole SOCE inhibitors bearing benzimidazole, indazole, pyrazole and triazole platforms with free hydroxyl function on the terminal side chain.

The SOCE inhibitors according to the present invention may be prepared using any of a variety of suitable methods known in the art. Illustrative synthetic reaction schemes are shown in FIGS. 1 and 2 and described in the Experimental Section below. The synthetic schemes are merely illustrative of some methods by which the compounds of the present invention can be synthesized, and various modifications of these synthetic reaction schemes can easily be made by one skilled in the art. In particular, where specific acids, bases, reagents, coupling agents, solvents, etc. are mentioned, it is understood that other bases, acids, reagents, coupling agents, solvents, etc. known in the art may also be used and are therefore included within the scope of the present invention. Variations in reaction conditions and parameters like temperature, pressure, duration of reaction, etc., which may be used as known in the art are also within the scope of the present invention. The starting materials and reagents used in preparing the SOCE inhibitors are either available from commercial suppliers or are prepared by following routine procedures.

The starting materials and the intermediates of the synthetic reaction schemes can be isolated and purified if desired using conventional techniques, including, but not limited to, filtration, distillation, crystallization, chromatography, and the like. The purified materials can be characterized using conventional means, including physical constants and spectral data.

The compounds (SOCE inhibitors) obtained using the general reaction schemes may be of insufficient purity. They can be purified by using any of the methods for purification of organic compounds known in the art, for example, crystallization, chromatography, and the like.

C. SOCE Inhibitor Salts, Solvates, Hydrates, Derivatives, and Prodrugs

In certain embodiments, the SOCE inhibitors of the present invention are provided as a pharmaceutically acceptable salt, solvate or hydrate.

The term "pharmaceutically acceptable salt" refers to those salts which are, within the scope of sound medical judgment, suitable for use in contact with the tissues of humans and lower animals without undue toxicity, irritation, allergic response and the like and are commensurate with a reasonable benefit/risk ratio. Preparation of pharmaceutical salts is well known in the art. When there is an acidic group present in the structure of a pharmaceutically active compound, such as the compounds of the present invention, pharmaceutically acceptable salts can be prepared by contacting the compound with a non-toxic inorganic base, including potassium, sodium, calcium, ammonium, lithium, ferric, copper, and magnesium hydroxides. In some embodiments, pharmaceutically acceptable salts can be prepared by contacting the compound with a non-toxic organic base, including, but not limited to, arginine, betaine, histidine, N-methyl glucamine, lysine, L-glucamine and others. In some embodiments, when a basic group is present in the structure of a pharmaceutically active compound, such as the compounds of the present invention, pharmaceutically acceptable salts can be prepared by contacting the compound with a non-toxic acid, for example, hydrochloric, hydrobromic, sulfuric, acetic, phosphoric, tartaric, citric, fumaric, nitric, gluconic, malic, glutamic, and succinic acids.

As used herein, the term "solvate" refers to solvent addition forms that contain either stoichiometric or non-stoichiometric amounts of solvent. Some compounds tend to trap a fixed molar ratio of solvent molecules in the crystalline solid state, thus forming a solvate. If the solvent is water, the solvate form is called a "hydrate"; when the solvent is alcohol, the solvate formed is called an alcoholate. Hydrates are formed by the combination of one or more molecules of water with one molecule of the substances in which the water retains its molecular state as $H_2O$. Pharmaceuticals solvates or hydrates of the compounds of the present invention can be formed by freeze-drying the solutions of the compounds in water or any other suitable solvent, e.g., methanol, ethanol, DMSO, acetic acid, isopropanol, ethyl acetate, ethanolamine. The general methods of preparation of solvates and hydrates are well known in the art.

The present invention also encompasses derivatives of the SOCE inhibitors described herein. As used herein, a "derivative of a SOCE inhibitor" described herein is a compound having a structure derived from the structure of a parent compound (one of the SOCE inhibitors disclosed herein) and whose structure is sufficiently similar to those disclosed herein and based upon that similarity would be expected by one skilled in the art to exhibit the same or similar activities and utilities as the parent compound, or to induce, as a precursor, the same or similar activities and utilities as the parent compound. Exemplary derivatives include esters, amides, salts of esters or amides, pegylated derivatives of a parent compound and N-oxides of a parent compound.

The present invention also encompasses prodrugs of the SOCE inhibitors described herein. As used herein, the term "prodrugs of a SOCE inhibitor" refers to compounds which are rapidly transformed in vivo into the parent compounds of the chemical formulae provided herein, by a reaction under physiological conditions with an enzyme, a gastric acid or in the living body through oxidation, reduction, hydrolysis or enzymatic reaction. Examples of prodrugs include compounds wherein a carboxyl group is esterified. Such prodrugs can be produced according to methods well known in the art.

D. SOCE Inhibitors Biological Properties

The compounds provided herein have been tested for their ability to inhibit SOCE and the results are presented in Tables 4-7 in the Experimental Section below.

Effects of compounds or agents on intracellular calcium can be monitored using various methods which provide for a direct or indirect evaluation or measurement of cellular (including cytosolic and intracellular organelle or comportment) calcium and/or movement of $Ca^{2+}$ into, within or out of a cell, organelle, calcium store or portions thereof (e.g., a membrane). A variety of methods can be used for evaluating calcium levels and calcium cation movements or flux. The particular method used, and the conditions employed would depend on whether a particular aspect of intracellular calcium is being monitored or assessed. For example, in some aspects, reagents and conditions may be used for specifically evaluating store-operated calcium entry, resting cytosolic calcium levels, calcium buffering and calcium levels and uptake by or release from intracellular organelles and calcium stores. Alternatively, the effect of a compound or agent on intracellular calcium can be monitored or assessed using, for example, a cell, an intracellular organelle or calcium storage compartment, a membrane (including, e.g., a detached membrane, patch or a lipid bilayer) or a cell-free assay system (e.g., outside-out membrane vesicle).

Assays that can be used to study the inhibitory effects of SOCE inhibitors in vitro or in vitro are known in the art, see for example: Vetter, Adv. Exp. Med. Biol., 2012, 740: 45-82; Zhang et al., Methods Mol. Biol., 2018, 1843: 1-16; Zhang et al., Methods Mol. Biol., 2018, 1843: 17-39; Redondo et al., Methods Mol. Biol., 2018, 1843: 69-82; Riva et al., J. Med. Chem., 2018, 61: 9756-9783; Pan et al., J. Vis. Exp., 2012, 60: 3415; Pan et al., Methods Mol. Biol., 2018, 1843: 55-62; Oh-Hara and Lu, "Calcium Entry Channels in Non-Excitable Cells", Boca Raton (FL); CRC Press/Taylor & Francis, 2018, Chapter 6; Stauderman, Cell Calcium, 2018, 74: 147-159; and Sadaghiani et al., Chem. Biol., 2014, 21: 1278-1292.

Processes regulated by store-operated calcium entry include, but are not limited to, calmodium activation, calcineurin activation, mast cell degranulation and release of inflammatory mediators, activation of calcium-dependent transcription factors (e.g., nuclear factor of activated T cells (NFAT), nuclear factor kappa B (NFκB), and/or c-Jun N-terminal kinase (JNK)), NFAT dephosphorylation, NFAT nuclear translocation, NFAT-dependent gene regulation, expression, release and/or activity of molecules regulated by such transcription factors (e.g., cytokine expression, release or activity cytokine release).

Thus, the inhibitory effect of a compound on SOCE may be assessed by detecting the effect on a calcium-entry mediated event. For example, one can detect or determine the activity of calcium-regulated proteins, such as calmodulin and calcineurin; regulation, localization and/or activity of calcium regulated transcription factors such as NFAT, JNK and NFκB; and effects on gene expression, such as genes regulated by calcium-regulated transcription factors, for example, cytokine gene expression such as expression of IL-2, IL-3, IL-4, IL-5, IL-8, IL-13, as well as tumor necrosis factor alpha (TNFα), granulocyte colony-stimulating factor (GCSF), and gamma-interferon (γ-IFN) and/or reporter genes linked to promoters or regulatory elements of such genes. An effect on intracellular calcium can also be assessed by detecting or determining secretion and/or release of peptides and proteins, such as secretion of cytokines such as IL-2, and degranulation and release of inflammatory mediators such as histamine and β-hexosaminidase.

II—Therapeutic Uses of the SOCE Inhibitors

Due to their biological activity, the SOCE inhibitors of the present invention may be used as therapeutic agents. Deregulated SOCE has been implicated in a large number of human disorders, including immunodeficiency diseases (Feske et al., Nature, 2006, 441: 179-185), autoimmune diseases (Bhuvaneshwari et al., Curr. Drug Targets, 2020, 21(1), doi: 10.2174/1389450120666190926150258), cardio-vascular diseases (Groschner et al., Adv. Exp. Med. Biol., 2017, 993: 473-503), skeletal diseases (Michelucci et al., Cell Calcium, 2018, 76: 101-115), cardiorespiratory diseases (Rode et al., Physiology, 2018, 33: 261-268; Spinelli et al., Am. J. Physiol. Cell Physiol., 2016, 310: C402-413), neurodegenerative diseases (Wegierski et al., Cell Calcium, 2018, 74: 101-111), allergies (Peters-Golden et al., Clin. Exp. Allergy, 2006, 36: 689-703), asthma (Kaur et al., Pulm. Pharmacol. Ther., 2015, 35: 67-74), thrombosis (Braun et al., Blood, 2008, 113: 2056-2063; Mammadova-Bach et al., Cell Calcium, 2019, 77: 39-48), pancreatitis (Gerasimenko et al., PNAS USA, 2013, 110: 13186-13191), inflammatory bowel diseases (Feske et al., Nature Rev. Immunol., 2007, 7: 690-702) and cancers (Yang et al., Cancer Cell, 2009, 15: 124-134; Hanahan et al., Cell, 2000, 100: 57-70; Xi et al., Int. J. Cancer, 2016, 138: 2067-2077; Chen et al., Cancers, 2019, 11: E899; Bong et al., Biochim. Biophys. Acta Mol. Cell Res., 2018, 1865: 1786-1794; Chalmers et al., Cell Calcium, 2018, 74: 160-167).

A. Indications

Consequently, the present invention relates to a SOCE inhibitor described herein for use as a therapeutic agent in the treatment of a disease associated with SOCE dysregulation or dysfunction in a subject. The present invention also relates to the use of a SOCE inhibitor as described herein in the preparation of a medicament for the treatment of disease associated with SOCE dysregulation or dysfunction. The present invention further relates to a method of treatment of a disease associated with SOCE dysregulation or dysfunction in a subject, comprising a step of administering to the subject in need thereof a therapeutically effective amount a SOCE inhibitor as described herein.

As used herein, the term "subject" refers to a human or another mammal (e.g., primate, mouse, rat, rabbit, dog, cat, horse, cow, pig, camel, and the like). In many embodiments of the present invention, the subject is a human being. In such embodiments, the subject is often referred to as an "individual" or a "patient". The terms "individual" and "patient" do not denote a particular age.

The term "treatment" is used herein to characterize a method or process that is aimed at (1) delaying or preventing the onset of a disease or condition; (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively, or additionally, a treatment may be administered after initiation of the disease or condition, for a therapeutic action.

As used herein, the term "therapeutically effective amount" refers to an amount of a compound (here a SOCE inhibitor) effective, at dosages and for periods of time necessary, to achieve the desired biological or medical response or result. A therapeutically effective amount of a compound can vary according to factors such as the disease state, age, sex, and weight of the subject, the ability of the compound to elicit the desired response in the subject, and the route of administration. An individual therapeutically effective amount can be determined according to the methods known in the art. Dosage regimens can be adjusted to provide the optimum therapeutic response. Adjusting the dose to achieve maximal efficacy based on these or other methods are well known in the art and are within the capabilities of trained physicians. A therapeutically effective amount is also one in which any toxic or detrimental effects of the compound are outweighed by the therapeutically beneficial effects. A therapeutically effective amount may consist of a single dose or multiple doses. Thus, administration of an inventive SOCE inhibitor described herein may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week, two or more times per month, and the like. The delivery may be continuous delivery for a period of time, e.g., intravenous delivery.

A "therapeutically desired biological or medical response or result" is understood to be an improved treatment, healing, prevention, or amelioration of a disease, disorder, or side effect, or a decrease in the rate of advancement of a disease or disorder in a subject, as compared to a corresponding subject who has not been administered such amount. The term "therapeutically desired biological or medical response" also includes the enhancement of a normal physiological function.

As used herein, the term "disease associated with SOCE dysregulation or dysfunction" refers to any disease, disorder or condition, which is characterized by an impairment, disturbance, perturbation or imbalance in the mechanism of cellular calcium signaling of SOCE. The disease may be congenital or acquired. The term also encompasses all the pathologies associated with loss, null or gain-of-function mutations of STIM/ORAI.

Examples of classes of diseases known to be associated with SOCE dysregulation or dysfunction include, but are not limited to, inflammatory diseases, immune system diseases, cardiovascular diseases, cardiorespiratory diseases, vascular diseases, neurodegenerative diseases, skeletal muscle diseases, thromboses, and cancers.

In certain embodiments, a SOCE inhibitor described herein is used in the treatment or prevention of an inflammatory disease. As used herein, the term "inflammatory disease" refers to a disease, condition or disorder characterized by inflammation of body tissue or having an inflammatory component. An inflammatory disease may result from, or be triggered by, a dysregulation of the normal immune response. Examples of inflammatory conditions that can be treated using a SOCE inhibitor described herein include, but are not limited to, diseases of many body systems such as:

- Inflammatory diseases of the musculoskeletal system, including myositis, rheumatoid arthritis, osteoarthritis, gout, gouty arthritis, acute pseudo gout, Reiter's syndrome, ankylosing spondylitis, psoriatic arthritis, dermatomyositis, and bone diseases associated with increased bone resorption;
- Inflammatory diseases of the pulmonary system, including pleuritis, pulmonary fibrosis or nodules, restrictive lung disease, chronic obstructive pulmonary disease (COPD), and acute respiratory distress syndrome (ARDS);
- Inflammatory diseases of the cardiovascular system, including aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, and myocardial infarction;
- Inflammatory diseases of the gastrointestinal system, including dysmotility, dysphagia, inflammatory bowel diseases (such as Crohn's disease, ulcerative colitis, indeterminate colitis, necrotizing enterocolitis, ileitis, infectious colitis, and Barrett's syndrome), and pancreatitis;
- Inflammatory diseases of the genitourinary system, including interstitial cystitis, renal tubular acidosis, vaginitis, and urosepsis;
- Inflammatory diseases of the skin, including purpura, vasculitis scleroderma, sclerodermatitis, eczema, and psoriasis;
- Inflammatory diseases of the neurologic system, including central nervous system disorders, cranial and peripheral neuropathies, peripheral neuropathy, radiculopathy, spinal cord or cauda *equina* compression with sensory and motor loss, and multiple sclerosis (MS);
- Inflammatory diseases of the central nervous system, including chronic demyelinating diseases of the nervous system, cognitive dysfunction, multiple sclerosis (MS), AIDS-related neurodegeneration, Alzheimer's disease, infectious meningitis, encephalomyelitis, Parkinson's disease, Huntington's disease, amyotrophic lateral sclerosis, and viral or autoimmune encephalitis:
- Inflammatory diseases of the ophthalmic system, including iridocyclitis, keratoconjunctivitis sicca, uveitis, corneal dystrophy, trachoma, onchocerciasis, sympathetic ophthalmitis and endophthalmitis;
- Inflammatory diseases of the hematologic system, including chronic anemia, and thrombocytopenia;
- Inflammatory diseases of the renal system, including amyloidosis of the kidney, glomerulonephritis, nephrosis, and kidney failure; and
- Other inflammatory diseases such as tuberculosis, leprosy, sarcoidosis, syphilis, Sjogren's syndrome, cystitis, fibromyalgia, fibrosis, septic shock, endotoxic shock, surgical complications, systemic lupus erthymotosus (SLE), transplantation associated arteriopathy, graft-versus-host reaction, allograft rejection, chronic transplant rejection.

In certain embodiments, a SOCE inhibitor described herein is used in the treatment or prevention of an immune disorder. The terms "immune disorder" and "immune system disease" are used herein interchangeably and refer to a disease or disorder or abnormality caused by dysfunction or malfunction of the immune system as a whole or any of its components including autoimmune disorders. Immune disorders can be congenital or acquired and may be characterized by the component(s) of the immune system getting affected or by the immune system or its components getting overactive. Immune disorders include those diseases, disorders or conditions that have an immune component and those that arise substantially or entirely due to immune system-mediated mechanisms. Since a number of immune disorders are caused by inflammation or lead to inflammation, there is some overlap between disorders that are considered immune disorders and disorders that are considered inflammation disorders. For the purpose of the present invention, in the case of such an overlapping disorder, it may be considered either an immune disorder or an inflammatory disorder.

In particular, the terms "immune system disease" and "immune disorder" refer to a series of disorders of the immune system, including immunodeficiency disorders, autoimmune disorders, and overactive immune response (allergic disorders).

Thus, in certain embodiments, a SOCE inhibitor described herein is used in the treatment or prevention of an immunodeficiency disorder. As used herein, the term "immunodeficiency disorder" refers to a disease, disorder or condition that occurs when the body's immune response is reduced or absent. When the disease is congenital or genetic, it is called a primary immunodeficiency disease; when the disease is acquired, it is called a secondary immunodeficiency disease. Examples of primary immunodeficiency diseases that can be treated using a SOCE inhibitor described herein include, but are not limited to, X-linked agammaglobulinemia (XLA), common variable immunodeficiency (CVID), severe combined immunodeficiency (SCID), which is known as alymphocytosis or "boy in a bubble" disease, DiGeorge syndrome, and Wiskott-Aldrich Syndrome. Secondary immunodeficiency disorders happen when an outside source like a toxic chemical or infection attacks the body (e.g., severe burns, chemotherapy, radiation, diabetes, malnutrition, immunosuppressive drugs). Examples of secondary immunodeficiency diseases that can be treated using a SOCE inhibitor described herein include, but are not limited to, AIDS, immune-complexe diseases, like viral hepatitis, cancer of the bone marrow and blood cells (leukemia, lymphoma, multiple myeloma).

In certain embodiments, a SOCE inhibitor described herein is used in the treatment or prevention of an autoimmune disorder. As used herein, the term "autoimmune disorder" refers to a disease or disorder or abnormality that occurs when the immune system mistakenly attacks and destroys its own body cells, tissues and/or organs. Examples of autoimmune disorders that can be treated using a SOCE inhibitor described herein include, but are not limited to,

- Autoimmune disorders of the skin, such as psoriasis, dermatitis herpetiformis, pemphigus vulgaris, alopecia areata, bullous pemphigoid, and vitiligo;
- Autoimmune disorders of the gastrointestinal system, such as coeliac disease, inflammatory bowel disease (e.g., Crohn's disease), ulcerative colitis, primary biliary cirrhosis, and autoimmune hepatitis, primary sclerosing, cholangitis, and autoimmune pancreatitis;

Autoimmune disorders of the endocrine glands, such as Type 1 diabetes mellitus, autoimmune thryroiditis, Grave's disease. Hashimoto's thyroiditis, autoimmune oophoritis, orchitis, and autoimmune disorder of the adrenal gland, e.g., Addisons disease;

Autoimmune disorders of multiple organs, such as including connective tissue and musculoskeletal system diseases (e.g., rheumatoid arthritis, systemic lupus erythematosus, scleroderma, polymyositis, dermatomyositis, spondyloarthropathies, e.g., ankylosing spondylitis and psoriasis arthritis), graft-versus-host disease (GVHD);

Autoimmune disorders of the neuromuscular system, such as multiple sclerosis (MS), myasthenia gravis, Eaton-Lambert Myasthenic syndrome, autoimmune neuropathies such as Guillain-Barre, autoimmune uveitis, juvenile myositis, autoimmune retinopathy, acute inflammatory demyelinating polyneuropathy, chronic inflammatory demyelinating polyneuropathy, chronic inflammatory demyelinating polyradiculoneuropathy, encephalomyelitis, neuromyotonia, Stiff man syndrome, and paraneoplastic neurological disorders;

Autoimmune disorders of the blood, such as autoimmune hemolytic anemia, pernicious anemia, autoimmune thrombocytopenia; and autoimmune lymphoproliferative syndrome;

Autoimmune disorders of the blood vessels, such as temporal arthritis, anti-phospholipid syndrome, vasculitidis syndromes e.g., Wegener's granulomatosis, and Behcet's disease; cryoglobulinemia, systemic necrotizing vasculitides, giant cell arteritis, polyarteritis nodosa, Churg-Strauss syndrome, hypersensitivity vasculitis, Takayasu's arteritis, Kawasaki disease, and cryoglobulinemia;

Autoimmune disorders of the eye, such as autoimmune uveitis Meniere's disease, and autoimmune inner ear disease;

Autoimmune disorders of the kidney such as glomerulonephritis; and

Autoimmune disorders of the exocrine glands, such as Sjogren's syndrome, Raynaud's phenomenon, Ig1 related diseases.

In yet other embodiments, a SOCE inhibitor described herein is used in the treatment or prevention of an allergic disorder. As used herein, the term "allergic disorder" refers to a disease, condition or disorder associated with an allergic response against normally innocuous substances. These substances may be found in the environment (such as indoor air pollutants and aeroallergens) or they may be non-environmental (such as those causing dermatological or food allergies). Examples of allergic disorders include, but are not limited to, rhinitis (such as allergic rhinitis, e.g., hay fever), sinusitis, rhinosinusitis, allergic conjunctivitis, chronic or recurrent otitis media, drug and vaccine reactions, insect sting reactions, latex allergy, conjunctivitis, urticarial (including chronic idiopathic urticarial), anaphylaxis and anaphylactoid reactions, atopic dermatitis, contact dermatitis, pruritus, asthma, allergic bronchitis, allergic bronchopulmonary aspergillosis, seasonal allergies and food allergies.

In particular, in certain embodiments, a SOCE inhibitor described herein is used in the treatment or prevention of asthma. As used herein, the term "asthma" refers to a pulmonary disease, disorder or condition characterized by reversible airway obstruction, airway inflammation, and increased airway responsiveness to a variety of stimuli.

In certain embodiments, a SOCE inhibitor described herein is used in the treatment or prevention of a cardiovascular disease. As used herein, the term "cardiovascular diseases" refers to a structural and functional abnormality of the heart and blood vessels, which may be congenital or acquired. Examples of cardiovascular diseases that can be treated using a SOCE inhibitor described herein include, but are not limited to, atherosclerosis, restenosis, coronary artery disease, arrhythmia, diabetic angiopathies, heart failure, hypertension, hypertrophy, diseases of the aorta and its branches, disorders of the peripheral vascular system, aneurysm, endocarditis, pericarditis, heart valve disease, ischemic injury associated with myocardial infractions, stroke, vascular thrombosis rheumatic heart disease, pulmonary embolism hypertension, and vascular thrombosis.

In certain embodiments, a SOCE inhibitor described herein is used in the treatment or prevention of a cardiorespiratory disease. As used herein, the term "cardiorespiratory diseases" refers to a range of serious disorders that affect the heart and lungs. Examples of cardiorespiratory diseases that can be treated using a SOCE inhibitor described herein include, but are not limited to, chronic obstructive pulmonary disorder (COPD), congestive cardiac failure (CCF), bronchiectasis, bronchitis, emphysema, and pneumonia.

In certain embodiments, a SOCE inhibitor described herein is used in the treatment or prevention of a neurodegenerative disease. As used herein, the term "neurodegenerative disease" refers to a range of conditions which primarily affect the neurons in the human brain. Examples of neurodegenerative diseases that can be treated using a SOCE inhibitor described herein include, but are not limited to, Alzheimer's disease, Parkinson's disease, Huntington's disease, amyotrophic lateral sclerosis (ALS), AIDS-related dementia, retinitis pigmentosa, spinal muscular atrophy, Batten disease, hypoxic/ischemic damage, strokes, and cerebellar degeneration.

In certain embodiments, a SOCE inhibitor described herein is used in the treatment or prevention of a vascular disease. As used herein, the term "vascular disease" refers to a class of diseases of the blood vessels—arteries and veins of the circulatory system of the body. Examples of vascular diseases that can be treated using a SOCE inhibitor described herein include, but are not limited to, erythromelalgia, peripheral artery disease (PAD), renal artery stenosis, Buerger disease, Raynaud's disease, disseminated intravascular coagulation (DIC), cerebrovascular disease, abdominal aortic aneurysm (AAA), carotid artery disease (CAD), arteriovenous malformation (AVM), critical limb ischemia (CLI), pulmonary embolism, deep vein thrombosis (DVT), chronic venous insufficiency (CVI), atherosclerosis, stenosis, and varicose.

In certain embodiments, a SOCE inhibitor described herein is used in the treatment or prevention of a skeletal muscle disease. The term "skeletal muscle disease" refers to a class of diseases that affect muscle function and/or cause muscle pain. Examples of skeletal diseases that can be treated using a SOCE inhibitor described herein include, but are not limited to, muscular dystrophies, myopathies, dermatomyositis, polymyositis, rhabdomyolysis, diseases of the neuromuscular junction, fibromyalgia, malignant paraganglionic neoplasm, malignant hyperpyrexia due to anesthesia.

In certain embodiments, a SOCE inhibitor described herein is used in the treatment or prevention of a thrombosis. As used herein, the term "thrombosis" refers to a class of diseases characterized by the formation of a blood clot inside a blood vessel, obstructing the flow of blood through the circulatory system. Examples of thromboses that can be treated using a SOCE inhibitor described herein include, but are not limited to, venous thromboses (such as superficial venous thromboses, deep vein thromboses (DVTs), venous thromboembolism (VTE), cerebral venous sinus thrombosis, mesenteric vein thrombosis, renal vein thrombosis, portal vein thrombosis, jugular vein thrombosis, Paget-Schroetter disease, Budd-Chiari syndrome); arterial thrombosis (stroke; myocardial infarction; limb ischemia; and hepatic artery thrombosis).

In certain embodiments, a SOCE inhibitor described herein is used in the treatment or prevention of allelic conditions caused by dominant mutations in STIM1: tubular aggregate myopathy, Stormorken syndrome (a complex phenotype including myopathy, hyposplenism, hypocalcaemia and bleeding diathesis), and a platelet dysfunction disorder, York platelet syndrome.

In certain embodiments, a SOCE inhibitor described herein is used in the treatment or prevention of thrombocytopenia or idiopathic thrombocytopenia.

In certain embodiments, a SOCE inhibitor described herein is used in the treatment or prevention of a cancer. Examples of cancers include, but are not limited to:

- Breast cancer, prostate cancer, liver cancer, lung cancer, colon cancer, cervical cancer, kidney cancer, lung cancer, bladder cancer, nasopharyngeal cancer, epidermoid cancer, esophageal cancer, stomach cancer, pancreatic cancer, thyroid cancer, neck cancer, skin cancer, and the like;
- Tumors of mesenchymal origin, including rhabdomyosarcoma (an aggressive and highly malignant form of cancer that develops from skeletal muscle cells that have failed to fully differentiate);
- Hematopoietic tumors of lymphoid lineage, including leukemia, acute lymphocytic leukemia, acute lymphoblastic leukemia, Hodgkin's lymphoma, non-Hodgkin's lymphoma, B-cell lymphoma, T-cell lymphoma, hairy cell lymphoma, and Burkett's lymphoma;
- Hematopoietic tumors of myeloid lineage, including acute and chronic myelogenous leukemias, myelodysplastic syndrome and promyelocytic leukemia;
- Tumors of the central and peripheral nervous system, including astrocytoma, neuroblastoma, glioma and schwannomas; and
- Other tumors, including melanoma, thyroid follicular cancer, Kaposi's sarcoma, osteosarcoma, seminoma, teratocarcinoma and keratocanthama.

In certain preferred embodiments, a SOCE inhibitor described herein is used in the treatment or prevention of a disease selected from the group consisting of rheumatoid arthritis, multiple sclerosis, asthma, psoriasis, inflammatory bowel diseases, hepatitis, pancreatitis, metabolic disorders such as diabetes, and cancers.

B. Administration

A SOCE inhibitor (optionally after formulation with one or more appropriate pharmaceutically acceptable carriers or excipients) can be administered to a subject in need thereof by any suitable route. Various delivery systems are known and can be used to administer SOCE inhibitors of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An inventive SOCE inhibitor, or composition thereof, may be administered by any convenient or other appropriate route, for example, by infusion or bolus injection, by adsorption through epithelial or mucocutaneous linings (e.g., oral, mucosa, rectal and intestinal mucosa, etc). Administration can be systemic or local. Parenteral administration may be directed to a given tissue of the patient, such as by catheterization.

In certain embodiments, an inventive SOCE inhibitor, or a pharmaceutical composition thereof, is administered alone according to a method of treatment of the present invention. In other embodiments, an inventive SOCE inhibitor, or a composition thereof, is administered in combination with at least one additional therapeutic agent or therapeutic procedure. The SOCE inhibitor, or composition thereof, may be administered prior to administration of the additional therapeutic agent or therapeutic procedure, concurrently with the therapeutic agent or procedure, and/or following administration of the additional therapeutic agent or procedure.

Therapeutic procedures that may be performed in combination with administration of an inventive SOCE inhibitor, or composition thereof, include, but are not limited to, surgery, catheterization and other invasive therapeutic procedures.

Therapeutic agents that may be administered in combination with an inventive SOCE inhibitor, or composition thereof, may be selected among a large variety of biologically active compounds including compounds that are known to have a beneficial effect in the treatment or prevention of a disease associated with SOCE dysregulation or dysfunction as defined above; compounds that increase the availability and/or activity of the SOCE inhibitor; and compounds that are generally beneficial to the subject's health. Examples of such biologically active compounds include, but are not limited to, anti-inflammatory agents, immunomodulatory agents, analgesics, antimicrobial agents, antibacterial agents, antibiotics, antioxidants, antiseptic agents, and the like. As will be appreciated by those of ordinary skill in the art, in embodiments where an inventive SOCE inhibitor is administered along with an additional therapeutic agent, the SOCE inhibitor and the therapeutic agent may be administered by the same route (e.g., orally) or by different routes (e.g., orally and intravenously).

In embodiments where the disease associated with SOCE dysregulation or dysfunction relates to autoimmune, allergic or inflammatory conditions, the additional therapeutic agent may be a steroid or a non-steroidal anti-inflammatory agent. Examples of suitable non-steroidal anti-inflammatory agents (NSAIDs) that can be used in combination with a SOCE inhibitor described herein include, but are not limited to, aspirin, ibuprofen, diclofenac, naproxen, benoxaprofen, flurbiprofen, fenoprofen, flubofen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof.

In embodiments where the disease associated with SOCE dysregulation or dysfunction relates allergic disorders, the other therapeutic agent may be an antihistamine. Examples of antihistamines that can be used in combination with a SOCE inhibitor described herein include, but are not limited to, loratadine, certizine, fexofenadine, desloratadine, diphenhydramine, chlorpheniramine, chlorcyclizine, pyrilamine, promethazine, terfenadine, doxepin, carbinoxamine, clemastine, tripeiennamine, brompheniramine, hydroxyzine, cyclizine, meclizine, cyproheptadine, phenindamine, acrivastine, azelastine, levocabastine, and mixtures thereof. Other examples of suitable antihistamines can be found in Goofman and Gilman, "The Pharmacological Basis of Therapeutics", 2001, $10^{th}$ Ed., pp. 651-657.

Examples of immunosuppressive agents that can be used in combination with a SOCE inhibitor described herein include, but are not limited to, glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, busulfan and cyclophosphalide), folic acid antagonists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL2 receptor, anti-alpha/beta TCR, anti-ICAN-1, anti-CD20 (Rituxan), anti-IL-12 and antibodies to immunotoxins).

In embodiments where the disease associated with SOCE dysregulation or dysfunction relates to cancers, the other therapeutic agent may be an anti-cancer agent. Examples of anti-cancer agents that can be used in combination with a SOCE inhibitor described herein include drugs conventionally classified in one of the following groups: alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine. Other examples of such anti-cancer agents include therapeutic antibodies used in the treatment of cancer, including, but are not limited to, anti-CD52 antibodies such as alemtuzumab (CAMPATH™), which is used in the treatment of chronic lymphocytic leukemia; anti-VEGF antibodies including bevacizumab (AVASTIN™) which is used in the treatment of colorectal cancer and breast cancer; anti-CD33 antibodies, including gemtuzumab ozogamicin (MYLOTARG™) which is used in the treatment of acute myeloid leukemia; anti-CD20 antibodies including ibritumomab (ZEVALIN™) which is used in the treatment of lymphoma, rituximab (RITUXAN™) which is used in the treatment of Hodgkin lymphoma, tositumomab (BEXXAR™) which is used in the treatment of Hodgkin lymphoma and of atumumab (ARZERRA™) which is used in the treatment of chronic lymphocytic leukemia; anti-EGFR antibodies such as cetuximab (ERBITUX™) which is used in the treatment of colorectal cancer, head and neck cancer, and squamous cell carcinoma, and panitumumab (VECTIBEX™) which is used in the treatment of colorectal cancer; anti-Her2 antibodies, including trastuzumab (HERCEPTIN™) which is used in the treatment of breast cancer and stomach cancer; and anti-CTLA4 antibodies including Ipilimumab (YERVOY™) which is used in the treatment of melanoma.

It is within the capabilities of one skilled in the art to select a therapeutic agent to design suitable combinations with a SOCE inhibitor for the treatment or prevention of a disease associated with SOCE dysregulation or dysfunction.

III—Pharmaceutical Compositions

As mentioned above, a SOCE inhibitor described herein may be administered per se or as a pharmaceutical composition. Accordingly, the present invention provides pharmaceutical compositions comprising an effective amount of a SOCE inhibitor and at least one pharmaceutically acceptable carrier or excipient. In some embodiments, the composition further comprises one or more additional biologically active agents.

As used herein, the term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, $18^{th}$ Ed., 1990, Mack Publishing Co.: Easton, PA, which is incorporated herein by reference in its entirety). In certain embodiments, the pharmaceutically acceptable carrier or excipient is a veterinary acceptable carrier or excipient.

The SOCE inhibitors and pharmaceutical compositions thereof may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of a SOCE inhibitor of the invention for the patient to be treated. It will be understood, however, that the total daily dosage of the compositions will be decided by the attending physician within the scope of sound medical judgment.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose, any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient, it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly (anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the SOCE inhibitor, the liquid dosage form may contain inert diluents commonly used in the art such as, for example, water or other solvent, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavoring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and *arachis* oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive SOCE inhibitor may be mixed with at least one inert, pharmaceutically acceptable excipient or carrier such as sodium citrate or dicalcium phosphate and one or more of (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment. This may be achieved, for example, and not by way of limitation, by local infusion during surgery, topical application, by injection, by means of a catheter, by means of suppository, or by means of a skin patch or stent or another implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., the SOCE inhibitor) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18th Ed., 1990, Mack Publishing Co.: Easton, PA.

B. Additional Biologically Active Agents

In certain embodiments, an inventive SOCE inhibitor is the only active ingredient in a pharmaceutical composition of the present invention. In other embodiments, the pharmaceutical composition further comprises one or more biologically active agents. Examples of suitable biologically active agents include, but are not limited to, anti-inflammatory agents, immunomodulatory agents, analgesics, antimicrobial agents, antibacterial agents, antibiotics, antioxidants, antiseptic agents, and combinations thereof.

In such pharmaceutical compositions, the SOCE inhibitor and the at least one additional therapeutic agent may be combined in one or more preparations for simultaneous, separate or sequential administration of the SOCE inhibitor and therapeutic agent(s). More specifically, an inventive composition may be formulated in such a way that the SOCE inhibitor and therapeutic agent(s) can be administered together or independently from each other. For example, the SOCE inhibitor and therapeutic agent can be formulated together in a single composition. Alternatively, they may be maintained (e.g., in different compositions and/or containers) and administered separately.

C. Pharmaceutical Packs or Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of a SOCE inhibitor of the present invention.

Different ingredients of a pharmaceutical pack or kit may be supplied in a solid (e.g., lyophilized) or liquid form. Each ingredient will generally be suitable as aliquoted in its respective container or provided in a concentrated form. Packs or kits according to the invention may include media for the reconstitution of lyophilized ingredients. Individual containers of the kits will preferably be maintained in close confinement for commercial sale.

In certain embodiments, a pack or kit includes one or more additional therapeutic agent(s). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually carried out or data were actually obtained.

I. Chemical Synthesis of the SOCE Inhibitors

The routes used for the preparation of N-phenylalkyl azole derivatives (with or without free hydroxyl function on the terminal side chain appended to the azole heterocyclic platform) are presented below.

Part 1

The chemical scheme used for the preparation of N-phenylalkyl azole SOCE inhibitors bearing benzimidazole, indazole, pyrazole and triazole platforms without free hydroxyl function on the terminal side chain is presented in FIG. 1.

Example 1

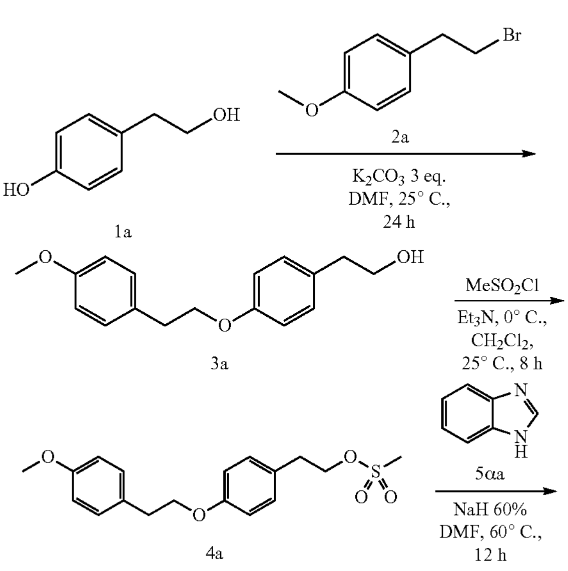

2a

1a

3a

5αa

4a

-continued

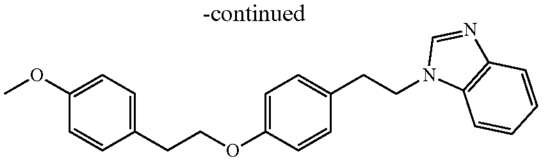

6αa (DAD3-473)

2-(4-(4-Methoxyphenethoxy)phenyl)ethan-1-ol (3a). To a solution of 2-(4-hydroxyphenyl)ethanol 1a (3.75 g, 27.14 mmol) in 15 ml of dry N,N-dimethylformamide (DMF) under vigorous magnetic stirring (550 rpm) was added portion-wise 11.25 g of potassium carbonate $K_2CO_3$ (8.43 mmol, 3 equiv.) at room temperature. After 30 minutes, 5.838 g of 4-methoxyphenethyl bromide 2a (27.14 mmol) was added drop-wise during 30 minutes at 25° C. and stirring was pursued for 24 hours (monitored by thin layer chromatography on 0.2 mm plates of silica gel 60F-254 Merck using $CH_2Cl_2$/MeOH 95:5 v/v as eluent). Deionised water (150 ml) was added directly to the crude reaction mixture and stirring was maintained until complete precipitation. The insoluble material was recovered by filtration in a Buchner funnel (porosity No 4) and the precipitate was washed successively with deionised water (3×50 ml) and then with hexane (2×50 ml). The resulting precipitate was stirred in hexane (50 ml) and the suspension was concentrated under reduced pressure using a rotary evaporator. The resulting solid was further dried under high vacuum ($10^{-3}$ Torr) and afforded the desired compound 3a as white powder in 41% yield. The compound 3a was found to be pure enough to be used later without further purification. Mp=73-74° C.

$^1$H NMR (300 MHz, DMSO-$d_6$) δ=1.96 (m, 2H, $CH_2$, H-2'), 2.65 (td, J=7.1, 5.1 Hz, 4H, $CH_2$, H-2, H-3'), 3.55 (q, J=6.6 Hz, 2H, $CH_2$, H-1), 3.71 (s, 3H, $OCH_3$), 3.89 (t, J=6.4 Hz, $CH_2$, 2H, H-1'), 4.61 (t, J=5.2 Hz, 1H, OH), 6.83 (t, J=7.7 Hz, 4H, H-$2^a$, H-$6^a$, H-2, H-$6^b$, Ar) 7.12 (t, J=8.6 Hz, 4H, H-3, H-5, H-3, H-5, Ar).

$^{13}$C NMR (75 MHz, DMSO-$d_6$) δ=30.6 (C-3'), 30.7 (C-2'), 38.2 (C-2), 55.0 ($OCH_3$), 62.5 (C-1), 66.5 (C-1'), 113.8 (C-$3^b$, C-$5^b$), 114.2 (C-$3^a$, C-$5^a$), 129.3 (C-$2^b$, C-$6^b$), 129.8 (C-$2^a$, C-$6^a$), 131.3 (C-$1^a$), 133.2 (C-$1^b$), 156.9 (C-$4^a$), 157.5 (C-$4^b$). HRMS, m/z=295.1310 found (calculated for $C_{18}H_{22}O_3Na$ $[M+Na]^+$ requires 295.1311).

4-(4-Methoxyphenethoxy)phenethyl methanesulfonate (4a). A solution of methanesulfonyl chloride (2.55 g, 22.2 mmol, 2 equiv.) in anhydrous methylene chloride ($CH_2Cl_2$) (3.5 ml) was added dropwise for 15 minutes under magnetic stirring (500 rpm) in a cooled solution (0° C., ice bath) of 2-(4-(4-methoxy-phenethoxy)phenyl)ethan-1-ol 3a (3.027 g, 11.1 mmol) and triethylamine TEA (1.12 g, 27.75 mmol, 2.5 eq.) in 8 ml of dry $CH_2Cl_2$. Stirring at room temperature was further pursued for 8 hours. The crude reaction mixture was transferred into a separating funnel. The organic layer was successively washed with deionised water (3×100 ml), and saturated sodium hydrogenocarbonate $NaHCO_3$ (3×100 ml). After decantation, the organic layer was dried over anhydrous $MgSO_4$, filtered on a paper filter and the filtrate was concentrated in a rotary evaporator under reduced pressure. After standing, the viscous oil crystallized progressively and gave the desired compound as white powder in 78% yield. Mp=51-52° C.

$^1$H NMR (300 MHz, DMSO-$d_6$) δ=2.93 (dt, J=10.4, 6.8 Hz, 4H, $CH_2$, H-2, H-2'). 3.10 (s, 3H, $SCH_3$), 3.72 (s, 3H, $OCH_3$), 4.11 (t, J=6.9 Hz, 2H, $CH_2$, H-1), 4.35 (t, J=6.8 Hz, 2H, $CH_2$, H-1'), 6.79-6.98 (m, 4H, H-$3^a$, H-$5^a$, H-$3^b$, H-$5^b$, Ar), 7.19 (d, J=8.6 Hz, 2H, H-$2^b$, H-6b, Ar), 7.24 (d, J=8.7 Hz, 2H, H-$2^a$, H-$6^a$, Ar).

$^{13}$C NMR (75 MHz, DMSO-$d_6$) δ=33.9 (C-2), 34.1 (C-2'), 36.6 ($SCH_3$), 55.1 ($OCH_3$), 68.4 (C-1'), 70.9 (C-1), 113.8 (C-$3^a$, C-$5^a$), 114.4 (C-$3^b$, C-$5^b$), 128.8 (C-$1^a$), 129.9 (C-$2^b$, C-$6^b$), 130.0 (C-$2^a$, C-$6^a$), 130.2 (C-$1^b$), 157.3 (C-$4^a$), 157.8 (C-$4^b$).

HRMS, m/z=373.1086 found (calculated for $C_{18}H_{22}O_5NaS$ $[M+Na]^+$ requires 373.1084).

1-[4-(4-Methoxyphenethoxy)phenethyl]-1H-benzo[d]imidazole (6αa). To a vigorous stirred (550 rpm) solution of benzimidazole 5αa (2 mmol) in 3.4 ml of DMF was added portion-wise sodium hydride 60% dispersion in mineral oil (0.081 g, 2 mmol) and the resulting suspension is stirred for 5 minutes. After addition of 4-(4-methoxyphenethoxy)phenethyl methanesulfonate 4a (1 mmol) in one portion, the reaction mixture is heated at 60° C. for 12 hours. After cooling down to room temperature, deionised water (34 ml) was added to the reaction mixture, the flask was shaken manually and then stored at 4° C. (refrigerator) for 6 hours until complete precipitation. The insoluble material was recovered by filtration in a Buchner funnel (porosity No 4) and the precipitate was washed successively with deionised water (3×17 ml) and hexane (3×7 ml). The resulting solid was further dried under high vacuum ($10^{-3}$ Torr) and afforded 0.307 g of the desired compound 6αa as white powder in 77% yield. Mp=116-118° C.

$^1$H NMR (300 MHz, DMSO-$d_6$) δ=2.92 (t, J=6.9 Hz, 2H, $CH_2$, H-2'), 3.03 (t, J=7.2 Hz, 2H, $CH_2$, H-2"), 3.72 (s, 3H, $OCH_3$), 4.07 (t, J=6.9 Hz, 2H, $CH_2$, H-1'), 4.43 (t, J=7.2 Hz, 2H, $CH_2$, H-1"), 6.79 (d, J=8.1 Hz, 2H, H-$3^b$, H-$5^b$, Ar), 6.86 (d, J=8.6 Hz, 2H, H-$3^a$, H-$5^a$, Ar), 7.04 (d, J=8.1 Hz, 2H, H-$2^b$, H-$6^b$, Ar), 7.21 (ddd, J=10.5, 6.0, 2.7 Hz, 4H, H-$2^a$, H-$6^a$, H-6, H-7, Ar), 7.55-7.65 (m, 2H, H-5, H-8, Ar), 8.00 (s, 1H, H-2).

$^{13}$C NMR (75 MHz, DMSO-$d_6$) δ=34.1 (C-2'), 34.5 (C-2"), 45.7 (C-1"), 55.0 ($OCH_3$), 68.3 (C-1'), 110.5 (C-5), 113.8 (C-$3^b$, C-$5^b$), 114.4 (C-$3^a$, C-$5^a$), 119.4 (C-8), 121.4 (C-6), 122.2 (C-7), 129.8 (C-$2^b$, C-$6^b$), 129.9 (C-$2^a$, C-$6^a$), 130.0 (C-$1^a$), 130.2 (C-$1^b$), 133.6 (C-9), 143.3 (C-4), 143.9 (C-2), 157.1 (C-$4^a$), 157.8 (C-41).

HRMS m/z=395.1732 found (calculated for $C_{24}H_{24}N_2O_2Na$ $[M+Na]^+$ requires 395.1730), 373.1912 found (calculated for $C_{24}H_{25}N_2O_2$ $[M+H]^+$ requires 373.1911).

Example 2

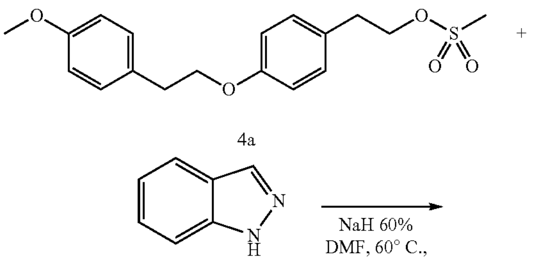

4a

5αb

-continued

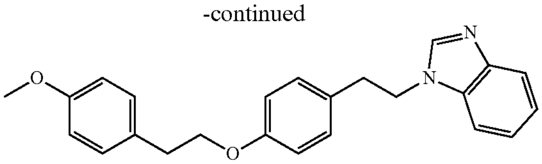

6αb (DAD4-573)

1-(4-(4-Methoxyphenethoxy)phenethyl)-1H-indazole (6αb). To a vigorous stirred (550 rpm) solution of indazole 5αb (0.571 mmol) in 1 ml of DMF was added sodium hydride 60% dispersion in mineral oil (0.023 g, 2 mmol) and the resulting suspension was stirred for 5 minutes. After addition of 4-(4-methoxyphenethoxy) phenethyl methanesulfonate 4a (0.286 mmol) in one portion, the reaction mixture was heated at 60° C. for 24 hours. After cooling down to room temperature, deionized water (10 ml) was added to the reaction mixture. Extraction was conducted with ethyl acetate (3×10 ml) and the collected extracts were transferred into a separating funnel. The organic phase was washed with brine (3×10 ml). After decantation, the organic layer was dried over anhydrous $MgSO_4$, filtered on a paper filter and the filtrate was concentrated in rotary evaporator under reduced pressure. The crude residue was submitted to purification by preparative chromatography (Combi Flash $R_f$ 200 psi apparatus with a DAD 200/360 nm detector) on pre-packed column of silica gel 60F-254 (Merck) using a stepwise gradient of cyclohexane/AcOEt (0-25%) for elution. Pooling for 60 minutes and elimination of the solvent in vacuo gave 14 mg (13% yield) of the pure desired compound 6αb as white powder. Mp=124-126° C.

$^{1}$H NMR (300 MHz, DMSO-$d_6$) δ=3.07 (t, J=7.2 Hz, 2H, $CH_2$, H-2'), 3.74 (s, 3H, $OCH_3$), 4.57 (t, J=7.2 Hz, 2H, $CH_2$, H-1'), 4.92 (s, 2H, $CH_2$, $OCH_2$), 6.82 (d, J=8.5 Hz, 2H, H-3$^b$, H-5$^b$, Ar), 6.92 (t, J=5.7 Hz, 2H, H-3$^a$, H-5$^a$, Ar), 7.14-6.99 (m, 3H, H-5, H-2$^b$, H-6$^b$, Ar), 7.31 (dd, J=12.2, 5.6 Hz, 3H, H-8, H-2$^a$, H-6$^a$, Ar), 7.52 (d, J=8.5 Hz, 1H, H-6, Ar), 7.72 (d, J=8.1 Hz, 1H, H-7, Ar), 8.04 (s, 1H, H-2, Ar).

$^{13}$C NMR (75 MHz, DMSO-$d_6$) δ=34.8 (C-2'), 49.8 (C-1'), 55.3 ($OCH_3$), 69.1 ($OCH_2$), 109.7 (C-5), 114.0 (C-3$^a$, C-5$^a$), 114.8 (C-3$^b$, C-5$^b$), 120.4 (C-8), 120.9 (C-6), 123.5 (C-1$^a$), 126.1 (C-7), 129.2 (C-1$^b$), 129.6 (C-2$^a$, C-6$^a$), 129.9 (C-2$^b$, C-6$^b$), 130.7 (C-9), 132.8 (C-3), 139.4 (C-4), 157.1 (C-4$^a$), 159.1 (C-4$^b$).

HRMS, m/z=395.1732 found (calculated for $C_{24}H_{24}N_2O_2Na$ $[M+Na]^+$ requires 395.1730), 373.1913 found (calculated for $C_{24}H_{25}N_2O_2$ $[M+H]^+$ requires 373.1911), 411.1473 found (calculated for $C_{24}H_{24}N_2O_2K$ $[M+K]^+$ requires 411.1469).

Example 3

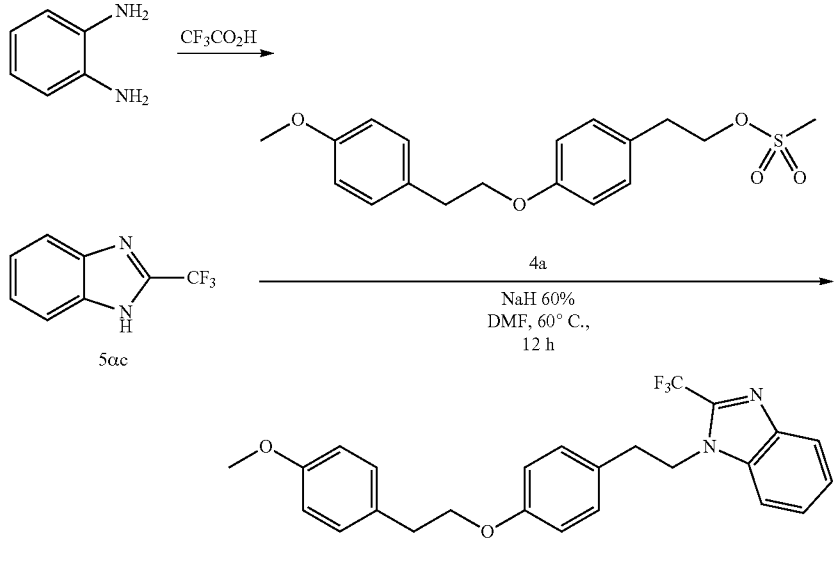

5αc

6αc (DAD4-546)

2-Trifluoromethyl-1H-benzo[d]imidazole (5αc). A mixture of ortho-phenylenediamine (1 g, 9.25 mmol) and trifluoroacetic acid TFA (1.581, 13.87 mmol, 1.5 eq.) was heated under reflux with vigorous magnetic stirring (500 rpm) for 24 hours. After cooling down to room temperature, the reaction mixture was transferred progressively with caution into a solution (100 ml) of saturated sodium carbonate. Extraction was conducted with ethyl acetate (3×50 ml) and the collected extracts were transferred into a separating funnel. The organic phase was washed with brine (3×50 ml). After decantation, the organic layer was dried over anhydrous $MgSO_4$, filtered on a paper filter and the filtrate was concentrated in a rotary evaporator under reduced pressure. The resulting solid was further dried under high vacuum ($10^{-3}$ Torr) and afforded the desired compound 5αc as brown powder in 97% yield. The compound 5αc is pure enough to be used later without further purification. Mp=213-218° C.

$^{1}$H NMR (300 MHz, DMSO-$d_6$) δ=7.38 (dd, J=6.2, 3.2 Hz, 2H, H-5, H-6, Ar), 7.72 (dt, J=6.7, 3.3 Hz, 2H, H-4, H-7, Ar), 12.53 (br s, 1H, NH).

$^{13}$C NMR (75 MHz, DMSO-$d_6$) δ=117.3 (C-4, C-7), 120.9 ($CF_3$), 124.1 (C-5, C-6), 139.8 (C-3a, C-7a), 140.3 (C-2).

$^{19}$F NMR (282 MHz, DMSO-$d_6$) δ=−62.8.

HRMS, m/z=209.0295 found (calculated for $C_8H_5N_2F_3Na$ $[M+Na]^+$ requires 209.0297).

1-(4-(4-Methoxyphenethoxy)phenethyl)-2-trifluoromethyl-1H-benzo[d]imidazole (6αc). To a vigorous stirred (550 rpm) solution of 2-trifluoromethyl benzimidazole 5αc (0.571 mmol) in 1 ml of DMF was added sodium hydride 60% dispersion in mineral oil (0.023 g, 2 mmol) and the resulting suspension was stirred for 5 minutes. After addition of 4-(4-methoxyphenethoxy)phenethyl methanesulfonate 4a (0.286 mmol) in one portion, the reaction mixture was heated at 60° C. for 24 hours. After cooling down to room temperature, deionised water (10 ml) was added to the reaction mixture. Extraction was conducted with ethyl acetate (3×10 ml) and the collected extracts were transferred into a separating funnel. The organic phase was washed with brine (3×10 ml). After decantation, the organic layer was dried over anhydrous $MgSO_4$, filtered on a paper filter and the filtrate was concentrated in rotary evaporator under reduced pressure. The crude residue was submitted to purification by preparative chromatography (Combi Flash $R_f$200 psi apparatus with a DAD 200/360 nm detector) on pre-packed column of silica gel 60F-254 (Merck) using a stepwise gradient of $CH_2Cl_2$/MeOH (0-1%) for elution. Pooling for 60 minutes and elimination of the solvent in vacuo gave 62.5 mg (50% yield) of the pure desired compound 6αc as viscous whitish oil.

$^1$H NMR (300 MHz, DMSO-$d_6$) δ=2.92 (t, J=6.9 Hz, 2H, $CH_2$, H-2"), 3.02 (t, J=7.5 Hz, 2H, $CH_2$, H-2'), 3.72 (s, 3H, $OCH_3$), 4.07 (t, J=6.9 Hz, 2H, $CH_2$, H-1'), 4.54 (t, J=7.5 Hz, 2H, $CH_2$, H-1"), 6.80 (d, J=8.6 Hz, 2H, H-$3^b$, H-$5^b$, Ar), 6.86 (d, J=8.6 Hz, 2H, H-$3^a$, H-$5^a$, Ar), 7.03 (d, J=8.6 Hz, 2H, H-$2^b$, H-$6^b$, Ar), 7.20 (d, J=8.6 Hz, 2H, H-$2^a$, H-$6^a$, Ar), 7.40 (dddd, J=19.9, 8.2, 7.2, 1.2 Hz, 2H, H-6, H-7, Ar), 7.70-7.76 (m, 1H, H-8, Ar), 7.78-7.84 (m, 1H, H-5, Ar).

$^{13}$C NMR (75 MHz, DMSO-$d_6$) δ=34.1 (C-2'), 34.6 (C-2"), 46.4 (C-1"), 55.1 ($OCH_3$), 68.4 (C-1'), 112.1 (C-5), 113.8 (C-$3^b$, C-$5^b$), 114.6 (C-$3^a$, C-$5^a$), 120.9 (C-8), 123.6 (C-6), 125.3 (C-7), 129.2 (C-$1^a$), 129.9 (C-$2^b$, C-$6^b$), 130.0 (C-$2^a$, C-$6^a$), 130.2 (C-$1^b$), 135.2 (C-9), 140.4 (C-4), 157.4 (C-$4^a$), 157.9 (C-$4^b$).

$^{19}$F NMR (282 MHz, DMSO-$d_6$) δ=−60.8.

HRMS m/z=463.1604 found (calculated for $C_{25}H_{23}N_2O_2F_3Na$ $[M+Na]^+$ requires 463.1604), 373.1912 found (calculated for $C_{25}H_{24}N_2O_2F_3$ $[M+H]^+$ requires 373.1911), 479.1341 found (calculated for $C_{25}H_{23}N_2O_2F_3K$ $[M+K]^+$ requires 479.1343).

Example 4

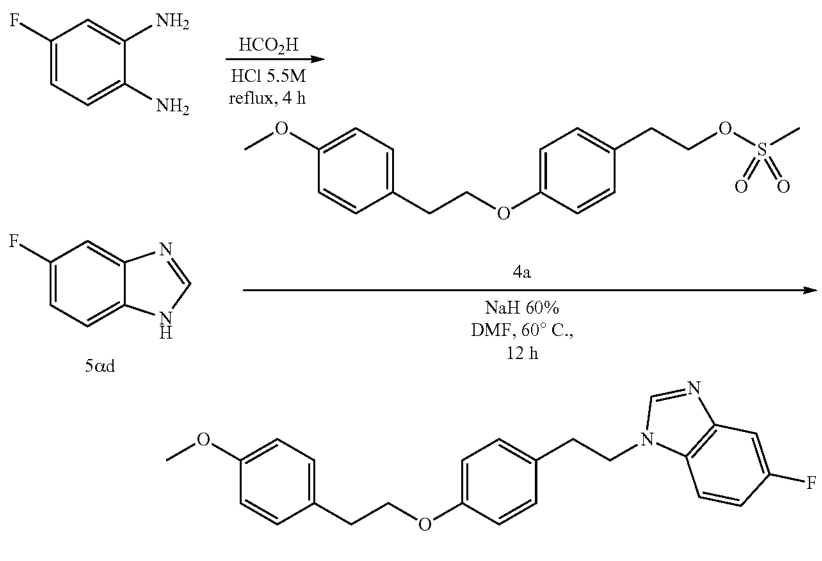

5αd

6αd (DAD4-547)

5-Fluoro-1H-benzo[d]imidazole (5αd). To a mixture of 4-fluoro ortho-phenylenediamine (0.5 g, 3.96 mmol) in 2.5 ml of a solution of 5.5 M HCl was added formic acid (0.273 g, 5.95 mmol, 1.5 eq.). The resulting reaction mixture was heated under reflux with vigorous magnetic stirring (500 rpm) for 4 hours. After cooling down to room temperature, 10 ml of 28-30% ammonia was added drop-wise with caution during 10 minutes in the reaction mixture. Extraction was conducted with ethyl acetate (4×50 ml) and the collected extracts were transferred into a separating funnel. The organic phase was washed with deionised water (4×50 ml). After decantation, the organic layer was dried over anhydrous $MgSO_4$, filtered on a paper filter and the filtrate was concentrated in a rotary evaporator under reduced pressure. To the resulting solid was added 10 ml of hexane and the suspension was triturated for 10 minutes. The insoluble material was recovered by filtration in a Buchner funnel (porosity No 4) and was further dried under high vacuum ($10^{-3}$ Torr), which gave the desired compound 5αd as purple powder in 89% yield. Mp=142-145° C.

$^1$H NMR (300 MHz, DMSO-$d_6$) δ=7.05 (td, J=9.3, 2.5 Hz, 1H, H-6, Ar), 7.39 (m, 1H, H-3, Ar), 7.58 (m, 1H, H-7, Ar), 8.25 (s, 1H, H-2, Ar), 12.53 (br s, 1H, NH).

$^{13}$C NMR (75 MHz, DMSO-$d_6$) δ=109.7 (C-4), 110.0 (C-6), 143.3 (C-3a), 157.3 (C-2), 159.6 (C-5).

$^{19}$F NMR (282 MHz, DMSO-$d_6$) δ=−121.4.

HRMS, m/z=137.0507 found (calculated for $C_7H_6N_2F$ $[M+H]^+$ requires 137.05095).

5-Fluoro-1-(4-(4-methoxyphenethoxy)phenethyl)-2-trifluoromethyl-1H-benzo [d]imidazole (6αd). To a vigorous stirred (550 rpm) solution of 5-fluoro-benzimidazole 5αd (0.571 mmol) in 1 ml of DMF was added sodium hydride 60% dispersion in mineral oil (0.023 g, 2 mmol) and the resulting suspension is stirred for 5 minutes. After addition of 4-(4-methoxyphenethoxy)phenethyl methanesulfonate 4a (0.286 mmol) in one portion, the reaction mixture was heated at 60° C. for 12 hours. After cooling down to room temperature, deionised water (10 ml) was added to the reaction mixture. Extraction was carried out with ethyl acetate (2×10 ml) and the collected extracts were transferred into a separating funnel. The organic phase was washed with brine (2×10 ml). After decantation, the organic layer was dried over anhydrous $MgSO_4$, filtered on a paper filter and the filtrate was concentrated in rotary evaporator under reduced pressure. The crude residue was submitted to purification by preparative chromatography (Combi Flash $R_f$ 200 psi apparatus with a DAD 200/360 nm detector) on pre-packed column of silica gel 60F-254 (Merck) using a stepwise gradient of $CH_2Cl_2$/MeOH (0-0.5%) for elution. Pooling for 60 minutes and elimination of the solvent in vacuo gave 63 mg (56% yield) of the pure desired compound 6αd as white powder. Mp=121-123° C.

$^1$H NMR (300 MHz, DMSO-$d_6$) δ=2.93 (t, J=6.9 Hz, 2H, $CH_2$, H-2"),), 3.02 (td, J=7.2, 2.8 Hz, 2H, $CH_2$, H-2'), 3.72 (s, 3H, $OCH_3$), 4.08 (t, J=6.9 Hz, 2H, $CH_2$, H-1'), 4.43 (q, J=7.4 Hz, 2H, $CH_2$, H-1"), 6.77-6.83 (m, 2H, H-3$^b$, H-5$^b$, Ar), 6.86 (d, J=8.6 Hz, 2H, 2H, H-3$^a$, H-5$^a$, Ar), 6.98-7.15 (m, 3H, H-7, H-2$^b$, H-6$^b$, Ar), 7.21 (d, J=8.6 Hz, 2H, H-2$^a$, H-6$^a$, Ar), 7.46 (ddd, J=28.2, 9.6, 2.5 Hz, 1H, H-8, Ar), 7.62 (dt, J=8.8, 5.1 Hz, 1H, H-5, Ar), 8.07 (d, J=10.7 Hz, 1H, H-2, Ar).

$^{13}$C NMR (75 MHz, DMSO-$d_6$) δ=34.0 (C-2'), 34.5 (d, J=8.8 Hz) (C-2"), 45.8 (d, J=10.8 Hz) (C-1"), 55.0 ($OCH_3$), 68.3 (C-1'), 97.1, 97.4, 104.6, 104.9, 109.5, 109.7, 110.2, 110.5, 111.3, 111.4, 113.7 (C-3$^b$, C-5$^b$), 114.4 (C-3$^a$, C-5$^a$), 120.1, 120.2, 129.7 (C-2$^b$), 129.8 (C-6$^b$), 129.9 (C-2$^a$, C-6$^a$), 129.9 (C-1$^a$), 130.2 (C-1$^b$), 139.7 (C-9), 145.2 (d, J=69.5 Hz) (C-2), 159.7 (d, J=41.9 Hz) (C-6), 157.1 (C-4$^a$), 157.8 (C-4$^b$).

$^{19}$F NMR (282 MHz, DMSO-$d_6$) δ=−122.0 (td, J=9.7, 4.8 Hz), −119.8 (td, J=9.6, 5.0 Hz).

HRMS m/z=413.1639 found (calculated for $C_{24}H_{23}N_2O_2FNa$ $[M+Na]^+$ requires 413.1636), 391.1819 found (calculated for $C_{24}H_{24}N_2O_2F$ $[M+H]^+$ requires 391.1816), 429.1379 found (calculated for $C_{24}H_{23}N_2O_2FK$ $[M+K]^+$ requires 429.1375).

Example 5

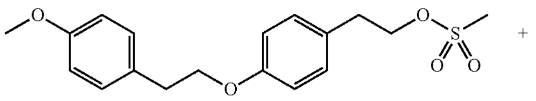

4a

-continued

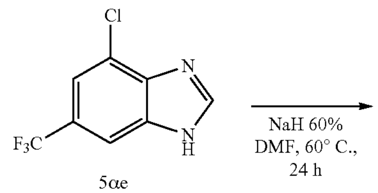

5αe

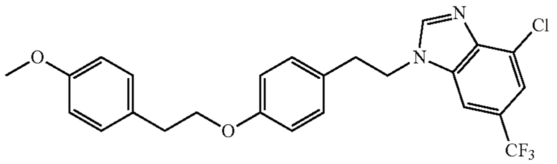

6αe (DAD4-548)

4-Chloro-1-(4-(4-methoxyphenethoxy)phenethyl)-6-(trifluoromethyl)-1H-benzo[d]imidazole (6αe). Compound 6αe was prepared from 4-(4-methoxyphenethoxy)phenethyl methanesulfonate 4a and 4-chloro-5-trifluoromethylbenzimidazole 5αe in 25% yield (0.115 g) according to the procedure used for the preparation of 6αa described in Example 1. Mp=119-121° C.

$^1$H NMR (300 MHz, DMSO-$d_6$) δ=2.91 (t, J=6.8 Hz, 2H, $CH_2$, H-2"), 3.04 (t, J=6.9 Hz, 2H, $CH_2$, H-2'), 3.72 (s, 3H, $OCH_3$), 4.05 (t, J=6.9 Hz, 2H, $CH_2$, H-1'), 4.58 (t, J=6.9 Hz, 2H, $CH_2$, H-1"), 6.77 (d, J=8.6 Hz, 2H, H-3$^b$, H-5$^b$, Ar), 6.86 (d, J=8.6 Hz, 2H, H-3$^a$, H-5$^a$, Ar), 7.02 (d, J=8.6 Hz, 2H, H-2$^b$, H-6$^b$, Ar), 7.20 (d, J=8.6 Hz, 2H, H-2$^a$, H-6$^a$, Ar), 7.54-7.63 (m, 1H, H-8, Ar), 7.92 (dd, J=1.6, 0.8 Hz, 1H, H-5, Ar), 8.37 (s, 1H, H-2, Ar).

$^{19}$F NMR (282 MHz, DMSO-$d_6$) δ=−51.0.

HRMS m/z=497.1220 found (calculated for $C_{25}H_{22}N_2O_2F_3{}^{35}Cl$ Na $[M+Na]^+$ requires 497.1214), 475.1397 found (calculated for $C_{25}H_{23}N_2O_2F_3{}^{35}Cl$ $[M+H]^+$ requires 475.1395), 513.0959 found (calculated for $C_{25}H_{22}N_2O_2F_3{}^{35}ClK$ $[M+K]^+$ requires 513.0954).

Example 6

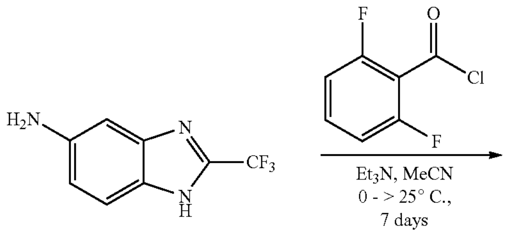

5αf

-continued

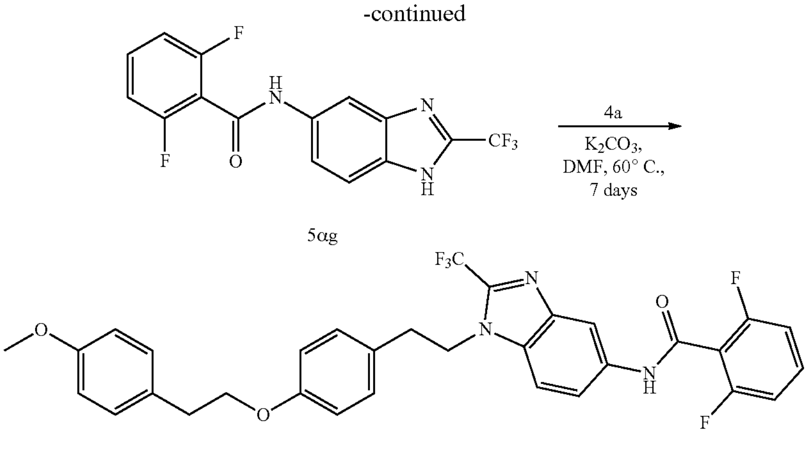

5αg

6αf 2,6-Difluoro-N-(2-(trifluoromethyl)-1H-benzo[d]imidazol-5-yl)benzamide (5αg). To a solution of 5-amino-2-trifluoromethyl benzimidazole 5αf (0.5 g, 2.48 mmol) in 2 ml of dry acetonitrile (MeCN) under vigorous magnetic stirring (500 rpm) and cooled at 0° C. (ice bath) was added drop-wise triethylamine TEA (4.97 mmol, 2 eq.), then stirring was pursued during 10 minutes at 0° C. To the mixture was added drop-wise a solution of 2,6-diflurobenzoyl chloride (2.48 mml, 1 eq.) in 0.5 ml of dry acetonitrile for 3 minutes. The resulting reaction mixture was mixed at room temperature for 7 days (monitored by thin layer chromatography on 0.2 mm plates of silica gel 60 F254 Merck using $CH_2Cl_2$/MeOH 9:1 v/v as eluent). Solvent of the reaction mixture was eliminated in rotary evaporator under reduced pressure and to the crude residue was poured successively 10 ml of deionised water and 20 ml of ethyl acetate. The resulting mixture was transferred into a separating funnel and after separation of the organic layer; extraction from water layer was pursued with 3×75 ml of AcOEt. The collected organic layers were dried over magnesium sulfate and filtered on paper filter. The filtrate was concentrated in vacuo and afforded the desired compound 5αg in 78% yield as brown powder. The compound 5αg is pure enough to be used later without further purification. Mp=159-162° C.

$^1H$ NMR (300 MHz, DMSO-$d_6$) δ=7.28 (t, J=8.0 Hz, 2H, H-3", H5", Ar), 7.59 (m, 2H, H-6, H-7, Ar), 7.75 (d, J=8.8 Hz, 1H, H-4", Ar), 8.32 (d, J=1.9 Hz, 1H, H-4, Ar), 10.99 (br s, 1H, NH).

$^{13}C$ NMR (75 MHz, DMSO-$d_6$) δ=112.0 (C-4, Ar), 112.3 (C-3", C-5", Ar), 115.2 (C-7, Ar), 115.5 (C-1", Ar), 115.8 ($CF_3$), 117.3 (C-6, Ar), 120.8 (C-4", Ar), 132.2 (C-5, Ar), 135.4 (C-$7^a$, Ar), 140.6 (C-$3^a$, Ar), 157.3 (C═O, C-2), 158.2 (C-2", C-6", Ar), 160.5 (C═N, C-2, Ar).

$^{19}F$ NMR (282 MHz, DMSO-$d_6$) δ=−114.0, −62.7 ($CF_3$).

HRMS, m/z=364.0481 found (calculated for $C_{15}H_8N_3F_5Na$ $[M+Na]^+$ requires 364.0480).

N-(1-(4-(4-Methoxyphenethoxy)phenethyl)-2-(trifluoromethyl)-1H-benzo[d]imidazol-5-yl)-2,6-difluorobenzamide (6αf). Compound 6αf was prepared from 2,6-difluoro-N-(2-(trifluoromethyl)-1H-benzo[d]imidazol-5-yl) benzamide 5αg (0.176 g, 0.52 mmol, 1.45 eq.) and 4-(4-methoxyphenethoxy)phenethyl methanesulfonate 4a (0.125 g, 0.356 mmol, 1 eq.) in 26% yield according to the procedure used for the preparation of 6αc described in Example 3. Mp=69-70° C.

$^1H$ NMR (300 MHz, DMSO-$d_6$) δ=2.93 (tt, J=7.0, 2.9 Hz, 2H, $CH_2$, H-2"), 3.04 (m, 2H, $CH_2$, H-2'), 3.72 (s, 3H, $OCH_3$), 4.08 (tt, J=6.9, 2.5 Hz, 2H, $CH_2$, H-1'), 4.53 (q, J=7.4 Hz, 2H, $CH_2$, H-1"), 6.84 (m, 4H, H-$3^a$, H-$5^a$, H-$3^b$, H-$5^b$, Ar), 7.02 (m, 2H, H-3', H-5', Ar), 7.24 (m, 4H, H-$2^a$, H-$6^a$, H-$2^b$, H-$6^b$, Ar), 7.64 (m, 3H, H-6, H-7, H-$4^c$, Ar), 8.28 (dd, J=16.4, 1.8 Hz, 1H, H-4, Ar), 10.97 (d, J=35.8 Hz, 1H, NH).

$^{13}C$ NMR (75 MHz, DMSO-$d_6$) δ=34.1 (C-2'), 34.6 (C-2"), 46.6 (C-1'), 55.1 ($OCH_3$), 68.4 (C-1"), 101.9 (C-4, Ar), 110.7 (C-$3^c$, C-$5^c$, Ar), 112.1 ($CF_3$), 112.5 (C-$1^c$, Ar), 113.8 (C-$3^a$, C-$5^a$, Ar), 114.6 (C-$3^b$, C-$5^b$, Ar), 114.7 (C-7, Ar), 118.6 (C-6, Ar), 129.1 (C-$2^b$, C-$6^b$, Ar), 129.8 (C-$2^a$, C-$6^a$, Ar), 130.0 (C-$7^a$, Ar), 130.2 (C-$1^a$, Ar), 134.8 (C-5, Ar), 136.3 (C-$4^c$, Ar), 137.2 (C-$3^a$, Ar), 140.5 (C-2, Ar), 157.4 (C-$2^c$, C-$6^c$, Ar), 157.9, 158.2, 158.4, 160.6 (C═O, C-2"').

$^{19}F$ NMR (282 MHz, DMSO-$d_6$) δ=−114.0, −113.9, −60.7 ($CF_3$).

HRMS, m/z=618.1786 found (calculated for $C_{32}H_{26}N_3F_5Na$ $[M+Na]^+$ requires 618.17865).

Example 7

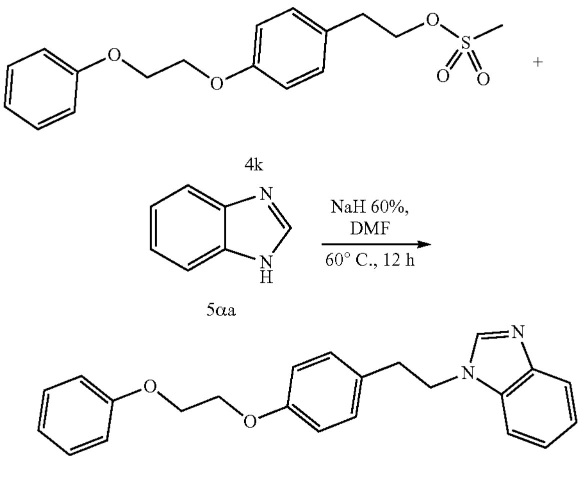

4k

5αa

6αk 1-(4-(2-Phenoxyethoxy)phenethyl)-1H-benzo[d]imidazole (6αk). Compound 6αk was prepared from 4-(2-phenoxyethoxy)phenethyl methanesulfonate 4k and benzimidazole 5αa in 34% yield (0.125 g) according to the procedure used for the preparation of 6αa described in Example 1. Mp=141-143° C.

$^1$H NMR (300 MHz, DMSO-d$_6$) δ=3.05 (t, J=7.2 Hz, 2H, CH$_2$, H-2'), 4.35-4.18 (m, 4.H, CH$_2$, H-1", H-2"), 4.45 (t, J=7.2 Hz, 2H, CH$_2$, H-1'), 7.01-6.81 (m, 5H, H-3$^b$, H-4$^b$, H-5$^b$, H-6, H-7, Ar), 7.08 (d, J=8.6 Hz, 2H, H-5, H-8, Ar), 7.24 (dddd, J=29.2, 27.6, 13.7, 7.5 Hz, 4H, H-3$^a$, H-5$^a$, H-2$^b$, H-6$^b$, Ar), 7.67-7.58 (m, 2H, H-2$^a$, H-6$^a$, Ar), 8.02 (s, 1H, H-2, Ar).

$^{13}$C NMR (75 MHz, DMSO-d$_6$) δ=34.5 (C-2'), 45.6 (C-1'), 66.2 (C-2"), 66.25 (C-1"), 110.4 (C-5), 114.4 (C-3$^b$, C-5$^b$), 114.5 (C-3$^a$, C-5$^a$), 119.3 (C-8), 120.7 (C-6), 121.3 (C-7), 122.1 (C-4$^b$), 129.5 (C-2$^b$, C-6$^b$), 129.8 (C-2$^a$, C-6$^a$), 130.3 (C-1$^a$), 133.6 (C-4), 143.4 (C-9), 143.9 (C-2), 157.0 (C-1$^b$), 158.3 (C-4$^a$).

HRMS m/z=381.1569 found (calculated for $C_{23}H_{22}N_2O_2Na$ [M+Na]$^+$ requires 381.1573), 359.1753 found (calculated for $C_{23}H_{23}N_2O_2$ [M+H]$^+$ requires 359.1754).

Example 8

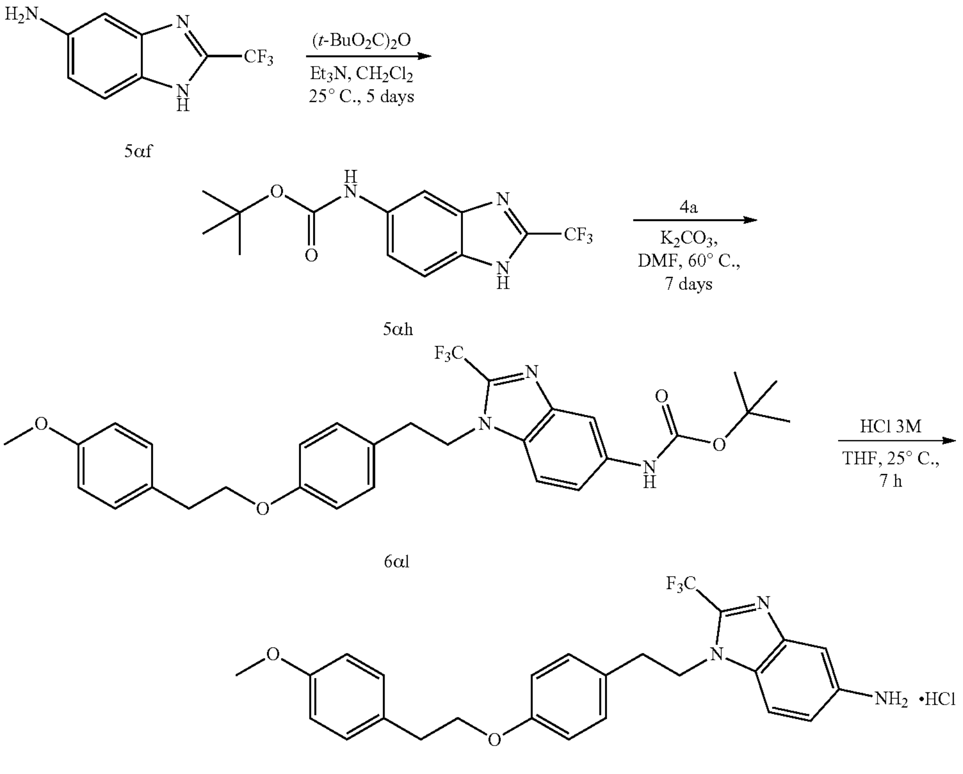

5αf

5αh

6αl

6αm tert-Butyl 2-(Trifluoromethyl)-1H-benzo[d]imidazol-5-ylcarbamate (5αd). To a solution under vigorous magnetic stirring (500 rpm) of 5-amino-2-(trifluoromethyl)benzimidazole 5αf (0.470 g, 2.34 mmol) in 8 ml of methylenechloride was added dropwise triethylamine TEA (0.2369 g, 326 ml, 2.34 mmol) followed by di-tert-butylcarbonate (t-BuO$_2$C)$_2$O (0.510 g, 538 ml, 2.34 mmol) and stirring was pursued at 30° C. during 5 days (monitored by thin layer chromatography using 0.2 mm plates of silica gel 60-F254 Merck). The reaction mixture was concentrated using a rotary evaporator under reduced pressure and the crude residue was submitted to purification by chromatography (Combi Flash R$_f$ 200 psi apparatus with a DAD 200/360 nm detector) on pre-packed column of silica gel 60 F-254 (Merck) using a stepwise gradient of cyclohexane/AcOEt (0-50%) for elution. Pooling for 60 minutes and elimination of the solvent in vacuo gave the pure desired compound 5αh as whitish powder in 84% yield. Mp=210-212° C.

$^1$H NMR (300 MHz, DMSO-d$_6$) δ=1.50 (s, 9H, (CH$_3$)$_3$), 7.36 (d, J=8.9 Hz, 1H, H-6), 7.62 (d, J=8.8 Hz, 1H, H-7), 7.94 (d, J=1.9 Hz, 1H, H-4), 9.52 (s, 1H, H-1'), 13.70 (s, 1H, H-1).

$^{13}$C NMR (75 MHz, DMSO-d$_6$) δ=28.2 (CH$_3$)$_3$), 79.2 (C-4"), 117.3 (C-7), 120.9 (CF$_3$), 152.9 (C-2").

$^{19}$F NMR (282 MHz, DMSO-d$_6$) δ=−62.6.

HRMS, m/z=324.0934 found (calculated for $C_{13}H_{15}N_3O_2F_5Na$ [M+Na]$^+$ requires 324.0930).

tert-Butyl 1-(4-(4-methoxyphenethoxy)phenethyl)-2-(trifluoromethyl)-1H-benzo [d]imidazol-5-ylcarbamate (6αd). To a solution of tert-butyl 2-(trifluoromethyl)-1H-benzo[d]imidazol-5-ylcarbamate 5αh (1.2 mmol) in 3.5 ml of dry DMF was added portion-wise potassium hydrogenocarbonate NaHCO$_3$ (3.6 mmol, 3 eq.) and stirring was pursued for 30 minutes. After addition of 4-(4-methoxyphenethoxy) phenethyl methanesulfonate 4a (1.2 mmol), the mixture was heated at 60° C. for 3 days (monitored by thin layer chromatography using 0.2 mm plates of silica gel 60-F254 Merck). After cooling down to room temperature, 35 ml of deionised water was poured in the reaction mixture and the resulting solution was transferred in a separating funnel. Extraction was carried out using ethyl acetate (4×25 ml) and the collected extracts were washed successively with deionised water (4×25 ml), brine (2×45 ml); dried over anhydrous $MgSO_4$ and filtered on a paper filter. The filtrate was concentrated using a rotary evaporator under reduced pressure and the crude residue was submitted to purification by chromatography (Combi Flash $R_f$ 200 psi apparatus with a DAD 200/360 nm detector) on pre-packed column of silica gel 60 F-254 (Merck) using a stepwise gradient of cyclohexane/AcOEt (0-50%) for elution. Pooling for 60 minutes and elimination of the solvent in vacuo gave the pure desired compound 6αl as beige gummy paste in 73% yield. Mp<50° C.

$^1$H NMR (300 MHz, DMSO-$d_6$) δ=1.50 (d, J=5.1 Hz, 9H, $(CH_3)_3$), 2.93 (m, 2H, $CH_2$, H-2"), 3.01 (t, J=7.4 Hz, 2H, $CH_2$, H-2'), 3.73 (s, 3H, $OCH_3$), 4.08 (t, J=6.9 Hz, 2H, $CH_2$, H-1'), 4.45 (t, J=7.4 Hz, 2H, $CH_2$, H-1"), 6.84 (m, 4H, H-3$^a$, H-5$^a$, H-3$^b$, H-5$^b$, Ar), 7.01 (dd, J=8.6, 4.2 Hz, 2H, H-2$^a$, H-6$^a$, Ar), 7.22 (m, 2H, H-2$^b$, H-6$^b$), 7.35 (dd, J=8.9, 1.9 Hz, 1H, H-6, Ar), 7.68 (d, J=8.9 Hz, 1H, H-7, Ar), 7.93 (d, J=15.8 Hz, 1H, H-4), 9.57 (s, 1H, NH).

$^{13}$C NMR (75 MHz, DMSO-$d_6$) δ=28.1 $(CH_3)_3$, 34.0 (C-2'), 34.6 (C-2"), 46.2 (C-1'), 55.0 ($OCH_3$), 68.4 (C-1"), 79.3 (CO), 111.8 (C-4), 113.7 ($CF_3$), 114.5 (C-3$^b$, C-5$^b$), 114.6 (C-3$^a$, C-5$^a$), 116.1 (C-7), 120.9 (C-6), 129.6 (C-2$^a$, C-1$^a$), 129.8 (C-7$^a$), 129.9 (C-1$^a$), 130.1 (C-1$^b$), 135.4 (C-5), 135.9 (C-3$^a$), 137.5 (C-2), 152.8 (C═O), 157.3 (C-4$^a$) 157.8 (C-4$^b$).

$^{19}$F NMR (282 MHz, DMSO-$d_6$) δ=−60.6.

HRMS, m/z=578.2235 found (calculated for $C_{30}H_{32}N_3O_4F_3Na$ $[M+Na]^+$ requires 578.2237).

5-Amino-1-(4-(4-methoxyphenethoxy)phenethyl)-6-(trifluoromethyl)-1H-benzo [d]imidazole hydrochloride (6αm). To a solution of tert-butyl 1-(4-(4-methoxy phenethoxy) phenethyl)-2-(trifluoromethyl)-1H-benzo[d]imidazol-5-yl-carbamate 6αl (0.155 g, 0.277 mmol) in 2.1 ml of dioxane under vigorous magnetic stirring (500 rpm) was added drop-wise 1.1 ml of a solution 6M HCl (24 eq.) at room temperature. Stirring was pursued for 3 days (monitored by thin layer chromatography using 0.2 mm plates of silica gel 60-F254 Merck). The reaction mixture was concentrated using a rotary evaporator under reduced pressure. To the crude residue was poured 5 ml of dry diethylether $Et_2O$ and the suspension was triturated for 10 minutes to obtain a fine powder. The insoluble material was recovered by filtration in a Buchner funnel (porosity No 4), washed with $Et_2O$ (2×5 ml) and was further dried under high vacuum ($10^{-3}$ Torr), which gave the desired hydrochloride salt 6αm as whitish powder in 26% yield. Mp=210-212° C.

$^1$H NMR (300 MHz, DMSO-$d_6$) δ=2.93 (td, J=7.0, 2.1 Hz, 2H), 3.03 (q, J=7.0 Hz, 2H), 3.72 (s, 3H), 4.08 (td, J=6.9, 4.7 Hz, 2H), 4.54 (dt, J=24.4, 7.5 Hz, 2H), 6.85 (m, 4H), 7.04 (t, J=8.2 Hz, 2H), 7.24 (ddd, J=9.7, 8.6, 1.4 Hz, 2H), 7.50 (m, 1H), 7.85 (m, 1H).

$^{13}$C NMR (75 MHz, DMSO-$d_6$) δ=34.0 (C-2"), 34.5 (C-2'), 46.4 (C-1'), 55.0 ($OCH_3$), 68.4 (C-1"), 103.7 (C-4), 113.4 ($CF_3$), 113.7 (C-3$^a$, C-5$^a$), 114.6 (C-3$^b$, C-5$^b$), 118.0 (C-7), 120.5 (C-6), 121.9 (C-7$^a$), 128.1 (C-1$^a$), 129.0 (C-1$^b$), 129.7 (C-2$^b$, C-6$^b$), 129.9 (C-2$^a$. C-6$^a$), 130.1 (C-3$^a$), 137.9 (C-2), 140.3 (C-5), 157.3 (C-4$^a$), 157.8 (C-4$^b$).

$^{19}$F NMR (282 MHz, DMSO-$d_6$) δ=−61.0.

Example 9

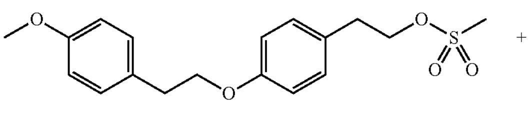

4a

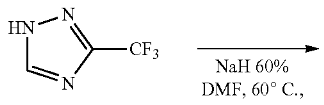

5βa

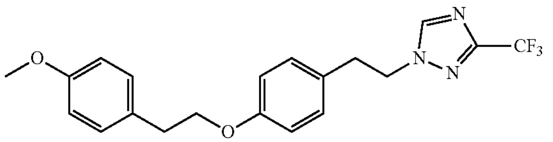

6βa (DAD3-478)

1-(4-(4-Methoxyphenethoxy)phenethyl)-3-(trifluoromethyl)-1H-1,2,4-triazole (6βa). Compound 60a was prepared from 4-(4-methoxyphenethoxy)phenethyl methanesulfonate 4a and 3-(trifluoromethyl)-1H-1,2,4-triazole 5βa in 44% yield (0.171 g) according to the procedure used for the preparation of 6αa described in Example 1. Mp=83-85° C.

$^1$H NMR (300 MHz, DMSO-$d_6$) δ=2.93 (t, J=6.9 Hz, 2H, $CH_2$, H-2'), 3.06 (t, J=7.2 Hz, 2H, $CH_2$, H-2"), 3.72 (s, 3H, $OCH_3$), 4.08 (t, J=6.9 Hz, 2H, $CH_2$, H-1'), 4.48 (t, J=7.2 Hz, 2H, $CH_2$, H-1"), 6.84 (dd, J=10.4, 8.6 Hz, 4H, H-3$^a$, H-5$^a$, H-3$^b$, H-5$^b$, Ar), 7.05 (d, J=8.6 Hz, 2H, H-2$^b$, H-6$^b$, Ar), 7.21 (d, J=8.6 Hz, 2H, H-2$^a$, H-6$^a$, Ar), 8.63 (d, J=0.9 Hz, 1H, H-5).

$^{13}$C NMR (75 MHz, DMSO-$d_6$) δ=34.1 (C-2'), 34.1 (C-2"), 51.0 (C-1"), 55.0 ($OCH_3$), 68.3 (C-1'), 113.7 (C-3$^a$, C-5$^a$), 114.5 (C-3$^b$, C-5$^b$), 129.1 (C-1$^a$), 129.6 (C-2$^b$, C-6$^b$), 129.9 (C-2$^a$, C-6$^a$), 130.2 (C-1$^b$), 146.4 (C-5), 157.2 (C-4$^a$), 157.8 (C-41)

$^{19}$F NMR (282 MHz, DMSO-$d_6$) δ=−63.8.

HRMS m/z=428.1554 found (calculated for $C_{21}H_{22}N_3O_2F_3Na$ $[M+Na]^+$ requires 428.1556).

Example 10

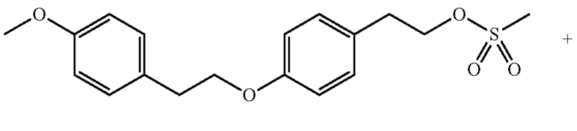

4a

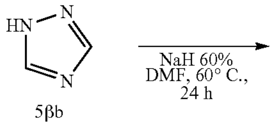

5βb

-continued

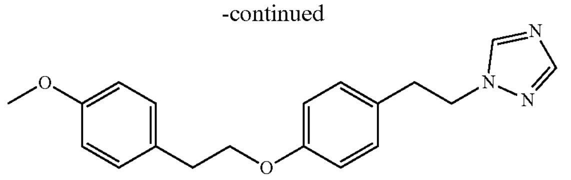

6βb (DAD3-469)

1-(4-(4-Methoxyphenethoxy)phenethyl)-1H-1,2,4-triazole (6βb). Compound 6βb was prepared from 4-(4-methoxyphenethoxy)phenethyl methanesulfonate 4a and 1H-1,2,4-triazole 5βb in 31% yield (0.102 g) according to the procedure used for the preparation of 6αa described in Example 1. Mp<50° C.

$^{1}$H NMR (300 MHz, DMSO-$d_6$) δ=2.93 (t, J=6.9 Hz, 2H, $CH_2$, H-2"), 3.02 (t, J=7.1 Hz, 2H, $CH_2$, H-2'), 3.72 (s, 3H, $OCH_3$), 4.08 (t, J=6.9 Hz, 2H, $CH_2$, H-1'), 4.36 (t, J=7.1 Hz, 2H, $CH_2$, H-1"), 6.81 (d, J=8.6 Hz, 2H, H-$3^a$, H-$5^a$, Ar), 6.86 (d, J=8.6 Hz, 2H, H-$3^b$, H-$5^b$, Ar), 7.02 (d, J=8.6 Hz, 2H, H-$2^b$, H-$6^b$, Ar), 7.22 (d, J=8.6 Hz, 2H, H-$2^a$, H-$6^a$, Ar), 7.94 (s, H-5, Ar), 8.29 (s, H-3, Ar).

$^{13}$C NMR (75 MHz, DMSO-$d_6$) δ=34.4 (C-2"), 34.7 (C-2'), 50.4 (C-1'), 55.4 ($OCH_3$), 68.7 (C-1"), 114.1 (C-$3^a$, C-$5^a$), 114.8 (C-$3^b$, C-$5^b$), 129.9 (C-$1^a$), 130.0 (C-$2^a$, C-$6^a$), 130.3 (C-$2^b$, C-$6^b$), 130.7 (C-$1^b$), 144.3 (C-5), 151.5 (C-3), 157.4 (C-$4^a$), 158.1 (C-$4^b$).

HRMS m/z=346.1528 found (calculated for $C_{19}H_{21}N_3O_2Na$ $[M+Na]^+$ requires 346.1526), 324.1706 found (calculated for $C_{19}H_{22}N_3O_2$ $[M+H]^+$ requires 324.1707).

Example 11

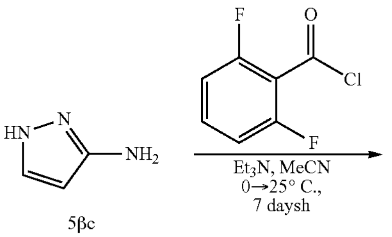

5βc

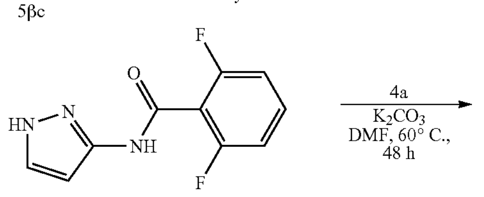

5βd

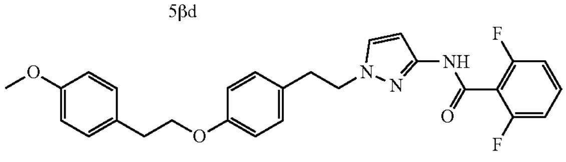

6βc 2,6-Difluoro-N-(1H-pyrazol-3-yl)benzamide (5βd). To a vigorous stirred (500 rpm) solution of 3-aminopyrazole 5βc (0.5 g, 6.017 mmol) in 4.17 ml of dry acetonitrile cooled at 0° C. (ice bath) was added drop-wise triethylamine TEA (1.63 ml, 1.21 g, 12.034 mmol, 2 eq.) for 10 minutes. Stirring was pursued at 0° C. for 10 minutes then, a solution of 2,6-difluorobenzoyl chloride (6.017 mmol, 1 eq.) in 1.67 ml of dry MeCN was added drop-wise for 3 minutes. Stirring was pursued at room temperature for 24 hours (monitored by thin layer chromatography on 0.2 mm plates of silica gel 60-F254 Merck using $CH_2Cl_2$/MeOH 9:1 v/v as eluent). The reaction mixture was concentrated using a rotary evaporator under reduced pressure and to the crude residue was added 2 ml of deionised and 4 ml of ethyl acetate. The resulting solution was transferred into a separating funnel and the two phases were separated after decantation. The aqueous phase was washed with AcOEt (2×4 ml). The collected organic extracts were successively washed with deionised water (3×15 ml), dried over $MgSO_4$ and filtered on a paper filter. The filtrate was concentrated in rotary evaporator under reduced pressure that afforded to a clear yellow viscous paste. This paste was triturated in methylene chloride to produce fine divided powder, which was washed with 15 ml of deionised water. The white powder was recovered by filtration on Buchner funnel and further dried under high vacuum ($10^{-2}$ Torr). Mp=76-78° C.

$^{1}$H NMR (300 MHz, DMSO-$d_6$) δ=6.63 (t, J=2.1 Hz, 1H, =CH, H-4), 7.20 (t, J=8.0 Hz, 2H, H-2'", H-6'"), 7.55 (tt, J=8.4, 6.6 Hz, 1H, H-4'"), 7.70 (t, J=1.8 Hz, 1H, =CH, H-5), 11.24 (sl, 1H, H-1"), 12.50 (br s, 1H, H-1).

$^{13}$C NMR (75 MHz, DMSO-$d_6$) δ=96.5 (=CH, C-4), 112.1 (C-3", C-5", Ar), 115.3 (C-1'", Ar), 128.9 (=CH, C-5), 131.9 (C-4", Ar), 146.5 (C=N, C-3), 157.4 (C-2", C-6", Ar), 160.6 (C-1", Ar).

$^{19}$F NMR (282 MHz, DMSO-$d_6$) δ=−114.1, −114.0.

HRMS, m/z=246.0446 found (calculated for $C_{10}H_7N_3OF_2Na$ $[M+Na]^+$ requires 246.0449).

N-(1-(4-(4-methoxyphenethoxy)phenethyl)-1H-pyrazol-3-yl)-2,6-difluoro benzamide (6βc). Compound 6βc was prepared from 4-(4-methoxyphenethoxy) phenethyl methanesulfonate 4a (0.07, 0.2 mmol) and 2,6-difluoro-N-(1H-pyrazol-3-yl)benzamide 5βd (0.09 g, 0.4 mmol, 2 eq.) in 21% yield as white powder according to the procedure used for the preparation of 6αf described in Example 6. Mp=210-212° C.

$^{1}$H NMR (300 MHz, DMSO-$d_6$) δ=2.97 (dt, J=17.9, 7.0 Hz, 4H, $CH_2$, H-2', H-2"), 3.73 (s, 3H, $OCH_3$), 4.10 (t, J=6.9 Hz, 2H, $CH_2$, H-1'), 4.22 (t, J=6.8 Hz, 2H, $CH_2$, H-1"), 6.52 (d, J=2.3 Hz, 1H, HC=, H-4, Ar), 6.86 (m, 4H, H-$3^a$, H-$5^a$, H-$3^b$, H-$5^b$, Ar), 7.06 (d, J=8.6 Hz, 2H, H-$2^b$, H-$6^b$, Ar), 7.20 (m, 4H, H-$2^a$, H-$6^a$, H-3c, H-5c, Ar), 7.54 (d, J=2.4 Hz, 2H, HC=, H-5, H-4c Ar), 11.23 (br s, 1H, NH).

$^{13}$C NMR (75 MHz, DMSO-$d_6$) δ=34.1 (C-2'), 35.0 (C-2"), 52.6 (C-1'), 55.0 ($OCH_3$), 68.3 (C-1"), 96.6 (C=, C-4, Ar), 111.7 (C-$3^c$, C-$5^c$, Ar), 112.0 (C-$1^c$, Ar), 113.7 (C-$3^a$, C-$5^a$, Ar), 114.4 (C-$3^b$, C-$5^b$, Ar), 129.6 (C-$2^a$, C-$6^a$, Ar, C=, C-5, Ar), 129.9 (C-$2^b$, C-$6^b$, Ar), 130.1 (C-$1^a$, Ar), 130.2 (C-$1^b$, Ar), 130.5 (C-$4^c$, Ar), 131.8 (C=N, C-3, Ar), 146.1 (C-$4^a$, Ar), 157.0 (C-$4^b$, Ar), 157.3 (C-$2^c$, C-$6^c$, Ar), 157.8, 160.6 (C=O, C-2N')

$^{19}$F NMR (282 MHz, DMSO-$d_6$) δ=−114.1, −113.9.

HRMS, m/z=500.1758 found (calculated for $C_{27}H_{25}N_3O_3F_2Na$ $[M+Na]^+$ requires 500.1756).

Example 12

General procedure for O-alkylation of 2-(4-hydroxyphenyl)ethanol 1a, 2-(3-hydroxyphenyl)ethanol 1b or 2-(2-hydroxyphenyl)ethanol 1c for preparation of compounds 3. To a solution of 2-(4-hydrophenyl)ethanol 1a or 2-(3-hydroxyphenyl)ethanol 1b or 2-(2-hydroxyphenyl)ethanol 1c (3.75 g, 27.14 mmol) in 15 ml of dry DMF under vigorous magnetic stirring (550 rpm) was added portion-wise 11.25 g of potassium carbonate $K_2CO_3$ (8.43 mmol, 3 equiv.) at room temperature. After 30 minutes, alkyl halide 2 (27.14 mmol) was added drop-wise during 30 minutes at 25° C., then stirring is pursued for 24 hours (monitored by thin layer chromatography with 0.2 mm plates of silica gel 60-F254 Merck using $CH_2Cl_2$/MeOH 95:5 v/v as eluent). Deionised water (150 ml) was added directly to the crude reaction mixture and stirring was maintained until complete precipitation. The insoluble material was recovered by filtration in a Buchner funnel (porosity No 4) and the precipitate was washed successively with deionized water (3×50 ml), then hexane (2×50 ml). The resulting precipitate was stirred in hexane (50 ml) and the suspension was concentrated under reduced using a rotary evaporator; the resulting solid was further dried under high vacuum ($10^{-3}$ Torr) and afforded the desired compound 3. The compound 3 was used later without further purification.

2-(4-(3-Phenylpropoxy)phenyl)ethan-1-ol (3b). Compound 3b was prepared according to the general procedure described above from 4-hydroxyphenylethanol 1a and 1-bromo-3-phenylpropane 2b in 95% yield as white powder. Mp=51-52° C.

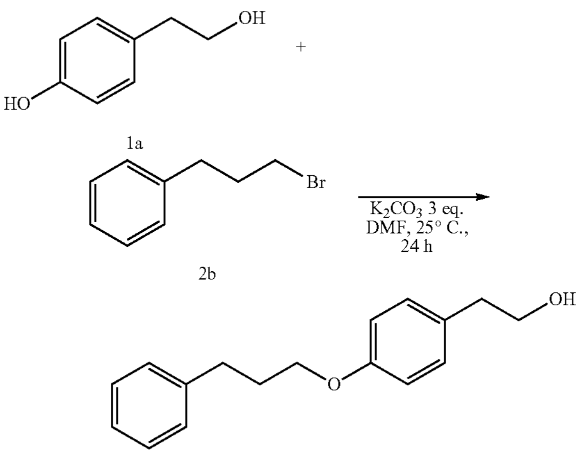

1a

2b

3b $^1$H NMR (300 MHz, DMSO-$d_6$) δ=2.01 (dt, J=8.6, 6.3 Hz, 2H, $CH_2$, H-2'), 2.65 (t, J=7.1 Hz, 2H, $CH_2$, H-3'), 2.73 (t, J=7.7 Hz, 2H, $CH_2$, H-2), 3.55 (t, J=7.1 Hz, 2H, $CH_2$, H-1), 3.91 (t, J=6.3 Hz, 2H, H-1'), 4.40-4.78 (br m, 1H, OH), 6.82 (d, J=8.4 Hz, 2H, H-$3^a$, H-$5^a$, Ar), 7.11 (d, J=8.4 Hz, 2H, H-$2^a$, H-$6^a$, Ar), 7.15-7.33 (m, 5H, H-$2^b$, H-$3^b$, H-$4^b$, H-$5^b$, H-$6^b$, Ar).

$^{13}$C NMR (75 MHz, DMSO-$d_6$) δ=30.4 (C-2'), 30.7 (C-3'), 38.2 (C-2), 62.4 (C-1), 66.6 (C-1'), 114.2 (C-$3^a$, C-$5^a$), 125.8 (C-$4^b$), 128.3 (C-$2^b$, C-$6^b$), 128.4 (C-$3^b$, C-$5^b$), 129.8 (C-$2^a$, C-$6^a$), 131.3 (C-$1^a$), 141.4 (C-$1^b$), 156.9 (C-$4^a$).

HRMS, m/z=279.1361 found (calculated for $C_{17}H_{20}O_2Na$ $[M+Na]^+$ requires 279.1362).

2-(4-(3-(4-Methoxyphenyl)propoxy)phenyl)ethan-1-ol (3c). Compound 3c was prepared according to the general procedure described above from 4-hydroxyphenylethanol 1a and 1-(3-bromopropyl)-4-methoxybenzene 2c in 85% yield as white powder. Mp=82-85° C.

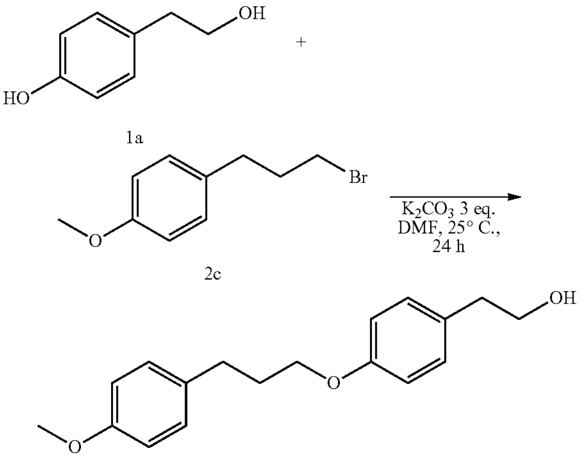

1a

2c

3c $^1$H NMR (300 MHz, DMSO-$d_6$) δ=1.96 (m, 2H, $CH_2$, H-2'), 2.65 (td, J=7.1, 5.1 Hz, 4H, $CH_2$, H-2, H-3'), 3.55 (q, J=6.6 Hz, 2H, $CH_2$, H-1), 3.71 (s, 3H, $OCH_3$), 3.89 (t, J=6.4 Hz, 2H, H-1'), 24.61 (t, J=5.2 Hz, 1H, OH), 6.83 (t, J=7.7 Hz, 4H, H-$2^a$, H-$6^a$, H-$2^b$, H-$6^b$, Ar), 7.12 (t, J=8.6 Hz, 4H, H-$3^a$, H-$5^a$, H-$3^b$, H-$5^b$, Ar).

$^{13}$C NMR (75 MHz, DMSO-$d_6$) δ=30.6 (C-3'), 30.7 (C-2'), 38.2 (C-2), 55.0 ($OCH_3$), 62.5 (C-1), 66.5 (C-1'), 113.8 (C-$3^b$, C-$5^b$), 114.2 (C-$3^a$, C-$5^a$), 129.3 (C-$2^b$, C-$6^b$), 129.8 (C-$2^a$, C-$6^a$), 131.3 (C-$1^a$), 133.2 (C-$1^b$), 156.9 (C-$4^a$), 157.5 (C-$4^b$).

HRMS, m/z=309.1467 found (calculated for $C_{18}H_{22}O_3Na$ $[M+Na]^+$ requires 309.1465).

2-(4-((4-Methoxybenzyl)oxy)phenyl)ethan-1-ol (3d). Compound 3d was prepared according to the general procedure described above from 4-hydroxyphenylethanol 1a and 4-methoxybenzylchloride 2d in 89% yield as white powder. Mp=95-98° C.

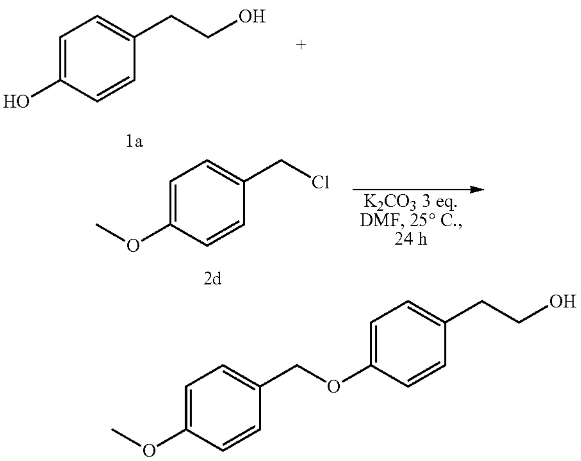

1a

2d

3d $^1$H NMR (300 MHz, DMSO-$d_6$) δ=2.64 (t, J=7.2 Hz, 2H, $CH_2$, H-2), 3.54 (td, J=7.1, 5.1 Hz, 2H, $CH_2$, H-1), 3.75 (s, 3H, $OCH_3$), 4.60 (t, J=5.2 Hz, 1H, OH), 4.97 (s, 2H, $OCH_2$), 6.89 (d, J=8.6 Hz, 2H, H-$3^b$, H-$5^b$, Ar), 6.94 (d, J=8.7 Hz, 2H, H-$3^a$, H-$5^a$, Ar), 7.11 (d, J=8.7 Hz, 2H, H-$2^b$, H-$6^b$, Ar), 7.36 (d, J=8.6 Hz, 2H, H-$2^a$, H-$6^a$, Ar).

$^{13}C$ NMR (75 MHz, DMSO-$d_6$) δ=38.2 (C-2), 55.1 ($OCH_3$), 62.5 (C-1), 68.9 ($OCH_2$), 113.8 (C-$3^b$, C-$5^b$), 114.6 (C-$3^a$, C-$5^a$), 129.2 (C-$1^b$), 129.4 (C-$2^a$, C-$6^a$), 129.8 (C-$2^b$, C-$6^b$), 131.5 (C-$1^a$), 156.7 (C-$4^a$), 158.9 (C-$4^b$).

HRMS, m/z=281.1150 found (calculated for $C_{16}H_{18}O_3Na$ $[M+Na]^+$ requires 281.1151).

2-(2-(3-Phenylpropoxy)phenyl)ethan-1-ol (3e). Compound 3e was prepared according to the general procedure described above from 2-hydroxyphenylethanol 1b and 1-bromo-3-phenylpropane 2b in 53% yield as yellowish oil.

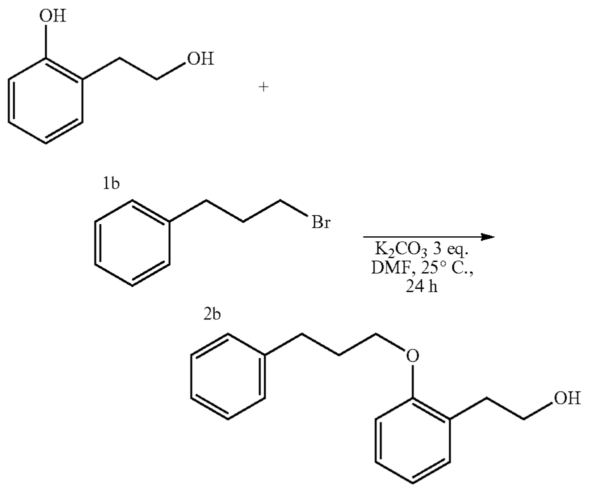

3e $^1H$ NMR (300 MHz, DMSO-$d_6$) δ=1.93-2.14 (m, 2H, $CH_2$, H-2'), 2.77 (td, J=7.2, 1.9 Hz, 4H, $CH_2$, H-2, H-3'), 3.60 (td, J=7.3, 5.1 Hz, 2H, $CH_2$, H-1), 3.94 (t, J=6.2 Hz, 2H, $CH_2$, H-1'), 4.59 (t, J=5.3 Hz, 1H, OH), 6.76-6.94 (m, 2H, H-$2^a$, H-$5^a$, Ar), 7.06-7.39 (m, 7H, H-$3^a$, H-$4^a$, H-$2^b$, H-$3^b$, H-$4^b$, H-$5^b$, H-$6^b$, Ar).

$^{13}C$ NMR (75 MHz, DMSO-$d_6$) δ=30.7 (C-2'), 31.7 (C-3'), 33.9 (C-2), 61.0 (C-1'), 66.5 (C-1), 111.5 (C-$2^a$), 120.2 (C-$3^a$), 126.0 (C-$4^b$), 127.3 (C-$1^b$), 127.4 (C-$4^a$), 128.5 (C-$2^b$, C-$3^b$, C-$5^b$, C-$6^b$), 130.6 (C-$5^a$), 141.5 (C-$1^a$), 156.6 (C-$6^a$).

HRMS m/z=279.1355 found (calculated for $C_{17}H_{20}O_2Na$ $[M+Na]^+$ requires 279.1356).

2-(2-(3-(4-Methoxyphenyl)propoxy)phenyl)ethan-1-ol (3j). Compound 3f was prepared according to the general procedure described above from 2-hydroxyphenylethanol 1b and 1-(3-bromopropyl)-4-methoxybenzene 2c in 64% yield, as yellowish oil.

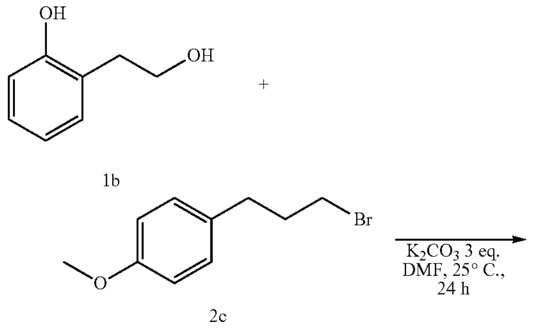

-continued

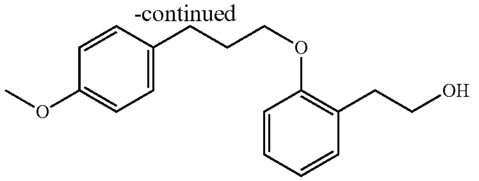

3f $^1H$ NMR (300 MHz, DMSO-$d_6$) δ=1.92-2.08 (m, 2H, $CH_2$, H-2'), 2.74 (dt, J=17.0, 7.7 Hz, 4H, $CH_2$, H-2, H-3'), 3.59 (td, J=7.4, 5.1 Hz, 2H, $CH_2$, H-1'), 3.72 ($OCH_3$) 3.92 (t, J=6.2 Hz, 2H, $CH_2$, H-1), 4.59 (t, J=5.3 Hz, 1H, OH), 6.75-6.95 (m, 4H, H-$2^a$, H-$5^a$, H-$3^b$, H-$5^b$, Ar), 7.13 (td, J=9.0, 4.9, 1.9 Hz, 4H, H-$3^a$, H-$4^a$, H-$2^b$, H-$6^b$, Ar).

$^{13}C$ NMR (75 MHz, DMSO-$d_6$) δ=30.6 (C-3'), 30.8 (C-2), 33.8 (C-2'), 55.0 ($OCH_3$), 60.9 (C-1'), 66.4 (C-1), 111.4 (C-$2^a$), 113.8 (C-$3^b$, C-$5^b$), 120.1 (C-$3^a$), 127.2 (C-$1^b$), 127.3 (C-$4^a$), 129.3 (C-$2^b$, C-$6^b$), 130.5 (C-$5^a$), 133.3 (C-$1^a$), 156.6 (C-$4^b$), 157.5 (C-$6^a$).

HRMS m/z=309.1461 found (calculated for $C_{18}H_{22}O_3Na$ $[M+Na]^+$ requires 309.1461).

2-(2-((4-Methoxybenzyl)oxy)phenyl)ethan-1-ol (3g). Compound 3g was prepared according to the general procedure described above from 2-hydroxyphenylethanol 1b and 4-methoxybenzylchloride 2d in 90% yield as yellowish oil.

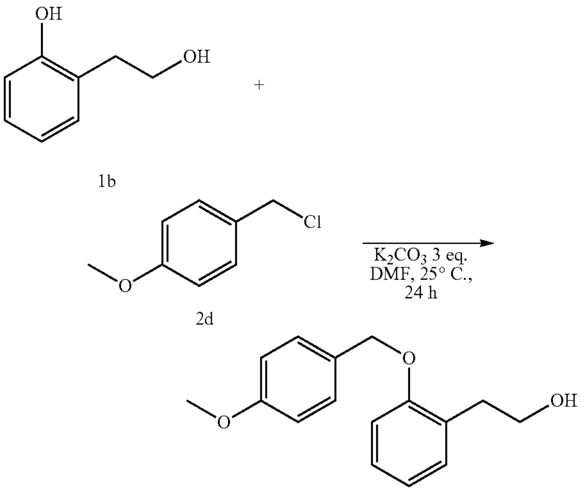

3g $^1H$ NMR (300 MHz, DMSO-$d_6$) δ=2.74 (t, J=7.3 Hz, 2H, $CH_2$, H-2), 3.52-3.61 (m, 2H, $CH_2$, H-1), 3.76 (s, $OCH_3$), 4.57 (t, J=5.3 Hz, 1H, OH), 5.02 (s, 2H, $CH_2$, $OCH_2$), 6.85 (td, J=7.4, 1.2 Hz, 1H, H-$3^a$, Ar), 6.95 (d, J=8.7 Hz, 2H, H-$3^b$, H-$5^b$, Ar), 7.01 (dd, J=8.7, 1.2 Hz, 1H, H-$4^a$), 7.15 (ddd, J=7.3, 4.3, 2.5 Hz, 2H, H-$2^a$, H-$5^a$, Ar), 7.38 (d, J=8.6 Hz, 2H, H-$2^b$, H-$6^b$, Ar).

$^{13}C$ NMR (75 MHz, DMSO-$d_6$) δ=33.8 (C-2), 55.1 ($OCH_3$), 60.8 (C-1), 69.0 ($OCH_2$), 112.0 (C-$2^a$), 113.9 (C-$2^b$, C-$6^b$), 120.3 (C-$3^a$), 127.2 (C-$4^a$), 127.4 (C-$1^a$), 129.1 (C-$3^b$, C-$5^b$), 129.3 (C-$1^b$), 130.5 (C-$5^a$), 156.3 (C-$6^a$), 158.9 (C-$4^b$).

HRMS m/z=281.1151 found (calculated for $C_{16}H_{18}O_3Na$ $[M+Na]^+$ requires 281.1148).

2-(3-(3-Phenylpropoxy)phenyl)ethan-1-ol (3h). Compound 3h was prepared according to the general procedure described above from 2-hydroxyphenylethanol 1c and 1-bromo-3-phenylpropane 2b in 78% yield as yellowish oil.

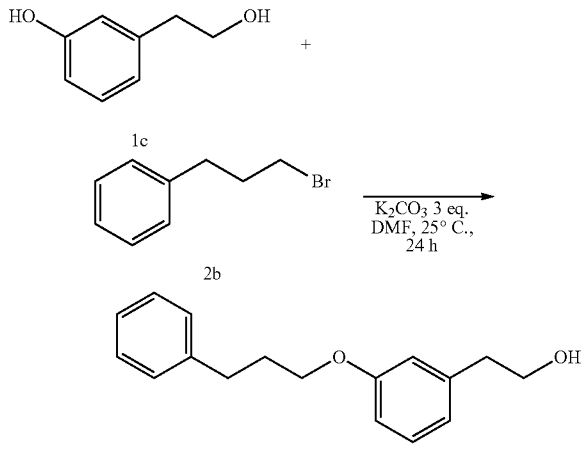

1c 2b 3h $^1$H NMR (300 MHz, DMSO-$d_6$) δ=1.92-2.09 (m, 2H, $CH_2$, H-2'), 2.71 (dt, J=14.7, 7.2 Hz, 4H, $CH_2$, H-2, H-3'), 3.59 (td, J=7.1, 5.1 Hz, 2H, $CH_2$, H-1'), 3.94 (t, J=6.4 Hz, 2H, $CH_2$, H-1), 4.60 (t, J=5.2 Hz, 1H, OH), 6.67-6.86 (m, 2H, H-2$^a$, H-4$^a$, Ar), 7.08-7.37 (m, 7H, H-3$^a$, H-6$^a$, H-2$^b$, H-3$^b$, H-4$^b$, H-5$^b$, H-6$^b$, Ar).

$^{13}$C NMR (75 MHz, DMSO-$d_6$) δ=30.4 (C-2'), 31.5 (C-3'), 39.0 (C-2), 62.1 (C-1'), 66.4 (C-1), 111.8 (C-2$^a$), 115.1 (C-4$^a$), 121.1 (C-6$^a$), 125.8 (C-3$^a$), 128.3 (C-2$^b$, C-3$^b$, C-5 b, C-6$^b$), 129.1 (C-4$^b$), 141.1 (C-1$^b$), 141.4 (C-1$^a$), 158.5 (C-5$^a$).

HRMS m/z=279.1355 found (calculated for $C_{17}H_{20}O_2Na$ [M+Na]$^+$ requires 279.1356).

2-(3-(3-(4-methoxyphenylpropoxy)phenyl)ethan-1-ol (3i). Compound 3i was prepared according to the general procedure described above from 2-hydroxyphenylethanol 1c and 1-(3-bromopropyl)-4-methoxybenzene 2c in 99% yield as white powder. Mp=53-55° C.

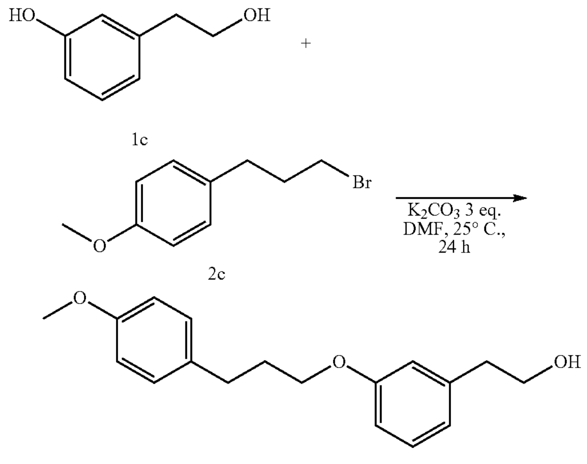

1c 2c 3i $^1$H NMR (300 MHz, DMSO-$d_6$) δ=1.96 (dq, J=8.4, 6.5 Hz, 2H, $CH_2$, H-2'), 2.67 (td, J=7.9, 7.5, 4.2 Hz, 4H, $CH_2$, H-2, H-3'), 3.59 (t, J=7.1 Hz, 2H, $CH_2$, H-1'), 3.71 (s, 3H, $OCH_3$), 3.91 (t, J=6.3 Hz, 2H, $CH_2$, H-1), 4.61 (s, 1H, OH), 6.68-6.80 (m, 3H, H-2$^a$, H-4$^a$, H-6$^a$, Ar), 6.85 (d, J=8.6 Hz, 2H, H-3$^b$, H-5$^b$, Ar), 7.06-7.24 (m, 3H, H-3$^a$, H-2$^b$, H-6$^b$, Ar).

$^{13}$C NMR (75 MHz, DMSO-$d_6$) δ=30.6 (C-2'), 30.7 (C-3'), 39.1 (C-2), 55.1 ($OCH_3$), 62.2 (C-1'), 66.5 (C-1), 111.9 (C-2$^a$), 113.9 (C-2$^b$, C-6$^b$), 115.2 (C-4$^a$), 121.2 (C-6$^a$), 129.2 (C-3$^a$), 129.4 (C-3$^b$, C-5$^b$), 133.3 (C-1$^b$), 141.2 (C-1$^a$), 157.5 (C-5$^a$), 158.6 (C-4$^b$).

HRMS m/z=309.1461 found (calculated for $C_{18}H_{22}O_3Na$ [M+Na]$^+$ requires 309.1461), 325.1197 found (calculated for $C_{18}H_{22}O_3K$ [M+K]$^+$ requires 325.1200).

2-(4-((4-Methoxybenzyl)oxy)phenyl)ethan-1-ol (3j). Compound 3j was prepared according to the general procedure described above from 2-hydroxyphenylethanol 1c and 1-(3-bromopropyl)-4-methoxybenzene 2d in 98% yield as white powder. Mp=62-64° C.

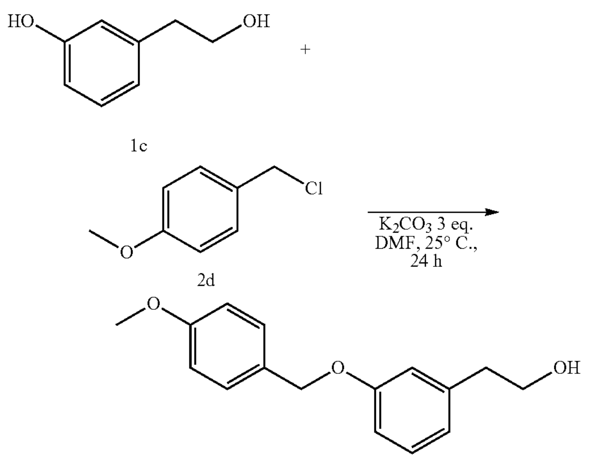

1c 2d 3j $^1$H NMR (300 MHz, DMSO-$d_6$) δ=2.68 (t, J=7.1 Hz, 2H, $CH_2$, H-2), 3.59 (t, J=7.1 Hz, 2H, $CH_2$, H-1), 3.75 (s, 3H, $OCH_3$), 4.62 (s, 1H, OH), 4.97 (s, 2H, $OCH_2$), 6.81 (ddd, J=14.3, 6.1, 4.4 Hz, 3H, H-2$^a$, H-4$^a$, H-6$^a$, Ar), 6.94 (d, J=8.6 Hz, 2H, H-3$^b$, H-5$^b$, Ar), 7.17 (t, J=7.8 Hz, 1H, H-3$^a$, Ar), 7.36 (d, J=8.5 Hz, 2H, H-2$^b$, H-6$^b$, Ar).

$^{13}$C NMR (75 MHz, DMSO-$d_6$) δ=39.0 (C-2), 55.4 ($OCH_3$), 62.4 (C-1), 69.1 ($OCH_2$), 112.4 (C-2$^a$), 114.1 (C-3$^b$, C-5$^b$), 115.8 (C-4$^a$), 121.6 (C-6$^a$), 129.4 (C-1$^a$), 129.5 (C-3$^a$), 129.8 (C-2$^b$, C-6$^b$), 141.3 (C-1$^b$), 158.6 (C-5$^a$), 159.2 (C-4$^b$).

HRMS m/z=281.1149 found (calculated for $C_{16}H_{18}O_3Na$ [M+Na]$^+$ requires 281.1148), 297.0888 found (calculated for $C_{16}H_{18}O_3K$ [M+K]$^+$ requires 297.0888).

2-(4-(2-Phenoxyethoxy)phenyl)ethan-1-ol (3k). Compound 3k was prepared according to the general procedure described above from 4-hydroxyphenylethanol 1a and 2-phenoxyethyl bromide 2e in 90% yield as white powder. Mp=143-145° C.

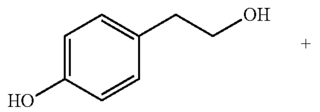

1a

-continued

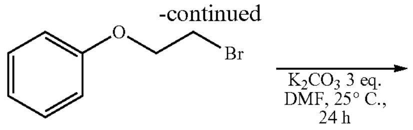

2e

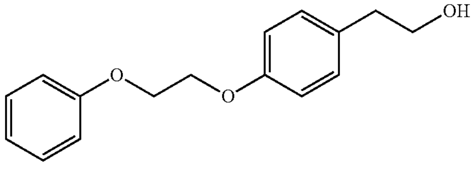

3k

$^1$H NMR (300 MHz, DMSO-d$_6$) δ=2.66 (t, J=7.1 Hz, 2H, $CH_2$, H-2), 3.56 (t, J=7.1 Hz, 2H, $CH_2$, H-1), 4.28 (s, 4H, $CH_2$, H-1', H-2'), 4.60 (s, 1H, OH), 6.84-7.05 (m, 5H, H-2$^a$, H-6$^a$, H-2$^b$, H-4$^b$, H-6$^b$, Ar), 7.13 (d, J=8.2 Hz, 2H, H-3$^a$, H-5$^a$, Ar), 7.30 (t, J=7.8 Hz, 2H, H-3$^b$, H-5$^b$, Ar).

$^{13}$C NMR (75 MHz, DMSO-d$_6$) δ=38.2 (C-2), 62.4 (C-1), 66.3 (C-2'), 66.3 (C-1'), 114.3 (C-3$^a$, C-5$^a$), 114.5 (C-3$^b$, C-5$^b$), 120.8 (C-4$^b$), 129.6 (C-2$^a$, C-6$^a$), 129.9 (C-2$^b$, C-6$^b$), 131.7 (C-1$^a$), 156.6 (C-4$^a$), 158.3 (C-4$^b$).

HRMS m/z=281.1147 found (calculated for $C_{16}H_{18}O_3Na$ [M+Na]$^+$ requires 281.1148), 297.0883 found (calculated for $C_{16}H_{18}O_3K$ [M+K]$^+$ requires 297.0887).

Example 13

General procedure for mesylation of O-alkyl-phenylethanol 3(b-k) in the preparation of phenethyl methanesulfonate derivatives 4(b-k). A solution of methanesulfonyl chloride (1.55 g, 13.52 mmol, 2 equiv.) in anhydrous $CH_2Cl_2$ (3.5 ml) was added drop-wise during 15 minutes under magnetic stirring (500 rpm) in a cooled solution (0° C., ice bath) of phenylethan-1-ol derivative 3 (6.76 mmol) and triethylamine TEA (1.71 g, 16.9 mmol, 2.5 eq.) in 8 ml of dry $CH_2Cl_2$. Stirring at room temperature was further pursued for 8 hours. The crude reaction mixture was transferred into a separating funnel. The organic layer was successively washed with deionised water (3x100 ml), saturated sodium hydrogenocarbonate $NaHCO_3$ (3x100 ml). After decantation, the organic layer was dried over anhydrous $MgSO_4$, filtered on a paper filter and the filtrate was concentrated in rotary evaporator under reduced pressure. If the crude residue crystallized, then it was triturated in deionized water (3x50 ml). If a viscous oil was obtained, then it was triturated in 8 ml of di-iso-propylether that produced crystallization and the resulting material was washed with deionized water (3x45 ml). The resulting solid was then dried under high vacuum ($10^{-3}$ Torr) and afforded the desired compound 3. The compound 3 was used later without further purification.

4-(3-Phenylpropoxy)phenethyl methanesulfonate (4b). Compound 4b was prepared according to the general procedure described above from 2-(4-(3-phenyl propoxy)phenyl)ethan-1-ol 3b and methanesulfonyl chloride in 67% yield as white powder. Mp=51-52° C.

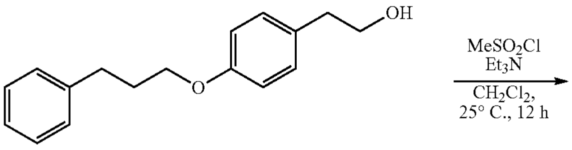

3b

-continued

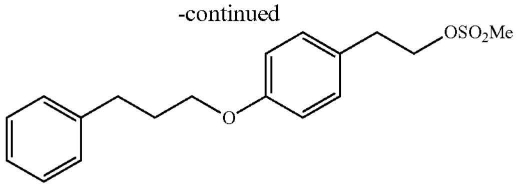

4b

$^1$H NMR (300 MHz, DMSO-d$_6$) δ=1.87-2.09 (m, 2H, $CH_2$, H-2'), 2.73 (t, J=7.7 Hz, 2H, $CH_2$, H-3'), 2.92 (t, J=6.8 Hz, 2H, $CH_2$, H-2), 3.09 (s, 3H, $SO_2CH_3$), 3.94 (t, J=6.3 Hz, 2H, $CH_2$, H-1), 4.36 (t, J=6.8 Hz, 2H, $CH_2$, H-1'), 6.87 (d, J=8.4, 2H, H-3$^a$, H-5$^a$, Ar), 7.10-7.35 (m, 7H, H-2$^a$, H-6$^a$, H-2$^b$, H-3$^b$, H-4$^b$, H-5$^b$, H-6$^b$, Ar).

$^{13}$C NMR (75 MHz, DMSO-d$_6$) δ=30.5 (C-2'), 31.6 (C-3'), 34.0 (C-2), 36.7 ($SO_2CH_3$), 66.7 (C-1'), 71.0 (C-1), 114.6 (C-3$^a$, C-5$^a$), 126.0 (C-4$^b$), 128.5 (C-2$^b$, C-6$^b$, C-3$^b$, C-5$^b$), 128.8 (C-1$^a$), 130.2 (C-2$^a$, C-6$^a$), 141.5 (C-1$^b$), 157.5 (C-4$^a$).

HRMS, m/z=357.1137 found (calculated for $C_{18}H_{22}O_4SNa$ [M+Na]$^+$ requires 357.1138).

4-(3-(4-Methoxyphenyl)propoxy)phenethyl methanesulfonate (4c). Compound 4c was prepared according to the general procedure described above from 2-(4-(3-(4-methoxyphenyl)propoxy)phenyl)ethan-1-ol 3c and methanesulfonyl chloride in 68% yield as white powder. Mp=117-120° C.

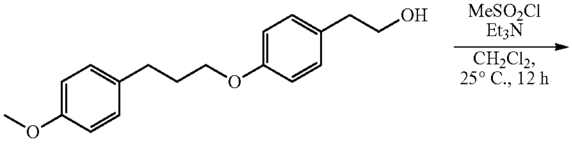

3c

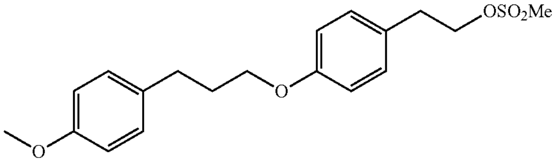

4c

$^1$H NMR (300 MHz, DMSO-d$_6$) δ=1.82-2.06 (m, 2H, $CH_2$, H-2'), 2.58-2.72 (m, 2H, $CH_2$, H-3'), 2.92 (t, J=6.8 Hz, 2H, $CH_2$, H-2), 3.10 (s, 3H, $SO_2CH_3$), 3.71 (s, 3H, $OCH_3$), 3.92 (t, J=6.4 Hz, 2H, $CH_2$, H-1), 4.36 (t, J=6.8 Hz, 2H, $CH_2$, H-1'), 6.83-6.89 (m, 4H, H-3$^a$, H-5$^a$, H-3$^b$, H-5$^b$, Ar), 7.14 (d, J=8.6 Hz, 2H, H-2$^b$, H-6$^b$, Ar), 7.20 (d, J=8.4, 2H, H-2$^a$, H-6$^a$, Ar).

$^{13}$C NMR (75 MHz, DMSO-d$_6$) δ=30.5 (C-2'), 30.6 (C-3'), 33.8 (C-2), 36.6 ($SO_2CH_3$), 55.0 ($OCH_3$), 66.6 (C-1'), 70.9 (C-1), 113.8 (C-3$^b$, C-5$^b$), 114.4 (C-3$^a$, C-5$^a$), 128.6 (C-1$^a$), 129.3 (C-2$^b$, C-6$^b$), 130.0 (C-2$^a$, C-6$^a$), 133.2 (C-1$^b$), 157.4 (C-4$^b$).

HRMS, m/z=387.1242 found (calculated for $C_{19}H_{24}O_5SNa$ [M+Na]$^+$ requires 387.1242); 269.1542 found (calculated for $C_{18}H_{21}O_2$ [M-$OSO_2$Me]$^+$ requires 269.1543).

4-((4-Methoxybenzyl)oxy)phenethyl methanesulfonate (4d). Compound 4d was prepared according to the general procedure described above from 2-(4-((4-methoxy benzyl)

oxy)phenyl)ethan-1-ol 3d and methanesulfonyl chloride in 91% yield as white powder. Mp=100-103° C.

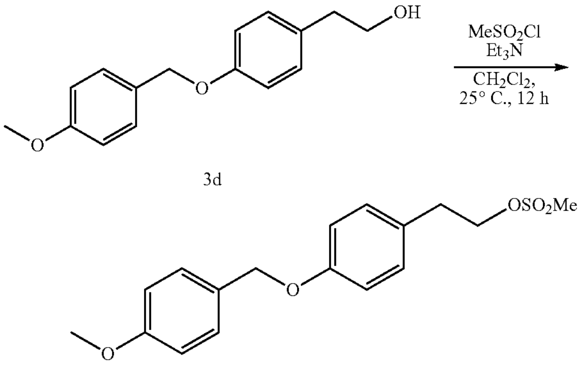

3d

4d

$^1$H NMR (300 MHz, DMSO-$d_6$) δ=2.92 (t, J=6.8 Hz, 2H, $CH_2$, H-2), 3.10 (s, 3H, $SO_2CH_3$), 3.75 (s, 3H, $OCH_3$), 4.35 (t, J=6.8 Hz, 2H, $CH_2$, H-1), 4.99 (s, 2H, $OCH_2$), 6.79-7.02 (m, 4H, H-$3^a$, H-$5^a$, H-$3^b$, H-$5^b$, Ar), 7.20 (d, J=8.6 Hz, 2H, H-$2^b$, H-$6^b$, Ar), 7.37 (d, J=8.6 Hz, 2H, H-$2^a$, H-$6^a$, Ar).

$^{13}$C NMR (75 MHz, DMSO-$d_6$) δ=33.9 (C-2), 36.6 ($SO_2CH_3$), 55.1 ($OCH_3$), 68.9 ($OCH_2$), 70.9 (C-1), 113.8 (C-$3^b$, C-$5^b$), 114.8 (C-$3^a$, C-$5^a$), 128.8 (C-$1^b$), 129.0 (C-$1^a$), 129.5 (C-$2^b$, C-$6^b$), 130.0 (C-$2^a$, C-$6^a$), 157.2 (C-$4^a$), 159.0 (C-$4^b$).

HRMS, m/z=359.0929 found (calculated for $C_{17}H_{20}O_5SNa$ $[M+Na]^+$ requires 359.0930).

Example 14

TABLE 1

Other O-alkyl-phenethyl methanesulfonate 4 derived from O-alkyl-phenylethanol 3, which were synthesized according to procedures described in previous examples.

| | Compound Number | Isolated yield (%) | Mp (° C.) or physical state | Method of preparation |
|---|---|---|---|---|
| 4e | 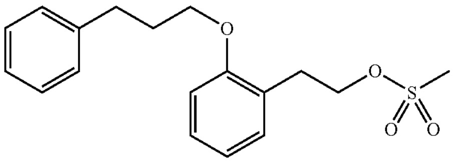 [SMILES: CS(=O)(=O)OCCc1ccccc1OCCCc1ccccc1] | 59 | Yellowish oil | Example 13 |
| 4f | 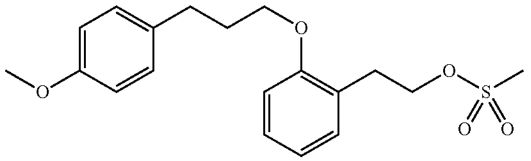 | 76 | Yellowish oil | Example 13 |
| 4g | 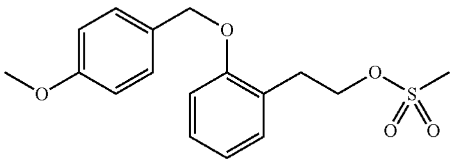 | 54 | Light yellow oil | Example 13 |
| 4h | 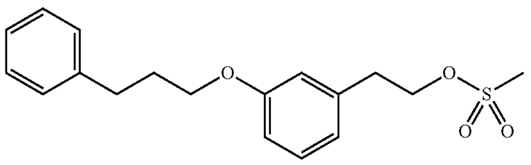 [SMILES: CS(=O)(=O)OCCc1cccc(OCCCc2ccccc2)c1] | 60 | Yellow oil | Example 13 |
| 4i | 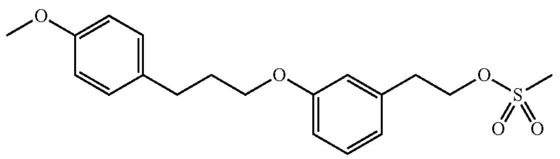 | 43 | 64-66 | Example 13 |

TABLE 1-continued

Other O-alkyl-phenethyl methanesulfonate 4 derived from O-alkyl-phenylethanol 3, which were synthesized according to procedures described in previous examples.

| Compound Number | | Isolated yield (%) | Mp (° C.) or physical state | Method of preparation |
|---|---|---|---|---|
| 4j | 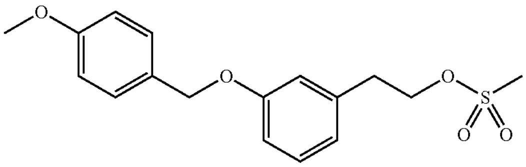 | 20 | 65-67 | Example 13 |
| 4k | 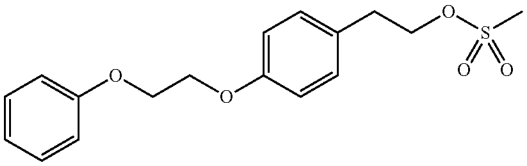 [SMILES: CS(=O)(=O)OCCc1ccc(OCCOc2ccccc2)cc1] | 77 | 112-114 | Example 13 |
| 4l | 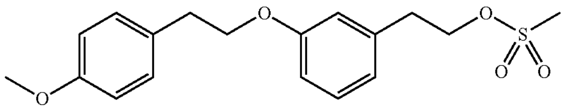 | 62 | <50 | Example 13 |
| 4m | 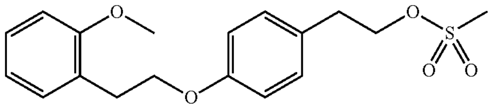 [SMILES: COc1ccccc1CCOc1ccc(CCOS(C)(=O)=O)cc1] | 60 | Yellow oil | Example 13 |
| 4n | 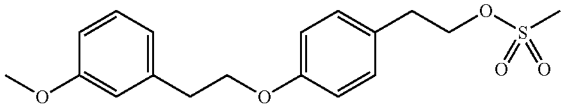 | 74 | Yellow oil | Example 13 |
| 4o | 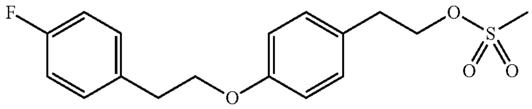 [SMILES: CS(=O)(=O)OCCc1ccc(OCCc2ccc(F)cc2)cc1] | 71 | <50 | Example 13 |
| 4p | 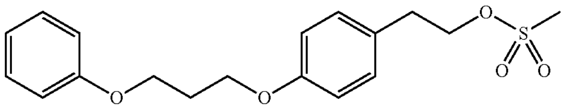 [SMILES: CS(=O)(=O)OCCc1ccc(OCCCOc2ccccc2)cc1] | 63 | 65-67 | Example 13 |

Example 15

TABLE 2

Other N-phenylalkyl azole SOCE inhibitors 6α, 6β synthesized from 5α or 5β and O-alkyl-phenethyl methanesulfonate 4.

| Compound Number | | Isolated yield (%) | Mp (° C.) or physical state | Method of preparation | Starting compounds |
|---|---|---|---|---|---|
| 6αn | 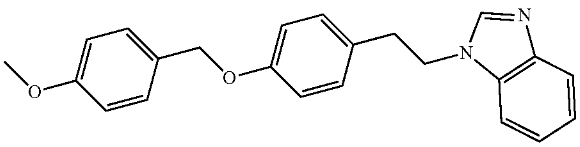 [SMILES: COc1ccc(COc2ccc(CCn3cnc4ccccc43)cc2)cc1] | 69 | 127-129 | Example 1 | 5αa, 4d |

TABLE 2-continued

Other N-phenylalkyl azole SOCE inhibitors 6α, 6β synthesized from 5α or 5β and O-alkyl-phenethyl methanesulfonate 4.

| Compound Number | | Isolated yield (%) | Mp (° C.) or physical state | Method of preparation | Starting compounds |
|---|---|---|---|---|---|
| 6αo | 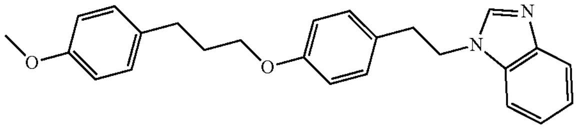 [SMILES: COc1ccc(CCCOc2ccc(CCn3cnc4ccccc43)cc2)cc1] | 62 | 126-128 | Example 1 | 5αa, 4c |
| 6αp | 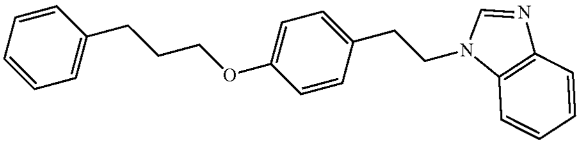 [SMILES: c1ccc(CCCOc2ccc(CCn3cnc4ccccc43)cc2)cc1] | 52 | 105-107 | Example 1 | 5αa, 4b |
| 6αq | 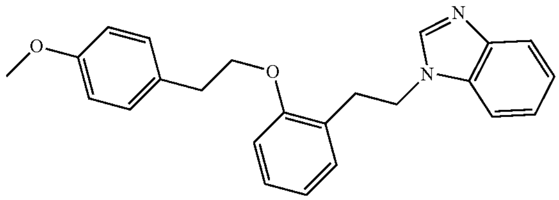 [SMILES: COc1ccc(CCOc2ccccc2CCn2cnc3ccccc32)cc1] | 82 | White powder | Example 1 | 5αa, 4r |
| 6αr | 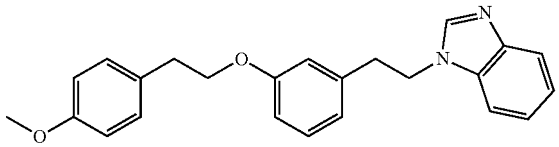 [SMILES: COc1ccc(CCOc2cccc(CCn3cnc4ccccc43)c2)cc1] | 77 | 123-125 | Example 1 | 5αa, 4l |
| 6αs | 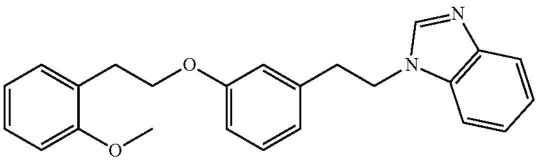 [SMILES: COc1ccccc1CCOc1cccc(CCn2cnc3ccccc32)c1] | 57 | 119-120 | Example 1 | 5αa, 4m |
| 6αt | 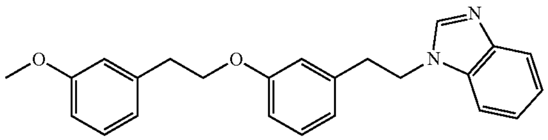 [SMILES: COc1cccc(CCOc2cccc(CCn3cnc4ccccc43)c2)c1] | 39 | 99-101 | Example 1 | 5αa, 4n |
| 6αu | 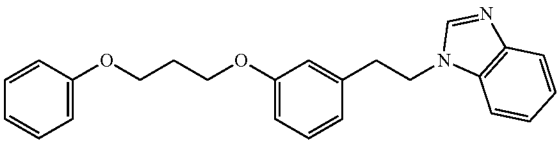 [SMILES: c1ccc(OCCCOc2cccc(CCn3cnc4ccccc43)c2)cc1] | 48 | 103-105 | Example 1 | 5αa, 4k |
| 6αv | 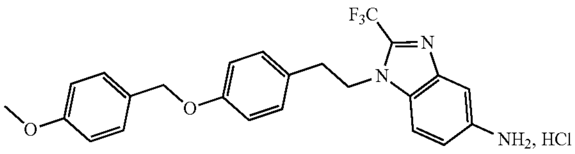 | 77 | 132-134 | Example 8 | 5αf, 4d |
| 6αw | 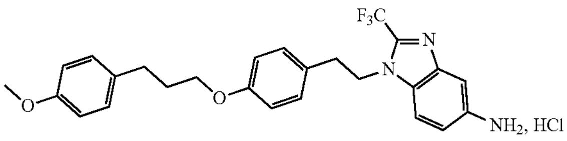 | 86 | 144-146 | Example 8 | 5αf, 4c |

TABLE 2-continued

Other N-phenylalkyl azole SOCE inhibitors 6α, 6β synthesized from 5α or 5β and O-alkyl-phenethyl methanesulfonate 4.

| Compound Number | | Isolated yield (%) | Mp (° C.) or physical state | Method of preparation | Starting compounds |
|---|---|---|---|---|---|
| 6αx | 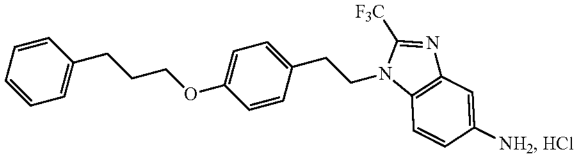 | 72 | 140-142 | Example 8 | 5αf, 4b |
| 6αy | 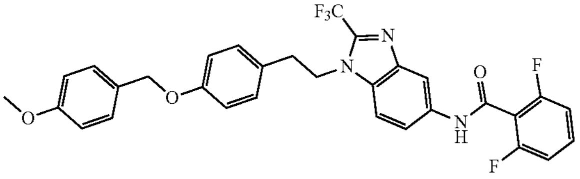 [SMILES: COc1ccc(COc2ccc(CCn3c(C(F)(F)F)nc4cc(NC(=O)c5c(F)cccc5F)ccc43)cc2)cc1] | 30 | 129-131 | Example 6 | 5αg, 4d |
| 6αz | 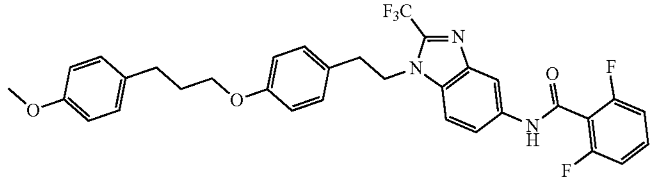 [SMILES: COc1ccc(CCCOc2ccc(CCn3c(C(F)(F)F)nc4cc(NC(=O)c5c(F)cccc5F)ccc43)cc2)cc1] | 38 | Gummy solid | Example 6 | 5αg, 4c |
| 6αaa | 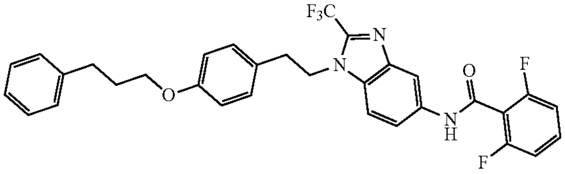 [SMILES: O=C(Nc1ccc2c(c1)nc(C(F)(F)F)n2CCc1ccc(OCCCc2ccccc2)cc1)c1c(F)cccc1F] | 70 | 74-77 | Example 6 | 5αg, 4b |
| 6αab | 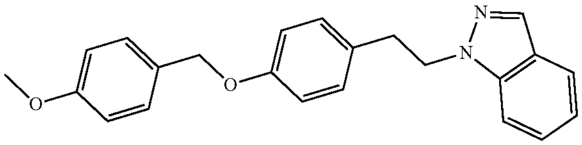 [SMILES: COc1ccc(COc2ccc(CCn3ncc4ccccc43)cc2)cc1] | 48 | 124-126 | Example 1 | 5αb, 4d |
| 6αac | 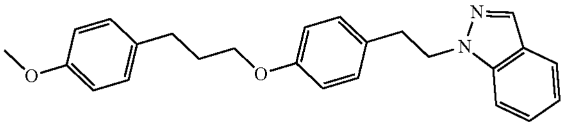 [SMILES: COc1ccc(CCCOc2ccc(CCn3ncc4ccccc43)cc2)cc1] | 62 | 102-104 | Example 1 | 5αb, 4c |
| 6βd | 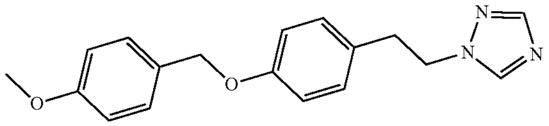 [SMILES: COc1ccc(COc2ccc(CCn3cncn3)cc2)cc1] | 39 | 126-128 | Example 1 | 5αb, 4b |
| 6ße | 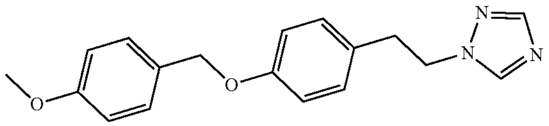 [SMILES: COc1ccc(COc2ccc(CCn3cncn3)cc2)cc1] | 65 | 127-129 | Example 10 | 5βb, 4d |
| 6βf | 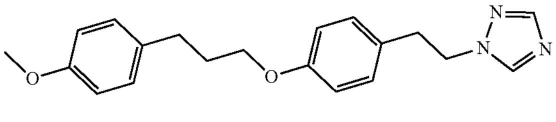 [SMILES: COc1ccc(CCCOc2ccc(CCn3cncn3)cc2)cc1] | 52 | 76-78 | Example 10 | 5βb, 4c |

TABLE 2-continued

Other N-phenylalkyl azole SOCE inhibitors 6α, 6β synthesized from 5α or 5β and O-alkyl-phenethyl methanesulfonate 4.

| | Compound Number | Isolated yield (%) | Mp (° C.) or physical state | Method of preparation | Starting compounds |
|---|---|---|---|---|---|
| 6βg | 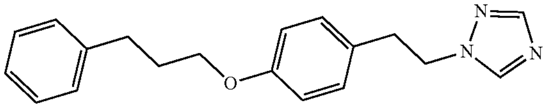 [SMILES: c1ccc(CCCOc2ccc(CCn3cncn3)cc2)cc1] | 33 | 56-58 | Example 10 | 5βb, 4b |
| 6βh | 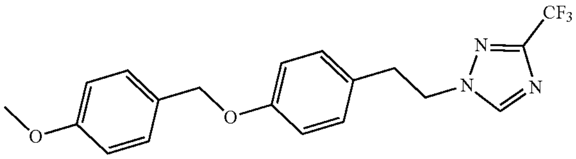 [SMILES: COc1ccc(COc2ccc(CCn3cnc(C(F)(F)F)n3)cc2)cc1] | 49 | 105-107 | Example 9 | 5βa, 4d |
| 6βi | 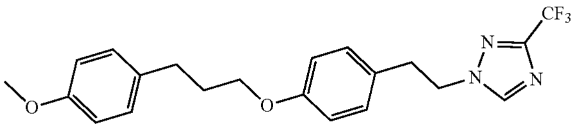 [SMILES: COc1ccc(CCCOc2ccc(CCn3cnc(C(F)(F)F)n3)cc2)cc1] | 44 | 83-85 | Example 9 | 5βa, 4c |
| 6βj | 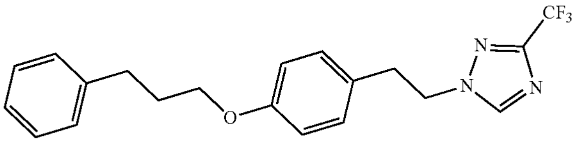 [SMILES: FC(F)(F)c1ncn(CCc2ccc(OCCCc3ccccc3)cc2)n1] | 23 | 77-79 | Example 9 | 5βa, 4b |
| 6βk | 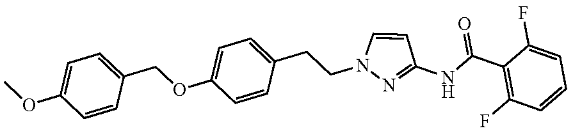 [SMILES: COc1ccc(COc2ccc(CCn3ccc(NC(=O)c4c(F)cccc4F)n3)cc2)cc1] | 21 | 210-212 | Example 11 | 5βd, 4d |
| 6βl | 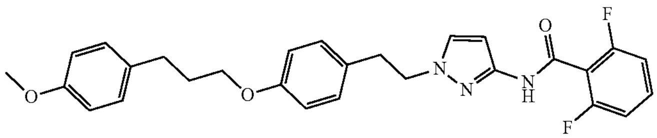 [SMILES: COc1ccc(CCCOc2ccc(CCn3ccc(NC(=O)c4c(F)cccc4F)n3)cc2)cc1] | 36 | Gummy solid | Example 11 | 5βd, 4c |
| 6βm | 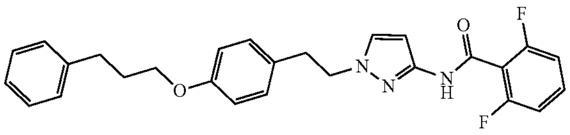 [SMILES: O=C(Nc1ccn(CCc2ccc(OCCCc3ccccc3)cc2)n1)c1c(F)cccc1F] | 37 | Gummy solid | Example 11 | 5βd, 4b |
| 6βn | 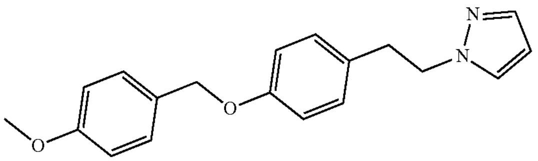 [SMILES: COc1ccc(COc2ccc(CCn3cccn3)cc2)cc1] | 84 | 131-133 | Example 10 | 5βe, 4d |
| 6βo | 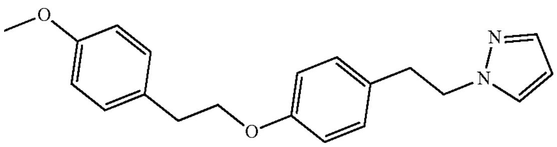 [SMILES: COc1ccc(CCOc2ccc(CCn3cccn3)cc2)cc1] | 71 | 56-60 | Example 10 | 5βe, 4a |
| 6βp | 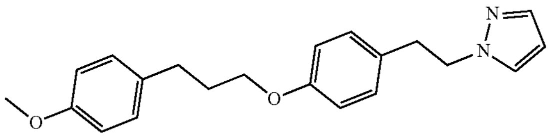 [SMILES: COc1ccc(CCCOc2ccc(CCn3cccn3)cc2)cc1] | 82 | 69-73 | Example 10 | 5βe, 4c |

TABLE 2-continued

Other N-phenylalkyl azole SOCE inhibitors 6α, 6β synthesized from 5α or 5β and O-alkyl-phenethyl methanesulfonate 4.

| Compound Number | | Isolated yield (%) | Mp (° C.) or physical state | Method of preparation | Starting compounds |
|---|---|---|---|---|---|
| 6βq | 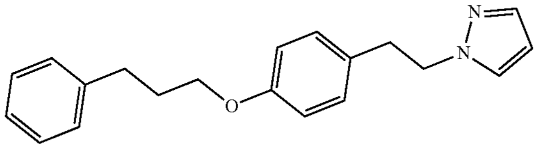 [SMILES: c1ccc(CCCOc2ccc(CCn3cccn3)cc2)cc1] | 56 | <50 | Example 10 | 5βe, 4b |
| 6βr | 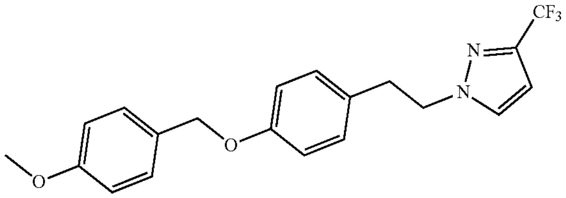 [SMILES: COc1ccc(COc2ccc(CCn3ccc(C(F)(F)F)n3)cc2)cc1] | 85 | 79-83 | Example 9 | 5βf, 4d |
| 6βs | 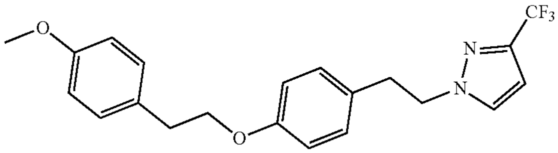 [SMILES: COc1ccc(CCOc2ccc(CCn3ccc(C(F)(F)F)n3)cc2)cc1] | 48 | Yellowish oil | Example 9 | 5βf, 4a |
| 6βt | 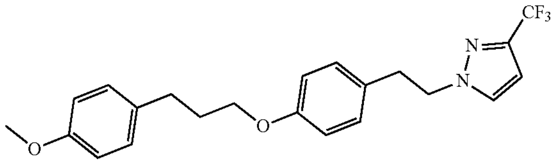 [SMILES: COc1ccc(CCCOc2ccc(CCn3ccc(C(F)(F)F)n3)cc2)cc1] | 78 | 117-120 | Example 9 | 5βf, 4c |
| 6βu | 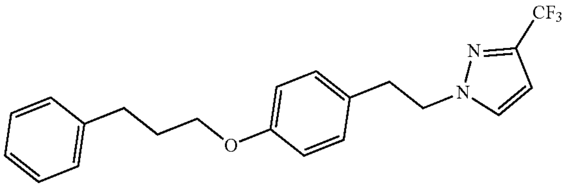 [SMILES: FC(F)(F)c1ccn(CCc2ccc(OCCCc3ccccc3)cc2)n1] | 54 | Yellowish oil | Example 9 | 5βf, 4b |
| 6βv | 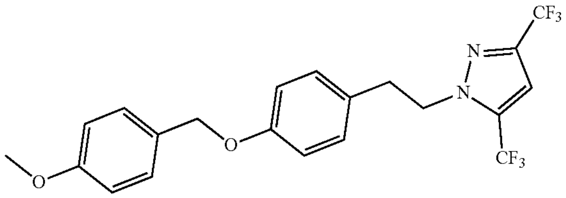 [SMILES: COc1ccc(COc2ccc(CCn3nc(C(F)(F)F)cc3C(F)(F)F)cc2)cc1] | 74 | 129-130 | Example 9 | 5βg, 4d |
| 6βw | 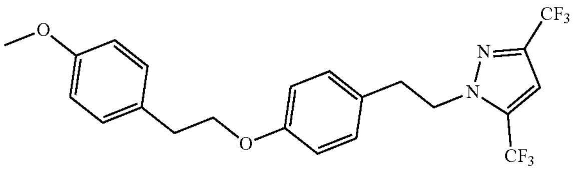 [SMILES: COc1ccc(CCOc2ccc(CCn3nc(C(F)(F)F)cc3C(F)(F)F)cc2)cc1] | 53 | Colorless oil | Example 9 | 5βg, 4a |
| 6βx | 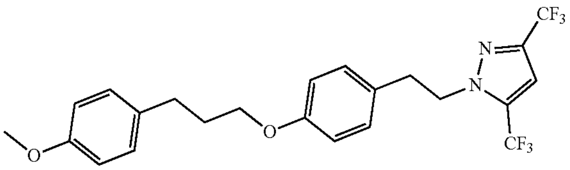 [SMILES: COc1ccc(CCCOc2ccc(CCn3nc(C(F)(F)F)cc3C(F)(F)F)cc2)cc1] | 78 | 117-120 | Example 9 | 5βg, 4c |

TABLE 2-continued

Other N-phenylalkyl azole SOCE inhibitors 6α, 6β synthesized from 5α or 5β and O-alkyl-phenethyl methanesulfonate 4.

| Compound Number | | Isolated yield (%) | Mp (° C.) or physical state | Method of preparation | Starting compounds |
|---|---|---|---|---|---|
| 6βy | 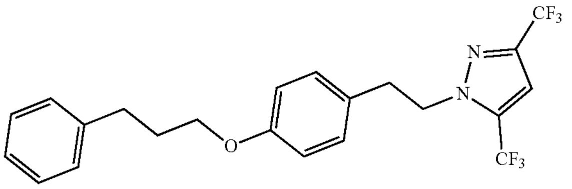 [SMILES: FC(F)(F)c1cc(C(F)(F)F)n(CCc2ccc(OCCCc3ccccc3)cc2)n1] | 49 | Colorless oil | Example 9 | 5βg, 4b |

Example 16

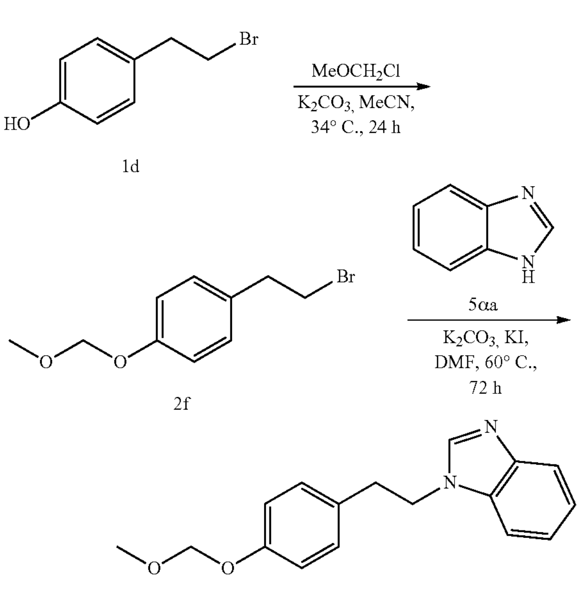

1d, 2f, 5αa, 6αad 1-(2-Bromoethyl)-4-(methoxymethoxy)benzene (2j). To a solution of 4-(2-bromoethyl)phenol 1d (1.507 g, 7.497 mmol) in 25 ml of dry acetonitrile under vigorous magnetic stirring (550 rpm) was added portion-wise 3.108 g of potassium carbonate $K_2CO_3$ (22.49 mmol, 3 eq.) at room temperature. After 30 minutes, a solution of chloromethoxymethane $MeOCH_2Cl$ (1.508 g, 18.74 mmol, 2.5 eq.) in 15 ml of dry acetonitrile was added dropwise for 15 minutes and the resulting reaction mixture was heated at 34° C. for 24 hours (monitored by thin layer chromatography with 0.2 mm plates of silica gel 60-F254 Merck using $CH_2Cl_2$/MeOH 95:5 v/v as eluent). After cooling down to room temperature, the reaction mixture was concentrated using a rotary evaporator under reduced pressure. To the crude residue was poured 100 ml of deionized water, then extraction was conducted with $CH_2Cl_2$ (3×30 ml) and the collected extracts were transferred into a separated funnel. The organic phase was successively washed with brine (2×50 ml), dried over anhydrous $MgSO_4$, filtered in a filter paper and the filtrate was concentrated in vacuo. To the crude residue was poured 15 ml of cyclohexane to produce precipitation of un-reacted 4-(2-bromoethyl)phenol 1d which was eliminated by filtration in a Buchner funnel (porosity No 4) and elimination of cyclohexane from the filtrate in vacuo gave the desired compound 2f in 64% yield as translucent mobile oil. The compound 2f was found to be pure enough to be used later without purification.

$^1$H NMR (300 MHz, $CDCl_3$) δ=3.12 (t, J=7.6 Hz, 2H, H-2), 3.49 (s, 3H, H-4"), 3.54 (dd, J=8.0, 7.3 Hz, 2H, H-1), 5.17 (s, 2H, H-2"), 7.01 (d, J=8.7 Hz, 2H, H-3', H-5', Ar), 7.14 (d, J=8.7 Hz, 2H, H-2', H-6', Ar).

$^{13}$C NMR (75 MHz, $CDCl_3$) δ=33.3 (C-1), 38.7 (C-2), 56.0 (C-4"), 94.6 (C-2"), 116.5 (C-3', C-5'), 129.8 (C-2', C-6'), 132.4 (C-1'), 156.3 (C-4').

1-(4-(Methoxymethoxy)phenethyl)-1H-benzo[d]imidazole (6αad). To a vigorous stirred (550 rpm) solution of benzimidazole 5αa (0.385 g, 3.26 mmol, 2 eq.) in 6 ml of dry DMF was added portion-wise potassium carbonate $K_2CO_3$ (0.677 g, 4.89 mmol, 3 eq.). After 30 minutes of magnetic stirring, 1-(2-bromethyl)-4-(methoxy methoxy)-benzene 2f (0.4 g, 1.63 mmol, 1 eq.) and potassium iodide KI (0.054 g, 0.33 mmol, 0.2 eq.) were added to the reaction mixture and the resulting reaction mixture was stirred at 60° C. for 72 hours (monitored by thin layer chromatography with 0.2 mm plates of silica gel 60-F254 Merck using $CH_2Cl_2$/MeOH 95:5 v/v as eluent). After cooling down to room temperature, 60 ml of deionised water was poured in the reaction mixture and the resulting mixture was transferred into a separating funnel. Extraction was conducted with ethyl acetate (2×30 ml) and then, the collected extracts were successively washed with brine (3×20 ml), dried over anhydrous $MgSO_4$ and filtered in a filter paper. The filtrate was concentrated using a rotary evaporator under reduced pressure and the crude residue was submitted to purification by chromatography (Combi Flash $R_f$ 200 psi apparatus with a DAD 200/360 nm detector) on pre-packed column of silica gel 60 F-254 (Merck) using a stepwise gradient of cyclohexane/AcOEt (0-80%) for elution. Pooling for 60 minutes and elimination of the solvent in vacuo gave the pure desired compound 6αad as ivory gummy paste in 44% yield.

$^1$H NMR (300 MHz, $CDCl_3$) δ=3.08 (t, J=7.0 Hz, 2H, H-2'), 3.47 (s, 3H, H-4"), 4.36 (t, J=7.0 Hz, 2H, H-1'), 5.14 (s, 2H, H-2"), 6.93 (s, 4H, H-2$^a$, H-3$^a$, H-5$^a$ H-6$^a$), 7.29 (m, 2H, H-5, H-6, Ar), 7.38 (m, 1H, H-7, Ar), 7.62 (s, 1H, H-2), 7.81 (m, 1H, H-4, Ar).

$^{13}$C NMR (75 MHz, $CDCl_3$) δ=35.6 (C-2'), 47.0 (C-1'), 56.1 (C-4"), 94.6 (C-2"), 109.6 (C-7), 116.8 (C-3$^a$, C-5$^a$), 120.6 (C-4), 122.2 (C-5), 122.9 (C-6), 123.0 (C-7$^a$), 129.8 (C-2$^a$, C-6$^a$), 130.9 (C-1$^a$), 133.7 (C-3$^a$), 143.1 (C-2), 156.4 (C-4$^a$).

Example 17

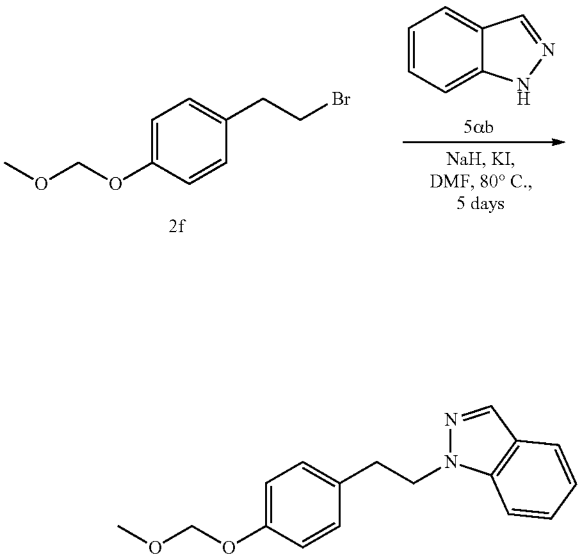

2f

6αae 1-(4-(Methoxymethoxy)phenethyl)-1H-indazole (6αae). To a vigorous stirred (550 rpm) solution of indazole 5αb (0.289 g, 2.45 mmol, 1.5 eq.) in 4 ml of dry DMF was added portion-wise sodium hydride 60% dispersion in mineral oil (0.261 g, 6.53 mmol, 4 eq.). After 30 minutes of magnetic stirring, 1-(2-bromethyl)-4-(methoxy-methoxy)benzene 2f (0.4 g, 3 mmol, 1 eq.) and potassium iodide KI (0.054 g, 0.33 mmol, 0.2 eq.) were added to the reaction mixture and the resulting reaction mixture was stirred at 80° C. during 5 days (monitored by thin layer chromatography with 0.2 mm plates of silica gel 60-F254 Merck using $CH_2Cl_2$/MeOH 95:5 v/v as eluent). After cooling down to room temperature, 40 ml of deionised water was poured in the reaction mixture and the resulting mixture was transferred into a separating funnel. Extraction was conducted with ethyl acetate (2×20 ml) then, the collected extracts were successively washed with brine (3×15 ml), dried over anhydrous $MgSO_4$ and filtered in a filter paper. The filtrate was concentrated in a rotary evaporator under reduced pressure and the crude residue was submitted to purification by chromatography (Combi Flash $R_f$ 200 psi apparatus with a DAD 200/360 nm detector) on pre-packed column of silica gel 60 F-254 (Merck) using a stepwise gradient of cyclohexane/AcOEt (0-20%) for elution. Pooling for 60 minutes and elimination of the solvent in vacuo gave the pure desired compound 6αae as translucent viscous oil in 54% yield.

$^1$H NMR (300 MHz, $CDCl_3$) δ=3.20 (m, 2H, H-2'), 3.49 (s, 3H, H-4"), 4.59 (m, 2H, H-1'), 5.16 (s, 2H, H-2"), 6.96 (m, 2H, H-3$^a$, H-5$^a$, Ar), 7.07 (m, 2H, H-2$^a$, H-6$^a$, Ar), 7.14 (ddd, J=7.9, 6.6, 1.2 Hz, 1H, H-5, Ar), 7.27 (dq, J=8.7, 1.1 Hz, 1H, H-7, Ar), 7.34 (ddd, J=8.5, 6.6, 1.1 Hz, 1H, H-6, Ar), 7.74 (dt, J=8.1, 1.0 Hz, 1H, H-4, Ar), 8.04 (d, J=0.9 Hz, 1H, H-3, Ar).

$^{13}$C NMR (75 MHz, $CDCl_3$) δ=35.6 (C-2'), 50.7 (C-1'), 56.0 (C-4"), 94.6 (C-2"), 109.0 (C-7), 116.6 (C-3$^a$, C-5$^a$), 120.5 (C-4), 121.1 (C-5), 124.0 (C-3$^a$), 126.2 (C-6), 129.9 (C-2$^a$, C-6$^a$), 131.9 (C-1$^a$), 133.1 (C-3), 139.6 (C-7a), 156.1 (C-4$^a$)

Example 18

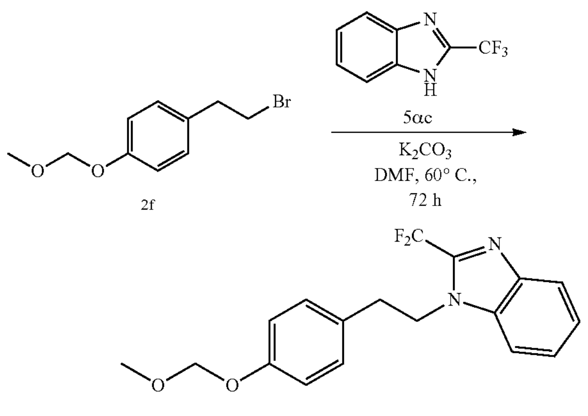

2f

6αaf 1-(4-(Methoxymethoxy)-2-(trifluoromethyl)-1H-benzo[d]imidazole (6αaf). To a vigorous stirred (550 rpm) solution of 2-trifluoromethylbenzimidazole 5αc (0.516 g, 2.77 mmol, 2 eq.) in 4 ml of DMF was added portion-wise potassium carbonate $K_2CO_3$ (0.677 g, 4.89 mmol, 3 eq.). After 30 minutes of magnetic stirring, 1-(2-bromethyl)-4-(methoxymethoxy)benzene 2f (0.34 g, 1.63 mmol, 1 eq.) was added to the reaction mixture and the resulting reaction mixture was stirred at 60° C. for 72 hours (monitored by thin layer chromatography with 0.2 mm plates of silica gel 60-F254 Merck using $CH_2Cl_2$/MeOH 95:5 v/v as eluent). After cooling down to room temperature, 40 ml of deionised water was poured in the reaction mixture and the resulting mixture was transferred into a separating funnel. Extraction was carried out with ethyl acetate (2×20 ml), then the collected extracts were successively washed with brine (3×20 ml), dried over anhydrous $MgSO_4$ and filtered in a filter paper. The filtrate was concentrated using a rotary evaporator under reduced pressure and the crude residue was submitted to purification by chromatography (Combi Flash $R_f$ 200 psi apparatus with a DAD 200/360 nm detector) on pre-packed column of silica gel 60 F-254 (Merck) using a stepwise gradient of cyclohexane/AcOEt (0-20%) for elution. Pooling for 60 minutes and elimination of the solvent in vacuo gave the pure desired compound 6αad as translucent viscous oil in 50% yield.

$^1$H NMR (300 MHz, $CDCl_3$) δ=3.07 (m, 2H, H-2'), 3.46 (s, 3H, H-4"), 4.46 (m, 2H, H-1'), 5.14 (s, 2H, H-2"), 6.97 (m, 2H, H-3$^a$, H-5$^a$, Ar), 7.06 (m, 2H, H-2$^a$, H-6$^a$, Ar), 7.36 (m, 3H, H-5, H-6, H-7, Ar), 7.88 (m, 1H, H-4, Ar).

$^{13}$C NMR (75 MHz, $CDCl_3$) δ=35.7 (C-2'), 46.8 (C-1'), 56.0 (C-4"), 94.5 (C-2"), 110.5 ($CF_3$), 116.8 (C-3$^a$, C-5$^a$), 121.8 (C-4, C-7), 123.7 (C-5, C-6), 125.4 (C-7$^a$), 129.8 (C-2$^a$, C-6$^a$), 130.3 (C-1$^a$), 135.3 (C-3a), 141.2 (C-2), 156.5 (C-4$^a$).

$^{19}$F NMR (282 MHz, $CDCl_3$) δ=62.0

Part 2

The chemical scheme used for the preparation of N-phenylalkyl azole SOCE inhibitors bearing benzimidazole, indazole, pyrazole and triazole platforms with free hydroxyl function on the terminal side chain. is presented in FIG. 2.

Example 19

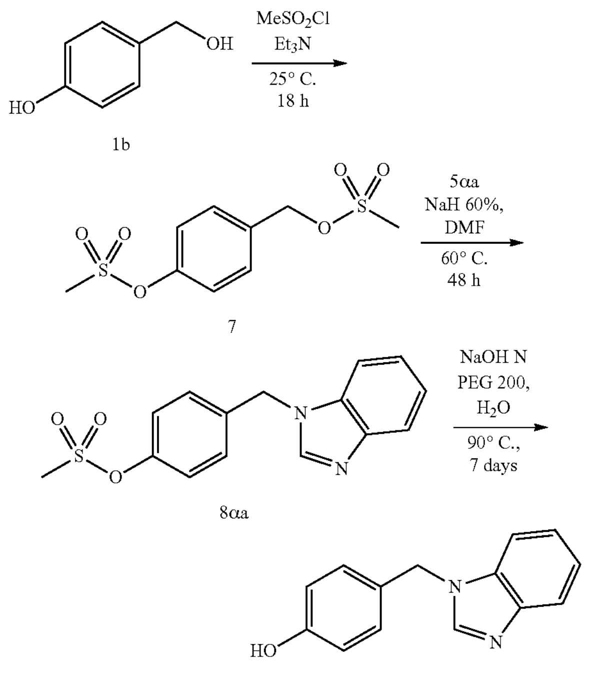

1b

7

8αa

9αa 4-(Methylsulfonyloxy)phenylmethyl methanesulfonate (7). To a vigorous stirred (550 rpm) solution of 4-hydroxyphenylethanol 1b (2 g, 16.11 mmol) in 45 ml of anhydrous methylene chloride cooled at 0° C. (ice bath) was added successively drop-wise triethylamine TEA (4.7 ml, 33.8 mmol, 2.1 eq.) for 10 minutes. This was followed by the slow addition of methanesulfonyl chloride (2.62 ml, 33.8 mmol., 2.1 eq.). After addition has been completed, the reaction mixture was stirred at room temperature for 18 hours. To the reaction mixture was poured deionised water (90 ml) and after 10 minutes of magnetic stirring, the reaction mixture was transferred into a separating funnel. Extraction was conducted with 2×45 ml of $CH_2Cl_2$ and the collected extracts were washed with brine (2×45 ml), dried over anhydrous $MgSO_4$ and filtered on a paper filter. The filtrate was concentrated using a rotary evaporator under reduced pressure and the resulting solid material was dried in vacuo and afforded the desired compound 7 as mobile yellowish oil in 41% yield. The compound 7 was used later without further purification.

$^1$H NMR (300 MHz, DMSO-$d_6$) δ=3.16 (s, 3H, $CH_3$, H-1b), 3.68 (s, 3H, $CH_3$, H-1a), 4.60 (s, 2H, $CH_2$, H-1), 7.29 (m, 2H, H-3', H-5', Ar), 7.46 (m, 2H, H-2', H-6', Ar).

$^{13}$C NMR (75 MHz, DMSO-$d_6$) δ=37.5 (C-$1^a$), 45.1 (C-$1^b$), 52.6 (C-1), 122.3 (C-3', C-5), 130.3 (C-2', C-6'), 136.9 (C-1'), 149.0 (C-4').

HRMS, m/z=302.9973 found (calculated for $C_9H_{12}O_6S_2Na$ $[M+Na]^+$ requires 302.9973).

4-((1H-Benzo[d]imidazol-1-yl)methyl)phenyl methanesulfonate (8αa). To a vigorous stirred (550 rpm) solution of benzimidazole 5αa (0.337 g, 2.85 mmol, 2 eq.) in 4 ml of dry DMF was added portion wise sodium hydride 60% dispersion in mineral oil (0.112 g, 2.85 mmol) and the resulting suspension is stirred for 10 minutes. After addition of 4-(methylsulfonyloxy)phenylmethyl methanesulfonate 7 (0.4 g, 1.43 mmol) in 4 portions, the reaction mixture was heated at 60° C. for 24 hours. After cooling down to room temperature, deionised water (40 ml) was added into the reaction mixture. After progressive formation of a precipitate after standing at 4° C. (refrigerator) for 8 hours, the resulting insoluble material was collected by filtration in a Buchner funnel (porosity No 4), washed successively with 3×5 ml of deionised water, 3×15 ml of cyclohexane and dried under high reduced pressure ($10^{-2}$ Torr) at 25° C. for 30 minutes. The desired product 8αa was obtained as white powder in 47% yield. Mp=104-108° C.

$^1$H NMR (300 MHz, DMSO-$d_6$) δ=3.35 (s, 3H, $CH_3$), 5.55 (s, 2H, $CH_2$, H-1'), 7.22 (m, 2H, H-3", H-5"), 7.33 (m, 2H, H-2", H-6"), 7.43 (m, 2H, H-5, H-6), 7.55 (m, 1H, H-7), 7.67 (m, 1H, H-4), 8.42 (s, 1H, H-2).

$^{13}$C NMR (75 MHz, DMSO-$d_6$) δ=37.4 ($CH_3$), 46.8 (C-1'), 110.6 (C-7), 119.5 (C-4), 121.7 (C-2", C-6"), 122.5 (C-3", C-5"), 129.1 (C-5, C-6), 133.6 (C-1"), 136.2 (C-$7^a$), 143.5 (C-$3^a$), 144.2 (C-2), 148.5 (C-4").

HRMS, m/z=325.0621 found (calculated for $C_{15}H_{14}N_2O_3SNa$ $[M+Na]^+$ requires 325.0617).

1-(4-hydroxyphenylmethyl)-1H-Benzo[d]imidazol (9αa). A solution of PEG 200 (9.8 mg, 0.2 eq) in deionized water (6 ml) was stirred vigorously under magnetic stirring (550 rpm) at 90° C. The pH of reaction mixture was adjusted to pH 10 by addition (0.5 ml) of sodium hydroxide NaOH 1N. After stirring at room temperature during 10 minutes, 4-((1H-benzo[d]imidazol-1-yl)methyl)phenyl methanesulfonate 8αa (0.074 g, 0.245 mmol) was added portion wise and vigorous magnetic stirring at 90° C. was pursued for 7 days (monitored by thin layer chromatography with 0.2 mm plates of silica gel 60-F254 Merck using $CH_2Cl_2$/MeOH 95.5 v/v as eluent). After cooling down to room temperature, deionized water (40 ml) was added directly to the reaction mixture. The resulting mixture was transferred in a separating funnel and extraction was carried out with ethyl acetate (3×30 ml) then, the collected organic extracts were washed with brine (3×30 ml), dried over anhydrous $MgSO_4$ and filtered on a filter paper. The filtrate was concentrated in rotary evaporator under reduced pressure and produced yellowish viscous oil. This later was submitted to purification by chromatography (Combi Flash $R_f$ 200 psi apparatus with a DAD 200/360 nm detector) on pre-packed column of silica gel 60F-254 (Merck) using a stepwise gradient of cyclohexane/AcOEt (0-30%) for elution. Pooling for 60 minutes and elimination of the solvent in vacuo gave the pure desired compound 9αa in 46% yield as white powder. Mp=102-106° C. Mp=242-246° C.

$^1$H NMR (300 MHz, DMSO-$d_6$) δ=5.34 (s, 2H, $CH_2$, H-1'), 6.71 (m, 2H, H-3", H-5", Ar), 7.18 (td, J=6.3, 3.0 Hz, 4H, H-2", H-6", H-5, H-6, Ar), 7.51 (m, 1H, H-7, Ar), 7.63 (m, 1H, H-4, Ar), 8.34 (s, 1H, H-2, Ar), 9.42 (br s, 1H, OH).

$^{13}$C NMR (75 MHz, DMSO-$d_6$) δ=47.3 (C-1'), 110.8, (C-7), 115.3 (C-3", C-5"), 119.4 (C-4), 121.4 (C-5, C-6), 122.2 (C-1"), 127.0 (C-2", C-6"), 133.6 (C-$7^a$), 143.5 (C-$3^a$), 144.0 (C-2), 157.0 (C-4").

HRMS, m/z=247.0840 found (calculated for $C_{14}H_{12}N_2ONa$ $[M+Na]^+$ requires 247.0842).

Example 20

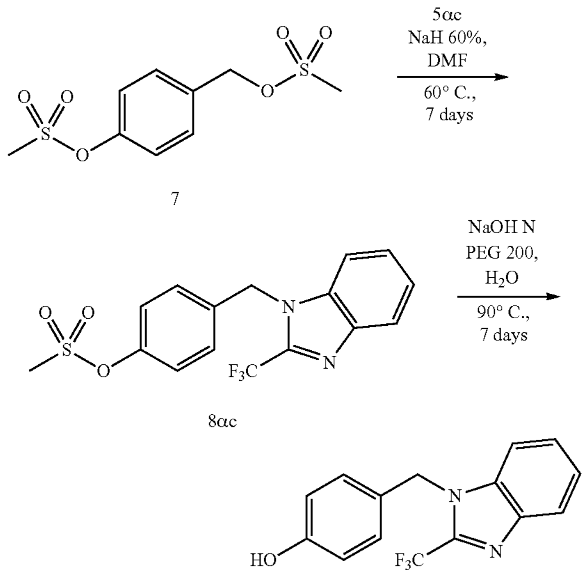

7

8αc

9αc 4-((2-(Trifluoromethyl)-1H-benzo[d]imidazol-1-yl) methyl)phenyl methane sulfonate (8αc). To a vigorous stirred (550 rpm) solution of 2-trifluoromethylbenzimidazole 5αc (0.197 g, 2.85 mmol, 2 eq.) in 4 ml of dry DMF was added portion wise sodium hydride 60% (0.114 g, 2.85 mmol) and the resulting suspension was stirred for 10 minutes. After addition of 4-(methylsulfonyloxy)-phenylmethyl methanesulfonate 7 (0.5 g, 1.78 mmol) in 4 portions, the reaction mixture was heated at 60° C. for 7 days (monitored by thin layer chromatography using 0.2 mm plates of silica gel 60F-254 Merck). After cooling down to room temperature, deionised water (40 ml) was added into the reaction mixture. The reaction mixture was transferred in a separating funnel. Extraction was carried out with 2×30 ml of ethyl acetate and the collected extracts were washed with brine (2×30 ml), dried over anhydrous $MgSO_4$ and filtered on a paper filter. The filtrate was concentrated in rotary evaporator under reduced pressure and the crude residue was submitted to purification (Combi Flash $R_f$ 200 psi apparatus with a DAD 200/360 nm detector) on pre-packed column of silica gel 60F-254 (Merck) using a stepwise gradient of cyclohexane/AcOEt (0-10%) for elution. Pooling for 60 minutes and elimination of the solvent in vacuo gave the pure desired compound 8αc in 36% yield as white powder. Mp=102-106° C.

$^1H$ NMR (300 MHz, DMSO-$d_6$) δ=3.35 (s, 3H, $CH_3$), 5.75 (s, 2H, $CH_2$, H-1'), 7.20 (m, 2H, H-3", H-5"), 7.32 (m, 2H, H-2", H-6"), 7.44 (m, 2H, H-5, H-6), 7.70 (m, 1H, H-7), 7.88 (m, 1H, H-4).

$^{13}C$ NMR (75 MHz, DMSO-$d_6$) δ=37.5 ($CH_3$), 47.0 (C-1'), 112.0 ($CF_3$), 121.0 (C-4, C-7), 122.6 (C-3", C-5"), 123.9 (C-5, C-6), 125.7 (C-2", C-6"), 128.0 (C-1"), 135.2 (C-7a), 135.5 (C-3a), 140.5 (C-2), 148.4 (C-4").

$^{19}F$ NMR (282 MHz, DMSO-$d_6$) δ=−60.7.

HRMS, m/z=393.0493 found (calculated for $C_{16}H_{13}N_2O_3F_3SNa$ $[M+Na]^+$ requires 393.0491).

1-(4-hydroxyphenylmethyl)-2-trifluoromethyl-1H-Benzo[d]imidazol (9αc). Compound 9αc was synthesized from 4-((2-(trifluoromethyl)-1H-benzo[d]imidazol-1-yl)methyl) phenyl methanesulfonate 8αc (0.70 mmol) according to the procedure used for 9αa in Example 16, which afforded the desired compound 9αc in 15% yield as whitish powder. Mp=188-192° C.

$^1H$ NMR (300 MHz, DMSO-$d_6$) δ=5.46 (s, 2H, $CH_2$, H-1'), 6.80 (m, 2H, H-3", H-5"), 7.02 (m, 2H, H-3", H-5"), 7.33 (m, 3H, H-4, H-5, H-7), 7.88 (ddd, J=6.1, 3.2, 0.8 Hz, 1H, H-6).

$^{13}C$ NMR (75 MHz, DMSO-$d_6$) δ=48.3 (C-1'), 111.4 ($CF_3$), 116.1 (C-3", C-5"), 121.7 (C-4, C-7) 124.0 (C-2, C-6), 125.7 (C-1"), 126.9 (C-7a), 128.2 (C-2", C-6"), 135.7 (C-3a), 141.2 (C-2), 156.0 (C-4").

$^{19}F$ NMR (282 MHz, DMSO-$d_6$) δ=−61.4.

HRMS, m/z=315.0717 found (calculated for $C_{15}H_{11}N_2OF_3Na$ $[M+Na]^+$ requires 315.0716).

Example 21

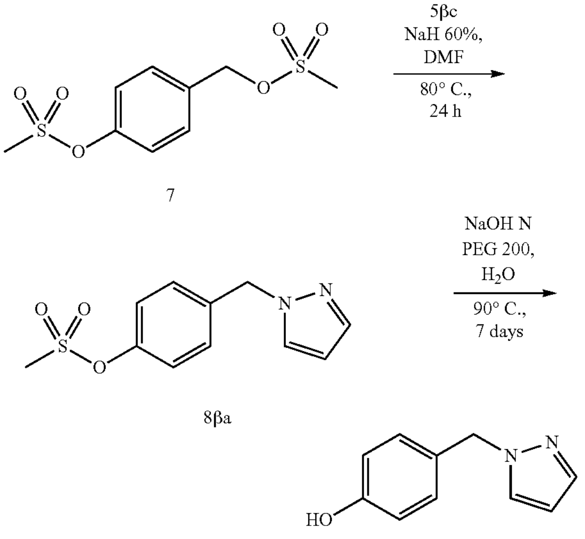

7

8βa

9βa 4-((1H-Pyrazol-1-yl)methyl)phenylmethanesulfonate (8βa). Compound 8βa was synthesized from 4-(methylsulfonyloxy)phenylmethyl methanesulfonate 7 and pyrazole 5βc after a reaction time of 24 hours in 59% yield as white powder according to the procedure used for 8αa in Example 16. Mp=77-80° C.

$^1H$ NMR (300 MHz, DMSO-$d_6$) δ=3.12 (s, 3H, $CH_3$), 5.33 (s, 2H, $CH_2$, H-1'), 6.30 (s, 1H, H-4, Ar), 7.24 (d, J=0.7 Hz, 4H, H-2", H-3", H-5", H-6", Ar), 7.41 (dd, J=2.3, 0.6 Hz, 1H, H-5, Ar), 7.56 (dd, J=1.8, 0.7 Hz, 1H, H-3, Ar).

$^{13}C$ NMR (75 MHz, DMSO-$d_6$) δ=37.6 ($CH_3$), 55.2 (C-1'), 106.4 (C-4), 122.5 (C-3", C-5"), 129.2 (C-1"), 129.5 (C-5), 136.4 (C-2", C-6"), 140.1 (C-3), 148.9 (C-4").

HRMS, m/z=275.0461 found (calculated for $C_{11}H_{12}N_2O_3SNa$ $[M+Na]^+$ requires 275.0461).

1-(4-Hydroxyphenylmethyl)-1H-pyrazole (9βa). Compound 90a was synthesized from 4-((1H-pyrazol-1-yl) methyl)phenylmethanesulfonate 8βca (0.70 mmol) according to the procedure used for 9αa in Example 16, which afforded the desired compound 9βa in 55% yield as whitish powder. Yield=55%. Mp=116-120° C.

$^1H$ NMR (300 MHz, DMSO-$d_6$) δ=5.22 (s, 2H, $CH_2$, H-1'), 6.28 (t, J=2.1 Hz, 1H, H-4), 6.65 (m, 2H, H-3", H-5"), 7.00 (m, 2H, H-2", H-6"), 7.41 (dd, J=2.3, 0.6 Hz, 1H, H-5), 7.57 (dd, J=1.9, 0.7 Hz, 1H, H-3).

$^{13}C$ NMR (75 MHz, DMSO-$d_6$) δ=55.6 (C-1'), 105.9 (C-4), 116.0 (C-3", C-5"), 127.8 (C-1"), 129.3 (C-2", C-6"), 129.7 (C-5), 139.7 (C-3), 156.3 (C-4").

HRMS, m/z=197.0684 found (calculated for $C_{10}H_{10}N_2ONa$ $[M+Na]^+$ requires 197.0685).

Example 22

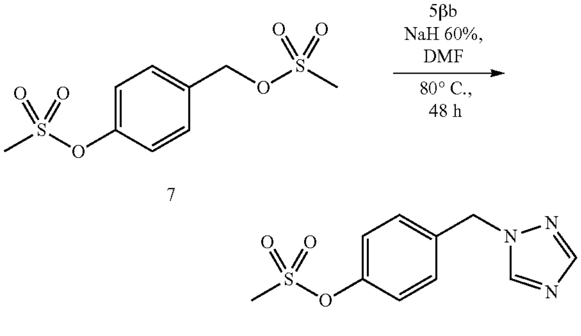

7

8βb 4-((1H-1,2,4-Triazol-1-yl)methyl)phenyl methanesulfonate (8βb). Compound 8βb was synthesized from 4-(methylsulfonyloxy)phenylmethyl methanesulfonate 7 and triazole 5βb after a reaction time of 48 hours in 69% yield as white powder according to the procedure used for 8αa in Example 16. Mp=60-64° C.

$^1H$ NMR (300 MHz, DMSO-$d_6$) δ=3.14 (s, 3H, $CH_3$), 5.36 (s, 2H, $CH_2$, H-1'), 7.30 (d, J=1.8 Hz, 4H, H-2", H-3", H-5", H-6", Ar), 7.98 (s, 1H, H-5), 8.10 (s, 1H, H-3).

$^{13}C$ NMR (75 MHz, DMSO-$d_6$) δ=37.7 ($CH_3$), 52.8 (C-1'), 122.8 (C-3", C-5"), 129.7 (C-1"), 134.2 (C-2", C-6"), 143.3 (C-5), 149.3 ((C-4"), 152.6 (C-3).

HRMS, m/z=276.0415 found (calculated for $C_{10}H_{11}N_3O_3SNa$ $[M+Na]^+$ requires 276.0413).

Example 23

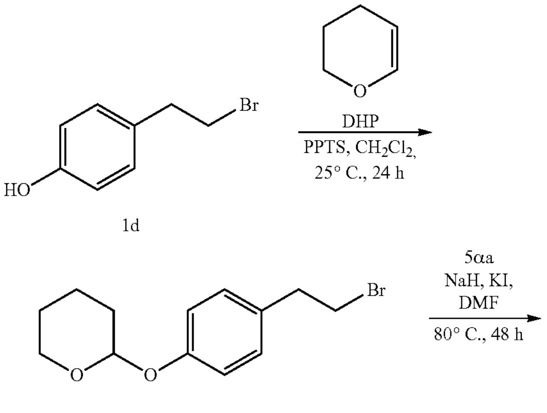

1d

10

-continued

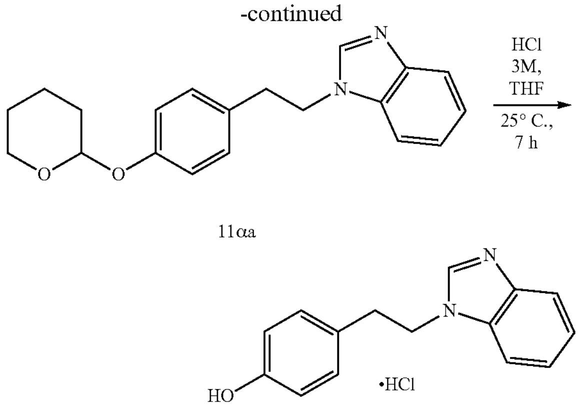

11αa

12αa (DAD4-595)

2-[4-(2-Bromoethyl)phenoxy]tetrahydro-2H-pyran (10). To a solution of 4-hydroxyphenylethyl bromide 1d (3 g, 14.92 mmol, 1 eq.) in 12 ml of $CH_2Cl_2$ was added dropwise 1.5 ml of 3,4-dihydro-2H-pyran DHP (16.41 mmol, 1.1 eq.) under vigorous magnetic stirring for 10 minutes. After 5 supplementary minutes, pyridinium para-toluene sulfonate PPTS (0.375 g, 1.49 mmol., 0.1 eq.) was added portion wise in the reaction mixture. Stirring at room temperature was pursued for 24 hours. The reaction solution was transferred in a separating funnel and the organic layer was washed successively with saturated sodium hydrogenocarbonate $NaHCO_3$ (2x30 ml) and brine (2x30 ml), dried over $MgSO_4$ and filtered on a filter paper. The filtrate was concentrated using a rotary evaporator under reduced pressure and the resulting oily residue was submitted to purification by chromatography (Combi Flash $R_f$ 200 psi apparatus with a DAD 200/360 nm detector) on pre-packed column of silica gel 60F-254 (Merck) using a stepwise gradient of cyclohexane/AcOEt (0-20%) for elution. Pooling for 60 minutes and elimination of the solvent in vacuo gave 3.17 g (56% yield) of the pure desired compound 10 as colorless mobile oil.

$^1H$ NMR (300 MHz, DMSO-$d_6$) δ=1.78 (m, 3H, H-3", H-3", H-4"), 1.99 (m, 2H, H-4", H-2"), ), 2.13 (m, 1H, H-2"), 3.23 (t, J=7.7 Hz, 2H, $CH_2$, H-2), 3.65 (dd, J=8.1, 7.3 Hz, 2H, $CH_2$, H-1), 3.73 (dtd, J=11.4, 4.2, 1.5 Hz, 1H, H-5"), 4.04 (ddd, J=11.5, 9.2, 3.3 Hz, 1H, H-5"), 5.52 (t, J=3.3 Hz, 1H, H-1"), 7.14 (m, 2H, H-3', H-5'), 7.24 (m, 2H, H-2', H-6').

$^{13}C$ NMR (75 MHz, DMSO-$d_6$) δ=18.9 (C-3"), 25.3 (C-4"), 30.5 (C-2"), 33.3 (C-1), 38.8 (C-2), 62.1 (C-5"), 96.5 (C-4"), 116.7 (C-3', C-5'), 129.7 (C-2', C-6'), 132.1 (C-1'), 156.2 (C-4').

HRMS, m/z=307.0312 found (calculated for $C_{13}H_{17}BrO_2Na$ $[M+Na]^+$ requires 307.0310).

1-(4-((Tetrahydro-2H-pyran-2-yl)oxy)phenethyl)-1H-benzo[d]imidazole (11αa). To a solution of benzimidazole 5αa (0.70 mmol, 2 eq.) in 1.2 ml of DMF was added portion-wise NaH 60% dispersion in mineral oil (0.027 g, 0.70 mmole, 2 eq.) under vigorous stirring (500 rpm) for 5 minutes. To this mixture was added successively 2-[4-(2-bromoethyl)phenoxy]tetrahydro-2H-pyran 10 (0.1 g, 0.35 mmol, 1 eq.) and potassium iodide KI (0.006 g, 0.035 mmol, 0.1 eq.), then the resulting reaction mixture was heated at 90° C. for 24 hours. After cooling down to room temperature, 12 ml of deionised water were poured in the reaction mixture and the flask is shaken manually and then stored at 4° C. (refrigerator) for 6 hours until complete precipitation. The insoluble material was recovered by filtration in Buchner funnel (porosity No 4) and the precipitate was washed successively with 3 ml of deionised water, then hexane (3×3 ml). The resulting solid was further dried under high vacuum ($10^{-3}$ Torr) and afforded 0.052 g of the desired compound 11αa as white powder in 46% yield. Mp=101-103° C.

$^1$H NMR (300 MHz, DMSO-$d_6$) δ=1.41-199 (m, 6H, H-3", H-4", H-5"), 3.05 (s, 2H, $CH_2$, H-2'), 3.54 (s, 1H, H-6"), 3.71 (d, J=26.1 Hz, 1H, H-6"), 4.45 (s, 2H, $CH_2$, H-1'), 5.39 (s, 1H, H-1"), 6.91 (d, J=7.8 Hz, 2H, H-$3^a$, H-$5^a$, Ar), 7.08 (d, J=7.7 Hz, 2H, H-$2^a$, H-$6^a$, Ar), 7.31-7.13 (m, 2H, H-6, H-7, Ar), 7.62 (d, J=6.5 Hz, 2H, H-5, H-8, Ar), 8.04 (s, 1H, H-2, Ar).

$^{13}$C NMR (75 MHz, DMSO-$d_6$) δ=18.7 (C-4"), 24.7 (C-3"), 29.9 (C-5"), 34.6 (C-6"), 45.6 (C-2'), 61.6 (C-1'), 95.9 (C-1'"), 110.5 (C-5), 116.4 (C-$3^a$, C-$5^a$), 119.4 (C-8), 121.4 (C-6), 122.2 (C-7), 129.6 (C-$2^a$, C-$6^a$), 131.0 (C-$1^a$), 133.7 (C-9), 143.3 (C-4), 143.9 (C-2), 155.2 (C-$4^a$).

HRMS m/z=345.1573 found (calculated for $C_{20}H_{22}N_2O_2Na$ $[M+Na]^+$ requires 345.1574), 323.1754 found (calculated for $C_{20}H_{23}N_2O_2$ $[M+H]^+$ requires 323.1754), 261.0998 found (calculated for $C_{15}H_{14}N_2ONa$ $[M-C_5H_8O+Na]^+$ requires 323.1754).

1-(4-Hydroxyphenylethyl)-1H-benzo[d]imidazol hydrochloride (12αa). To a solution of 1-(4-((tetrahydro-2H-pyran-2-yl)oxy)phenethyl)-1H-benzo[d]imidazole 11αa (0.11 mmol, 1 eq.) in 0.33 ml of tetrahydrofurane was added dropwise 0.33 ml of 3M HCl, then the reaction is stirred under magnetic stirring at room temperature during 5 h (monitored by thin layer chromatography using 0.2 mm plates of silica gel 60-F254 Merck using cyclohexane/AcOEt 1:1 v/v or $CH_2Cl_2$/MeOH 9:1 v/v as eluent). The solution was concentrated in rotary evaporator under reduced pressure and the resulting solid was triturated in 1 ml of dry acetone (or eventually stirred for 15 minutes.). The insoluble material was recovered by filtration on Buchner funnel (porosity No 4) and washed with dry acetone (3×0.5 ml). The solid was further dried under high vacuum ($10^{-3}$ Torr) for 10 minutes and afforded 0.025 g of the desired compound 12αa as white powder in 83% yield. Mp=212-214° C.

$^1$H NMR (300 MHz, DMSO-$d_6$) δ=3.11 (t, J=7.2 Hz, 2H, $CH_2$, H-2'), 4.68 (t, J=7.1 Hz, 2H, $CH_2$, H-1'), 6.65 (d, J=8.4 Hz, 2H, H-$3^a$, H-$5^a$, Ar), 6.95 (d, J=8.3 Hz, 2H, H-$2^a$, H-$6^a$, Ar), 7.67-7.49 (m, 2H, H-5, H-8, Ar), 8.09-7.73 (m, 2H, H-6, H-7, Ar), 9.43 (s, 1H, H-2).

$^{13}$C NMR (75 MHz, DMSO-$d_6$) δ=33.8 (C-2'), 47.8 (C-1'), 113.3 (C-5), 115.1 (C-$1^a$), 115.3 (C-$3^a$, C-$5^a$), 125.9 (C-8), 126.2 (C-6), 126.9 (C-7), 129.7 (C-$2^a$, C-$6^a$), 131.0 (C-9), 131.3 (C-4), 141.4 (C-2), 156.2 (C-$4^a$).

HRMS m/z=261.1001 found (calculated for $C_{15}H_{14}N_2ONa$ $[M+Na]^+$ requires 261.0998), 239.1182 found (calculated for $C_{15}H_{15}N_2O$ $[M+H]^+$ requires 239.1179).

Example 24

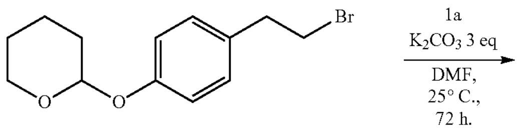

10

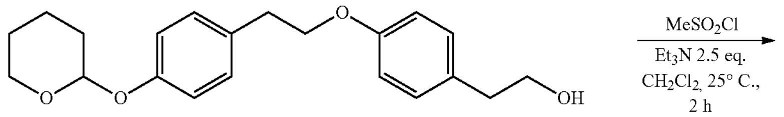

3k

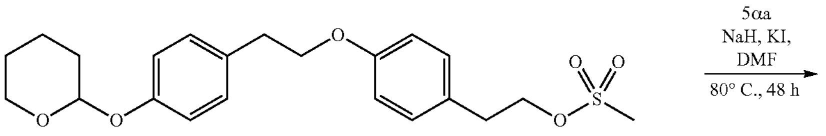

4k

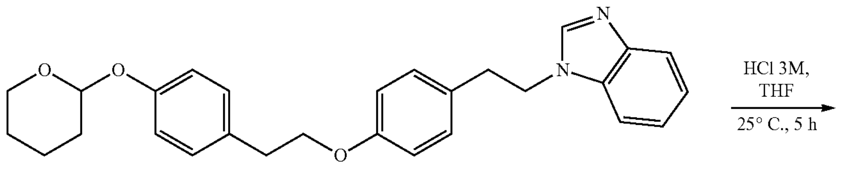

11αb

-continued

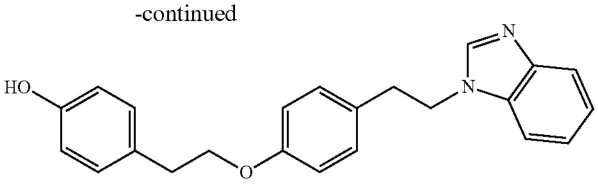

12αb (DAD4-609)

2-(4-(4-((Tetrahydro-2H-pyran-2-yl)oxy)phenethoxy) phenyl)ethan-1-ol (3k). To a solution of 2-(4-hydrophenyl) ethanol 1a (0.5 g, 3.62 mmol) in 2 ml of dry DMF under vigorous magnetic stirring (550 rpm) was added in several portions 1.5 g of potassium carbonate $K_2CO_3$ (10.86 mmol, 3 equiv.) at room temperature. After 30 minutes, a solution of 2-[4-(2-bromoethyl)phenoxy]tetrahydro-2H-pyran 10 (1.02 g, 4.34 mmol, 1.2 eq.) in 1.5 ml of DMF was added dropwise during 15 minutes at 25° C. and stirring is pursued during 72 hours (monitored by thin layer chromatography with 0.2 mm plates of silica gel 60-F254 Merck using cyclohexane/AcOEt 1:1 v/v as eluent). Deionised water (20 ml) was added directly in the crude reaction mixture and the resulting solution was transferred in a separating funnel. Extraction was conducted AcOEt (3×25 ml) and the organic layer was washed successively with deionised water (2×25 ml) and brine (2×25 ml), dried over $MgSO_4$ and filtered on a filter paper. The filtrate was concentrated in rotary evaporator under reduced pressure and the resulting oily residue was submitted to purification by chromatography (Combi Flash $R_f$ 200 psi apparatus with a DAD 200/360 nm detector) on pre-packed column of silica gel 60F-254 (Merck) using a stepwise gradient of cyclohexane/AcOEt (0-50%) for elution. Pooling for 60 minutes and elimination of the solvent in vacuo gave 0.455 g (36% yield) of the pure desired compound 3k as colorless mobile oil.

$^1$H NMR (300 MHz, DMSO-$d_6$) δ=1.94-1.45 (m, 6H, $CH_2$, H-3", H-4", H-5"), 2.64 (t, J=7.1 Hz, 2H, $CH_2$, H-2'), 2.94 (t, J=6.9 Hz, 2H, $CH_2$, H-2), 3.53 (tt, J=9.5, 4.7 Hz, 3H, CH, $CH_2$, H-1', H-1"), 3.82-3.69 (m, 1H, 1"), 4.10 (t, J=6.9 Hz, 2H, $CH_2$, H-1), 4.58 (t, J=5.2 Hz, 1H, OH), 5.41 (t, J=3.2 Hz, 1H, H-1"), 6.86-6.75 (m, 2H, H-3$^a$, H-5$^a$, Ar), 7.00-6.89 (m, 2H, H-3$^b$, H-5$^b$, Ar), 7.15-7.04 (m, 2H, H-2$^a$, H-6$^a$, Ar), 7.28-7.16 (m, 2H, H-2$^b$, H-6$^b$, Ar).

$^{13}$C NMR (75 MHz, DMSO-$d_6$) δ=18.7 (C-4"), 24.7 (C-3"), 29.9 (C-5"), 34.2 (C-6"), 38.2 (C-2'), 61.5 (C-2), 62.4 (C-1'), 68.3 (C-1), 95.9 (C-1"), 114.2 (C-3$^a$, C-5$^a$), 116.4 (C-3$^b$, C-5$^b$), 129.8 (C-2$^a$, C-6$^a$, C-2$^b$, C-6$^b$), 131.4 (C-1$^b$), 131.4 (C-1$^a$), 155.1 (C-4$^a$), 156.7 (C-4$^b$).

HRMS m/z=365.1726 found (calculated for $C_{21}H_{26}O_4Na$ $[M+Na]^+$ requires 365.1723), 381.1465 found (calculated for $C_{21}H_{26}O_4K$ $[M+K]^+$ requires 381.1463), 281.1153 found (calculated for $C_{16}H_{18}SO_3Na$ $[M-C_5H_8O+Na]^+$ requires 281.1148).

4-(4-((Tetrahydro-2H-pyran-2-yl)oxy)phenethoxy)phenethyl methanesulfonate (4k). To a solution cooled at 0° C. (ice bath) of 2-(4-(4-((tetrahydro-2H-pyran-2-yl)oxy) phenethoxy)phenyl)ethan-1-ol 3k (0.48 g, 1.37 mmol, 1 eq.) in anhydrous $CH_2Cl_2$ (4.7 ml) was added drop-wise alternatively a solution of methanesulfonyl chloride (220 μl, 0.326 g, 2.84 mmol, 2.07 eq.) in 0.7 ml of dry $CH_2Cl_2$ and 483 μl of triethylamine TEA (0.379 g, 3.75 mmol, 2.7 eq.) for 15 minutes. Then, the resulting reaction mixture was stirred at room temperature for 2 hours (monitored by thin layer chromatography with 0.2 mm plates of silica gel 60-F254 Merck using cyclohexane/AcOEt 1:1 v/v as eluent). Work-up was carried out according to the procedure used for 4a in Example 1, which afforded 0.339 g of the desired compound 4k (57% yield) as yellowish mobile oil.

$^1$H NMR (300 MHz, DMSO-$d_6$) δ=1.94-1.41 (m, 6H, H-3", H-4", H-5"), 3.01-2.83 (m, 4H, $CH_2$, H-2', H-2"), 3.09 (s, 3H, $SCH_3$), 3.60-3.45 (m, 1H, CH, H-6"), 3.83-3.68 (m, 1H, CH, H-6"), 4.12 (t, J=6.9 Hz, 2H, $CH_2$, H-1'), 4.35 (t, J=6.8 Hz, 2H, $CH_2$, H-1), 5.42 (t, J=3.1 Hz, 1H, CH, H-1"), 6.91-6.82 (m, 2H, H-3$^a$, H-5$^a$, Ar), 6.99-6.92 (m, 2H, H-3$^b$, H-5$^b$, Ar), 7.21 (dd, J=10.9, 8.6 Hz, 4H, H-2$^a$, H-6$^a$, H-2$^b$, H-6$^b$, Ar).

$^{13}$C NMR (75 MHz, DMSO-$d_6$) δ=18.7 (C-4"), 24.7 (C-3"), 29.9 (C-5"), 34.2 (C-6"), 38.2 (C-2'), 61.5 (C-2), 62.4 (C-1'), 68.3 (C-1), 95.9 (C-1"), 114.2 (C-3$^a$, C-5$^a$), 116.4 (C-3$^b$, C-5$^b$), 129.8 (C-2$^a$, C-6$^a$, C-2$^b$, C-6$^b$), 131.4 (C-1$^b$), 131.4 (C-1$^a$), 155.1 (C-4$^a$), 156.7 (C-4$^b$).

HRMS m/z=443.1498 found (calculated for $C_{22}H_{28}O_6NaS$ $[M+Na]^+$ requires 443.1499), 459.1233 found (calculated for $C_{22}H_{28}O_6SK$ $[M+K]^+$ requires 459.1238).

1-(4-(4-((Tetrahydro-2H-pyran-2-yl)oxy)phenethoxy) phenethyl)-1H-benzo[d]imidazole (11αb). Compound 11αb was synthesized from benzimidazole 5αa (0.76 mmol., 2 eq.) and 4-(4-((tetrahydro-2H-pyran-2-yl)oxy)phenethoxy) phenethyl methanesulfonate 4k (0.16 g, 0.38 mmol, 1 eq.) according to the procedure used for 11αa in Example 23, which afforded 0.048 g of the desired compound 11αb (28% yield) as white powder.

$^1$H NMR (300 MHz, DMSO-$d_6$) δ=1.69 (dddd, J=25.8, 16.9, 15.9, 8.3 Hz, 6H, $CH_2$, H-3''', H-4''', H-5'''), 2.93 (t, J=6.7 Hz, 2H, $CH_2$, H-2"), 3.04 (t, J=7.1 Hz, 2H, $CH_2$, H-2'), 3.59-3.45 (m, 1H, H-6'''), 3.85-3.67 (m, 1H, H-6'''), 4.08 (t, J=6.8 Hz, 2H, $CH_2$, H-1"), 4.44 (t, J=7.1 Hz, 2H, $CH_2$, H-1'), 5.41 (s, 1H, H-1'''), 6.81 (d, J=8.4 Hz, 2H, H-3$^a$, H-5$^a$, Ar), 6.96 (d, J=8.4 Hz, 2H, H-3$^b$, H-5$^b$, Ar), 7.06 (d, J=8.4 Hz, 2H, H-2$^a$, H-6$^a$, Ar), 7.28-7.13 (m, 4H, H-6, H-7, H-2$^b$, H-6$^b$, Ar), 7.63 (dd, J=12.3, 5.8 Hz, 2H, H-5, H-8, Ar), 8.01 (s, 1H, H-2, Ar).

$^{13}$C NMR (75 MHz, DMSO-$d_6$) δ=18.7 (C-4'''), 24.7 (C-3'''), 29.9 (C-5'''), 34.1 (C-6'''), 34.5 (C-2"), 45.6 (C-2'), 61.5 (C-1"), 68.3 (C-1'), 95.9 (C-1'''), 110.4 (C-5), 114.4 (C-3$^a$, C-5$^a$), 116.4 (C-3$^b$, C-5$^b$), 119.4 (C-8), 121.3 (C-6), 122.2 (C-7), 129.7 (C-2a, C-6$^a$), 129.8 (C-2$^b$, C-6$^b$), 130.0 (C-1$^a$), 131.3 (C-1$^b$), 133.6 (C-9), 143.3 (C-4), 143.9 (C-2), 155.1 (C-4$^a$), 157.1 (C-4$^b$).

HRMS m/z=465.2144 found (calculated for $C_{28}H_{30}N_2O_3Na$ $[M+Na]^+$ requires 465.2149), 443.2328 found (calculated for $C_{28}H_{31}N_2O_3$ $[M+H]^+$ requires 443.2329), 481.1887 found (calculated for $C_{28}H_{30}N_2O_3K$ $[M+K]^+$ requires 481.1888).

1-(4-(4-Hydroxyphenethoxy)phenethyl)-1H-benzo[d] imidazol hydrochloride (12αb). Compound 12αb was synthesized from 11αb (0.11 mmol) according to the procedure used for 12αa in example 23, which afforded 0.028 g of the desired compound 12αb (72% yield) as brown powder. Mp=97-107° C.

$^{1}H$ NMR (300 MHz, DMSO-$d_6$) δ=2.87 (t, J=6.8 Hz, 2H, $CH_2$, H-2"), 3.16 (t, J=7.0 Hz, 2H, $CH_2$, H-2'), 4.04 (t, J=6.9 Hz, 2H, $CH_2$, H-1"), 4.70 (t, J=7.1 Hz, 2H, $CH_2$, H-1'), 6.70 (d, J=8.3 Hz, 2H, H-$3^b$, H-$5^b$, Ar), 6.81 (d, J=8.4 Hz, 2H, H-$3^a$, H-$5^a$, Ar), 7.07 (d, J=8.3 Hz, 4H, H-$2^a$, H-$6^a$, H-$2^b$, H-$6^b$, Ar), 7.59 (dd, J=6.0, 3.1 Hz, 2H, H-5, H-6, A), 7.85 (dd, J=6.0, 2.7 Hz, 1H, H-7, Ar), 8.00 (dd, J=6.2, 2.7 Hz, 1H, H-8, Ar), 9.47 (s, 1H, H-2, Ar).

HRMS m/z=359.1759 found (calculated for $C_{23}H_{23}N_2O_2$ $[M+H]^+$ requires 359.1754).

Example 25 found (calculated for $C_{28}H_{30}N_2O_3F$ $[M+H]^+$ requires 461.2235), 499.1793 found (calculated for $C_{28}H_{29}N_2O_3FK$ $[M+K]^+$ requires 499.1794).

5-Fluoro-1-(4-(4-hydroxyphenethoxy)phenethyl)-1H-benzo[d]imidazol hydrochloride (12αc). Compound 12αc was synthesized from 11αc (0.11 mmol) according to the procedure used for 12αa in Example 23, which afforded 0.028 g of the desired compound 12αc (41% yield) as white powder. Mp=158-160° C.

$^{1}H$ NMR (300 MHz, DMSO-$d_6$) δ=2.87 (t, J=6.9 Hz, 2H, $CH_2$, H-2"), 3.13 (t, J=7.1 Hz, 2H, $CH_2$, H-2'), 4.05 (t, J=6.9 Hz, 2H, $CH_2$, H-1"), 4.66 (dd, J=15.6, 7.8 Hz, 2H, $CH_2$, H-1'), 6.70 (d, J=8.5 Hz, 2H, H-$3^b$, H-$5^b$, Ar), 6.81 (d, J=8.6 Hz, 2H, H-$3^a$, H-$5^a$, Ar), 7.08 (dd, J=8.4, 4.6 Hz, 4H, H-$2^a$,

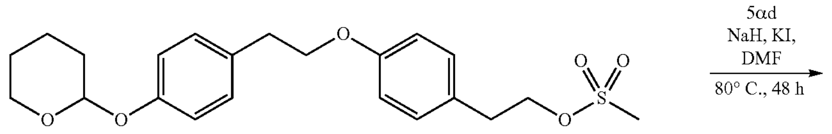

4k

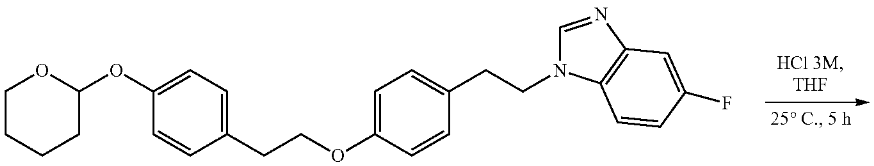

11αc

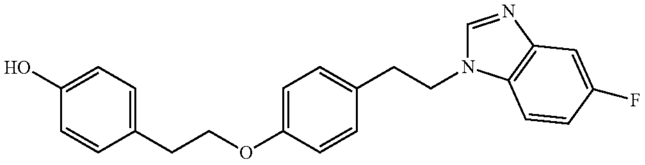

12αc (DAD4-610)

5-Fluoro-1-(4-(4-((tetrahydro-2H-pyran-2-yl)oxy) phenethoxy)phenethyl)-1H-benzo[d]imidazole (11αc). Compound 11αc was synthesized from 5-fluorobenzimidazole 5αd (0.76 mmol, 2 eq.) and 4-(4-((tetrahydro-2H-pyran-2-yl)oxy)phenethoxy)phenethyl methanesulfonate 4k (0.16 g, 0.38 mmol, 1 eq.) according to the procedure used for 11αa in Example 23, which afforded 0.111 g of the desired compound 11αc (63% yield) as white powder. Mp=90-92° C.

$^{1}H$ NMR (300 MHz, DMSO-$d_6$) δ=1.95-1.46 (m, 6H, $CH_2$, H-3'", H-4'", H-5'"), 2.92 (dd, J=12.4, 5.5 Hz, 2H, $CH_2$, H-2"), 3.02 (td, J=7.2, 2.8 Hz, 2H, $CH_2$, H-2'), 3.52 (dt, J=22.2, 8.1 Hz, 1H, H-6'"), 3.82-3.66 (m, 1H, H-6'"), 4.09 (t, J=6.9 Hz, 2H, $CH_2$, H-1'), 4.43 (q, J=7.6 Hz, 2H, $CH_2$, H-1"), 5.42 (dd, J=8.4, 5.0 Hz, 1H, H-1'"), 6.81 (d, J=7.9 Hz, 2H, H-$3^b$, H-$5^b$, Ar), 7.00-6.86 (m, 2H, H-$3^a$, H-$5^a$, Ar), 7.13-7.00 (m, 3H, H-$2^b$, H-$6^b$, H-8, Ar), 7.26-7.13 (m, 2H, H-$2^a$, H-$6^a$, Ar), 7.46 (ddd, J=28.0, 9.6, 2.5 Hz, 1H, H-7, Ar), 7.62 (dt, J=8.9, 5.1 Hz, 1H, H-5, Ar), 8.06 (d, J=11.1 Hz, 1H, H-2, Ar).

HRMS m/z=483.2056 found (calculated for $C_{28}H_{29}N_2O_3FNa$ $[M+Na]^+$ requires 483.2054), 461.2235

H-$6^a$, H-$2^b$, H-$6^b$, Ar), 7.46 (td, J=9.3, 2.4 Hz, 1H, H-8, Ar), 7.88 (dddd, J=49.2, 11.0, 8.9, 3.4 Hz, 2H, H-6, H-7, Ar), 9.36 (d, J=3.4 Hz, 1H, H-2).

HRMS m/z=399.1471 found (calculated for $C_{23}H_{21}N_2O_2FNa$ $[M+Na]^+$ requires 399.1479), 377.1659 found (calculated for $C_{23}H_{22}N_2O_2F$ $[M+H]^+$ requires 377.1660).

Example 26

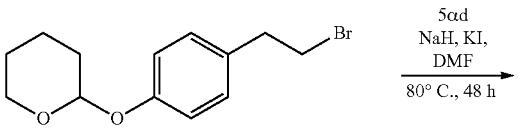

10

-continued

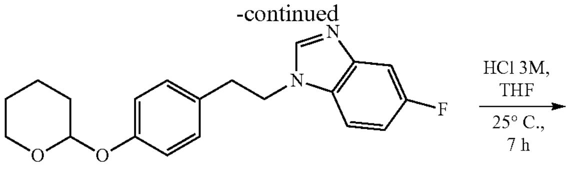

11αd

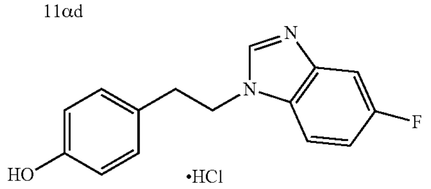

12αd (DAD4-592)

5-Fluoro-1-(4-((tetrahydro-2H-pyran-2-yl)oxy)phenethyl)-1H-benzo[d]imidazole (11αd). Compound 11αd was synthesized from 5-fluorobenzimidazole 5αd (0.70 mmol, 2 eq.) and 2-[4-(2-bromoethyl)phenoxy]tetrahydro-2H-pyran 10 (0.1 g, 0.35 mmol, 1 eq.) according to the procedure used for 11αa in Example 23, which afforded 0.047 g of the desired compound 11αd (39% yield) as yellowish oil.

$^1$H NMR (300 MHz, DMSO-$d_6$) δ=1.86-1.42 (m, 6H, $CH_2$, H-3", H-4", H-5"), 3.02 (tt, J=17.8, 8.9 Hz, 2H, $CH_2$, H-2'), 3.52 (dd, J=9.3, 5.4 Hz, 1H, H-6"), 3.81-3.66 (m, 1H, H-6"), 4.44 (dd, J=14.8, 7.7 Hz, 2H, $CH_2$, H-1'), 5.38 (t, J=3.2 Hz, 1H, CH, H-1"), 6.89 (d, J=8.4 Hz, 2H, H-3$^a$, H-5$^a$, Ar), 7.15-6.95 (m, 3H, H-8, H-2$^a$, H-6$^a$, Ar), 7.45 (ddd, J=23.3, 9.6, 2.4 Hz, 1H, H-5, Ar), 7.61 (ddd, J=8.8, 4.8, 2.5 Hz, 1H, H-7, Ar), 8.08 (d, J=11.1 Hz, 1H, H-2).

$^{13}$C NMR (75 MHz, DMSO-$d_6$) δ=18.8 (C-4"), 24.8 (C-3"), 30.0 (C-5"), 34.7 (C-6"), 45.9 (C-2'), 61.6 (C-1'), 95.9 (C-1'"), 111.4, 116.4 (C-3$^a$, C-5$^a$), 129.7 (C-2$^a$), 129.8 (C-6$^a$), 131.0, 145.6 (C-2), 155.3 (C-4$^a$).

$^{19}$F NMR (282 MHz, DMSO-$d_6$) δ=−119.7-119.9 (m), −121.9-122.1 (m).

HRMS m/z=363.1482 found (calculated for $C_{20}H_{21}N_2O_2FNa$ [M+Na]$^+$ requires 363.1479), 341.1660 found (calculated for $C_{20}H_{22}N_2O_2F$ [M+H]$^+$ requires 341.1660), 379.1219 found (calculated for $C_{20}H_{21}N_2O_2FK$ [M+K]$^+$ requires 379.1219).

5-Fluoro-1-(4-hydroxyphenylethyl)-1H-benzo[d]imidazol hydrochloride (12αd). Compound 12αd was synthesized from 11αd (0.11 mmol) according to the procedure used for 12αa in Example 23, which afforded 0.017 g of the desired compound 12αd (47% yield) as beige powder. Mp=217-219° C.

$^1$H NMR (300 MHz, DMSO-$d_6$) δ=3.09 (dd, J=15.5, 8.4 Hz, 2H, $CH_2$, H-2'), 4.63 (dd, J=15.5, 7.4 Hz, 2H, $CH_2$, H-1'), 6.64 (d, J=8.4 Hz, 2H, H-3$^a$, H-5$^a$, Ar), 7.00-6.89 (m, 2H, H-2$^a$, H-6$^a$, Ar), 7.44 (qd, J=9.6, 2.4 Hz, 1H, H-8, Ar), 7.86 (dddd, J=48.3, 11.1, 8.9, 3.4 Hz, 2H, H-5, H-7, Ar), 9.28 (d, J=3.0 Hz, 1H, H-2, Ar).

$^{13}$C NMR (75 MHz, DMSO-$d_6$) δ=33.9 (C-1'), 47.7 (C-2'), 100.1, 102.2, 114.7 (C-8), 115.3 (C-2$^a$, C-6$^a$), 117.2 (C-5), 127.0 (C-9), 128.2 (C-1$^a$), 129.7 (C-3$^a$, C-5$^a$), 129.7 (C-7), 143.0 (C-2), 156.2 (C-4$^a$).

$^{19}$F NMR (282 MHz, DMSO-$d_6$) δ=−119.8 (m), −121.9-122.1 (m).

HRMS m/z=279.0903 found (calculated for $C_{15}H_{13}N_2OF$ Na [M+Na]$^+$ requires 279.0904), 257.1084 found (calculated for $C_{15}H_{14}N_2OF$ [M+H]$^+$ requires 257.1085), 121.0648 found (calculated for $C_8H_9O$ [$C_8H_8O$+H]$^+$ requires 121.0648).

Example 27

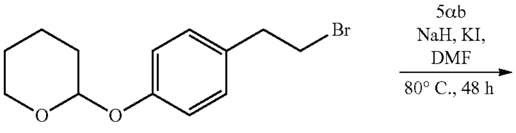

10

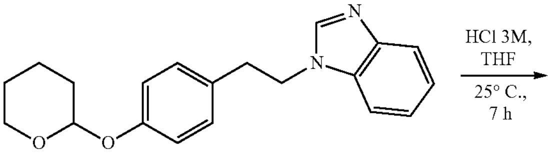

11αe

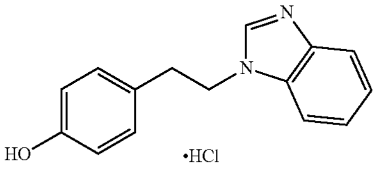

12αe 1-(4-((Tetrahydro-2H-pyran-2-yl)oxy)phenethyl)-1H-indazole (11αe). Compound 11αe was synthesized from indazole 5αb (0.70 mmol, 2 eq.) and 2-[4-(2-bromoethyl)phenoxy]tetrahydro-2H-pyran 10 (0.1 g, 0.35 mmol, 1 eq.) according to the procedure used for 11αa in Example 23, and purification was carried out by chromatography (Combi Flash $R_f$200 psi apparatus with a DAD 200/360 nm detector) on pre-packed column of silica gel 60-F254 (Merck) using a stepwise gradient of cyclohexane/AcOEt (0-25%) for elution. Pooling for 60 minutes and elimination of the solvent in vacuo gave the pure desired compound 11αe in 25% yield as ivory powder. Mp=86-90° C.

$^1$H NMR (300 MHz, DMSO-$d_6$) δ=1.65 (dddd, J=18.4, 11.4, 8.7, 4.7 Hz, 4H, H-3$^a$, H-4$^a$), 1.85 (tt, J=6.4, 2.3 Hz, 1H, H-2$^a$), 1.99 (m, 1H, H-2$^a$), 3.16 (m, 2H, $CH_2$, H-2'), 3.58 (dtd, J=11.4, 4.2, 1.6 Hz, 1H, H-5$^a$), 3.90 (ddd, J=11.4, 9.2, 3.3 Hz, 1H, H-5$^a$), 4.56 (m, 2H, $CH_2$, H-1'), 5.36 (t, J=3.3 Hz, 1H, H-1$^a$), 6.94 (m, 2H, H-3", H-5"), 7.05 (m, 2H, H-2", H-6"), 7.11 (ddd, J=7.9, 6.5, 1.2 Hz, 1H, H-5), 7.28 (m, 2H, H-6, H-7), 7.71 (dt, J=8.1, 1.0 Hz, 1H, H-4), 8.01 (d, J=0.9 Hz, 1H, H-3).

$^{13}$C NMR (75 MHz, DMSO-$d_6$) δ=19.0 (C-3$^a$), 25.4 (C-4$^a$), 30.5 (C-2$^a$), 35.7 (C-2'), 50.8 (C-1'), 62.2 (C-5$^a$), 96.6 (C-1$^a$), 109.1 (C-7), 115.6, 116.8 (C-3", C-5"), 120.6 (C-5), 121.2 (C-4), 124.0 (C-3$^a$), 126.3 (C-6), 129.8 (C-2", C-6"), 131.5 (C-1"), 133.1 (C-3), 139.6 (C-7$^a$), 156.0 (C-4").

1-(4-Hydroxyphenylethyl)-1H-indazole hydrochloride (12αe). Compound 12αe was synthesized from 11αe (0.11 mmol) according to the procedure used for 12αa in example 23, which afforded the desired compound 12αe in 21% yield as beige powder. Mp=217-219° C.

$^1$H NMR (300 MHz, DMSO-$d_6$) δ=3.00 (t, J=7.3 Hz, 2H, $CH_2$, H-2'), 4.54 (t, J=7.3 Hz, 2H, $CH_2$, H-1'), 6.60 (d, J=8.1 Hz, 2H, H-3", H-5", Ar), 6.95 (d, J=8.0 Hz, 2H, H-2", H-6",

Ar), 7.08 (t, J=7.4 Hz, 1H, H-5), 7.30 (t, J=7.6 Hz, 1H, H-6), 7.54 (d, J=8.5 Hz, 1H, H-7), 7.72 (d, J=8.1 Hz, 1H, H-4), 8.05 (s, 1H, H-3).

$^{13}$C NMR (75 MHz, DMSO-$d_6$) δ=34.8 (C-2'), 49.8 (C-1'), 109.7 (C-7), 115.1 (C-3", C-5"), 120.3 (C-4), 120.8 (C-5), 123.4 (C-7a), 125.9 (C-6), 128.5 (C-1"), 129.7 (C-2", C-6"), 132.6 (C-3), 139.3 (C-7a), 155.9 (C-4").

Example 28

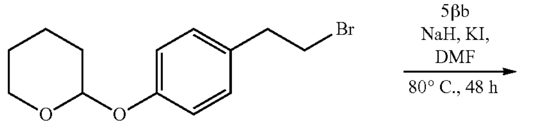

10

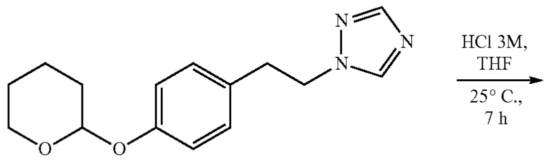

11βa

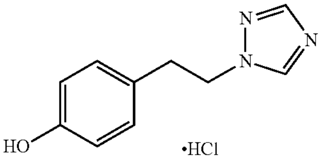

12βa 1-(4-((Tetrahydro-2H-pyran-2-yl)oxy)phenethyl)-1H-1,2,4-triazole (11βa). Compound 11βa was synthesized from 1H-1,2,4-triazole 5βd (0.70 mmol, 2 eq.) and 2-(4-(2-bromoethyl)phenoxy)tetrahydro-2H-pyran 10 (0.1 g, 0.35 mmol, 1 eq.) according to the procedure used for 11αa in example 23, which afforded the desired compound 12βa in 70% yield as whitish powder. Mp=56-60° C.

$^1$H NMR (300 MHz, DMSO-$d_6$) δ=1.63 (m, 3H, $CH_2$, H-3$^a$, H-4$^a$), 1.83 (tt, J=5.3, 2.5 Hz, 2H, H-4$^a$, H-2$^a$), 1.96 (dt, J=9.6, 6.7 Hz, 1H, H-2$^a$), 3.09 (t, J=7.0 Hz, 2H, $CH_2$, H-2'), 3.57 (dtd, J=11.2, 4.2, 1.6 Hz, 1H, H-5$^a$), 3.88 (ddd, J=12.1, 9.1, 3.2 Hz, 1H, H-5$^a$), 4.33 (t, J=7.0 Hz, 2H, $CH_2$, H-1'), 5.35 (t, J=3.4 Hz, 1H, H-1$^a$), 6.93 (m, 4H, H-2", H-3", H-5", H-6"), 7.74 (s, 1H, H-5), 7.93 (s, 1H, H-3).

$^{13}$C NMR (75 MHz, DMSO-$d_6$) δ=18.9 (C-3$^a$), 25.3 (C-4$^a$), 30.5 (C-2$^a$), 35.5 (C-2'), 51.4 (C-1'), 62.2 (C-5$^a$), 96.6 (C-1$^a$), 116.9 (C-3", C-5"), 129.6 (C-2", C-6"), 130.2 (C-1"), 143.3 (C-5), 152.1 (C-3), 156.2 (C-4").

1-(4-Hydroxyphenylethyl)-1H-1,2,4-triazole hydrochloride (12βa). Compound 12βa was synthesized from 11βa (0.11 mmol) according to the procedure used for 12αa in example 23 which afforded the desired compound 120a in 70% yield as whitish powder. Mp=172-176° C.

$^1$H NMR (300 MHz, DMSO-$d_6$) δ=2.98 (t, J=7.1 Hz, 2H, $CH_2$, H-2'), 4.38 (t, J=7.2 Hz, 2H, $CH_2$, H-1'), 6.64 (m, 2H, H-3", H-5"), 6.91 (m, 2H, H-2", H-6"), 8.15 (s, 1H, H-2), 8.58 (s, 1H, H-5).

$^{13}$C NMR (75 MHz, DMSO-$d_6$) δ=34.4 (C-2'), 50.5 (C-1'), 115.2 (C-3", C-5"), 127.5 (C-1"), 129.5 (C-2", C-6"), 149.8 (C-2), 143.4 (C-5), 156.0 (C-4").

HRMS, m/z=21.0794 found (calculated for $C_{10}H_{13}N_3ONa$ $[M+Na]^+$ requires 212.0793).

Example 29

TABLE 3

Other N-phenylalkyl azole SOCE inhibitors with free hydroxyl function or protected hydroxyl function on the terminal side chain.

| Compound Number | | Isolated yield (%) | Mp (° C.) or physical state | Method of preparation | Starting compounds |
|---|---|---|---|---|---|
| 9αe | 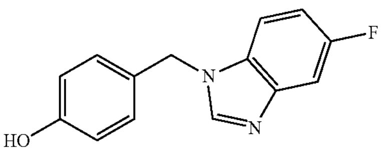 [SMILES: Oc1ccc(Cn2cnc3cc(F)ccc32)cc1] | 25 | 227-229 | Example 19 | 8αe |
| 8βc | 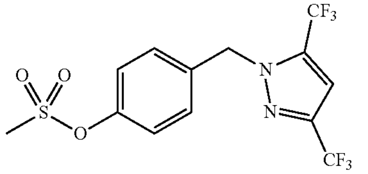 [SMILES: CS(=O)(=O)Oc1ccc(Cn2nc(C(F)(F)F)cc2C(F)(F)F)cc1] | 71 | 84-88 | Example 1 | 7, 4b |

II. Biological Properties of the SOCE Inhibitors

Example 30

All the "final" molecules and some of the synthetic intermediates that are described in section I above have been subjected to biological activity tests at the CalciScreen platform at the University of Brest for their potential SOCE regulation activity on different cell lines.

The effects of the molecules developed were tested on PLP-B lymphocytes. Store-operated $Ca^{2+}$ entry was induced by depletion of Endoplasmic Reticulum $Ca^{2+}$ stores (ER $Ca^{2+}$ stores) with thapsigargin (Tg) in a $Ca^{2+}$-free medium and measured following the addition of 1.8 mM of $CaCl_2$) in the extracellular medium. The results are compared to the results obtained for known SOCE inhibitors SKF-96365, GSK-7975A, Synta 66.

Then, effects of the molecule that gave the best results in this test (i.e., molecule 6αa) were assessed in two cancer cell lines, namely: HEK 293 and HEK 651 HS1 tumor cell lines.

Table 4 presents the results obtained for 1-[4-(phenylalkoxy)phenylethyl]-1H-benzo[d]imidazole 6α and susbstituted 1-[4-(phenylalkoxy)phenylethyl]-1H-indazole 6αf, 6α(x,y) in PLP-B lymphocytes; Table 5 presents the results obtained for 1-[4-(phenylalkoxy)phenylethyl]-1H-pyrazole 6βc and susbstituted 1-[4-(phenylalkoxy) phenylethyl]-1H-1,2,4-triazole 6β(j-l) in PLP-B lymphocytes; and Table 6 presents the results obtained for 1-(4-hydroxyphenylalkyl)-1H-azole 9α, 9β, 12α, 12β and their precursors 8α, 8β, 11α, 11β in PLP-B lymphocytes. Table 7 presents the results obtained for compound 6αa in cancer cell lines.

TABLE 4

Effects of 1-[4-(phenylalkoxy)phenylethyl]-1H-benzo[d]imidazole 6α and susbstituted 1-[4-(phenylalkoxy)phenylethyl]-1H-indazole 6αf, 6α(x, y) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM)[b] |
|---|---|---|---|---|
| 6αc | 100 | −26.0# | −18.0 | |
| DAD 4-546 | 50 | −30.0# | −18.0 | |
| | 10 | | | |
| | 1 | | | |
| | 0.1 | | | |
| 6αt | 100 | −34.0# | −22.0# | |
| VAL 1-76 | 50 | −10.0// | 6 | |
| | 10 | −3.0 | 1.0 | |
| | 1 | | | |
| | 0.1 | | | |
| 6αm | 100 | −55.0* | −11.0// | |
| VAL 1-77 | 50 | −12.0// | −1.0 | |
| | 10 | 4.0 | −1.0 | |
| | 1 | | | |
| | 0.1 | | | |
| 6αu | 100 | −68.0* | 5.0 | |
| VAL 1-75 | 50 | −30.0# | 11.0 | |
| | 10 | 6.0 | 5.0 | |
| | 1 | | | |
| | 0.1 | | | |
| 6αv | 100 | −77.0* | 2.0 | |
| VAL 1-64 | 50 | −25.0# | 11.0// | |
| | 10 | 8.0 | 0.0 | |
| | 1 | | | |
| | 0.1 | | | |
| 6αe | 100 | −9.0 | 1.0 | |
| DAD 4-548 | 50 | −28.0# | 5.0 | |
| | 10 | | | |
| | 1 | | | |
| | 0.1 | | | |
| 6αd | 100 | −72.0* | −3.0 | |
| DAD 4-547 | 50 | −26.0# | −5.0 | |
| | 10 | | | |

TABLE 4-continued

Effects of 1-[4-(phenylalkoxy)phenylethyl]-1H-benzo[d]imidazole 6α and susbstituted 1-[4-(phenylalkoxy)phenylethyl]-1H-indazole 6αf, 6α(x, y) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM)[b] |
|---|---|---|---|---|
| | 1 | | | |
| | 0.1 | | | |
| 6αo | 100 | −82.0* | 8.0 | |
| DAD 4-551 | 50 | −33.0# | −4.0 | |
| | 10 | | | |
| | 1 | | | |
| | 0.1 | | | |
| 6αp | 100 | −71.0* | −7.0 | |
| DAD 4-552 | 50 | −29.0# | −15.0// | |
| | 10 | | | |
| | 1 | | | |
| | 0.1 | | | |
| 6αab | 100 | −46.0# | −8.0 | |
| DAD 4-553 | 50 | −2.0 | −1.0 | |
| | 10 | | | |
| | 1 | | | |
| | 0.1 | | | |
| 6αac | 100 | −84.3* | 13.2// | 13.5 |
| DAD 4-566 | 50 | −87.2* | 9.0 | |
| | 10 | −31.1# | 9.6 | |
| | 1 | 6.2 | −1.1 | |
| | 0.1 | 12.9 | 2.3 | |
| 6αad | 100 | −84.3* | | |
| DAD 4-567 | 50 | −81.7* | −9.1 | |
| | 10 | −28.1# | −5.7 | |
| | 1 | 2.9 | −16.2// | |
| | 0.1 | 12.9 | | |
| 6αd | 100 | −64.0* | −15.1// | |
| DAD 4-568 | 50 | 1.3 | −5.3 | |
| | 10 | −7.8 | −8.5 | |
| | 1 | | | |
| | 0.1 | | | |
| 6αs | 100 | −56.9* | −4.1 | |
| DAD 4-570 | 50 | −19.0// | 0.7 | |
| | 10 | −9.4 | −10.6// | |
| | 1 | | | |
| | 0.1 | | | |
| 6αae | 100 | −12.4* | −12.0// | |
| DAD 4-569 | 50 | 13.1* | −7.6 | |
| | 10 | 7.5 | −11.3// | |
| | 1 | | | |
| | 0.1 | | | |
| 6αa | 100 | −81.0* | −2.0 | 15.4 |
| DAD 3-473 | 50 | −79.0* | −5.0 | |
| | 10 | −24.0 | −5.0 | |
| | 1 | 2 | 7.0 | |
| | 0.1 | −3.0 | 5.0 | |
| 6αm | 100 | −77.0* | 7.0 | |
| DAD 3-475 | 50 | −4.0 | 7.0 | |
| | 10 | | | |
| | 1 | | | |
| | 0.1 | | | |
| 6αn | 100 | −25.0 | −3.0 | |
| DAD 3-474 | 50 | 4.0 | 5.0 | |
| | 10 | 16.0 | −5.0 | |
| | 1 | 1.0 | −11.0// | |
| | 0.1 | | | |
| 6αz | 100 | 5.9 | −1.5 | |
| DAD 4-472 | 50 | −13.7* | −1.9 | |
| | 10 | −15.4* | −1.6 | |
| | 1 | | | |
| | 0.1 | | | |

TABLE 4-continued

Effects of 1-[4-(phenylalkoxy)phenylethyl]-1H-benzo[d]imidazole 6α and susbstituted 1-[4-(phenylalkoxy)phenylethyl]-1H-indazole 6αf, 6α(x, y) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM)[b] |
|---|---|---|---|---|
| 6αb | 100 | −30.0# | −22.0# | |
| DAD 4-573 | 50 | 0.0 | −5.0 | |
| | 10 | 14# | −8.0 | |
| | 1 | | | |
| | 0.1 | | | |
| 6αaa | 100 | −31.6# | −19.7// | |
| DAD 4-574 | 50 | −16.4// | −13.3// | |
| | 10 | −10.4// | −23.1# | |
| | 1 | | | |
| | 0.1 | | | |
| 6αab | 100 | −43.6# | −24.2# | |
| DAD 4-575 | 50 | −2.9 | −20.7# | |
| | 10 | 20.8# | −8.9 | |
| | 1 | | | |
| | 0.1 | | | |
| 6αad | 100 | 5.0 | −15.0// | |
| VAL3.31 | 50 | 54.0* | −9.0 | |
| | 10 | 51.0* | −10.0// | |
| | 1 | | | |
| | 0.1 | | | |
| 6αae | 100 | −24.0# | −27.0# | |
| VAL3.32 | 50 | 23.0# | −19.0// | |
| | 10 | 39.0# | −26.0# | |
| | 1 | | | |
| | 0.1 | | | |
| 6αaf | 100 | −2.0 | −38.0# | |
| VAL3.33 | 50 | 1.0 | −34.0# | |
| | 10 | 40.0# | −29.0# | |
| | 1 | | | |
| | 0.1 | | | |
| GSK-7975A | 100 | −94.0 | | 2.3 |
| | 50 | −88.0 | | |
| | 10 | −9.0 | | |
| | 1 | 19.0 | | |
| | 0.1 | | | |
| Synta 66 | 100 | −89.0 | | 8.8 |
| | 50 | −74.0 | | |
| | 10 | 6.0 | | |
| | 1 | 9.0 | | |
| | 0.1 | | | |
| SKF-96365 | 100 | −58.7* | −8.0 | 60 |
| | 50 | −44.3# | −11.1// | |
| | 10 | −15.4// | −6.6 | |
| | 1 | −26.4# | 6.5 | |
| | 0.1 | −3.4 | 2.4 | |

[a] % of inhibition (—) or activation.

Controlled with DMSO 100%.

[b]$IC_{50}$ expressed in μM are the average of three assays, ±0.5 μM.

TABLE 5

Effects of 1-[4-(phenylalkoxy)phenylethyl]-1H-pyrazole 6βc and substituted 1-[4-(phenylalkoxy)phenylethyl]-1H-1,2,4-triazole 6β(j-l) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM) [b] |
|---|---|---|---|---|
| 6βu | 100 | 0.4 | | |
| | 50 | 0.2 | | |
| | 10 | −2.0 | | |
| | 1 | | | |
| | 0.1 | | | |
| 6βq | 100 | −37.0 | | |
| | 50 | −5.0 | | |
| | 10 | | | |
| | 1 | | | |
| | 0.1 | | | |
| 6βm | 100 | 16.8 | | |
| | 50 | 0.5 | | |
| | 10 | 2.0 | | |
| | 1 | | | |
| | 0.1 | | | |
| 6βg | 100 | −37.0* | −25.0* | |
| | 50 | −5.0 | −18.0// | |
| | 10 | | | |
| | 1 | | | |
| | 0.1 | | | |
| 6βd | 100 | 5.0 | −1.0 | |
| | 50 | 1.0 | −10.0// | |
| | 10 | | | |
| | 1 | | | |
| | 0.1 | | | |
| 6βv | 100 | −30.0* | | |
| | 50 | −29.0* | | |
| | 10 | | | |
| | 1 | | | |
| | 0.1 | | | |
| 6βr | 100 | −32.7 | | |
| | 50 | −6.6 | | |
| | 10 | | | |
| | 1 | | | |
| | 0.1 | | | |
| 6βn | 100 | −62.0 | | |
| | 50 | −7.2 | | |
| | 10 | 6.5 | | |
| | 1 | | | |
| | 0.1 | | | |
| 6βr | 100 | −63.0* | −23.0# | |
| | 50 | −24.0* | −23.0# | |
| | 10 | | | |
| | 1 | | | |
| | 0.1 | | | |
| 6βd | 100 | −13.0 | −29.0 | |
| | 50 | 7.0 | −14.0// | |
| | 10 | | | |
| | 1 | | | |
| | 0.1 | | | |
| 6βw | 100 | −11.8 | | |
| | 50 | 0.1 | | |
| | 10 | −4.6 | | |
| | 1 | | | |
| | 0.1 | | | |
| 6βs | 100 | −64.0* | | |
| | 50 | −34.0# | | |
| | 10 | −13.0// | | |
| | 1 | | | |
| | 0.1 | | | |
| 6βp | 100 | 0.5 | | |
| | 50 | −1.0 | | |
| | 10 | 1.3 | | |
| | 1 | | | |
| | 0.1 | | | |

TABLE 5-continued

Effects of 1-[4-(phenylalkoxy)phenylethyl]-1H-pyrazole 6βc and substituted 1-[4-(phenylalkoxy)phenylethyl]-1H-1,2,4-triazole 6β(j-l) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM) [b] |
|---|---|---|---|---|
| 6βs | 100 | −51.0* | −10.0// | |
| | 50 | −25.0* | −6.0 | |
| | 10 | | | |
| | 1 | | | |
| | 0.1 | | | |
| 6βe | 100 | −21.0# | −31.0# | |
| | 50 | −6.0 | −31.0# | |
| | 10 | | | |
| | 1 | | | |
| | 0.1 | | | |
| 6βf | 100 | −10.0 | | |
| | 50 | 2.0 | | |
| | 10 | 7.0 | | |
| | 1 | | | |
| | 0.1 | | | |
| 6βt | 100 | −19.1 | | |
| | 50 | −7.7 | | |
| | 10 | | | |
| | 1 | | | |
| | 0.1 | | | |
| 6βp | 100 | −81.0 | | 25 |
| | 50 | −21.0 | | |
| | 10 | 14.0 | | |
| | 1 | 16.0 | | |
| | 0.1 | | | |
| 6βi | 100 | −43.0* | −7.0 | |
| | 50 | −13.0// | −6.0 | |
| | 10 | | | |
| | 1 | | | |
| | 0.1 | | | |
| 6βf | 100 | | | |
| | 50 | −12.0// | −18.0// | |
| | 10 | −7.0 | −13.00// | |
| | 1 | | | |
| | 0.1 | | | |
| 6βy | 100 | −64.0* | −30.0* | |
| | 50 | −34.0# | −23.0* | |
| | 10 | −13.0# | −17.0 | |
| | 1 | | | |
| | 0.1 | | | |
| 6βz | 100 | −40.0# | −8.0 | |
| | 50 | −37.0# | −12.0// | |
| | 10 | −30.0# | −9.0 | |
| | 1 | | | |
| | 0.1 | | | |
| 6βaa | 100 | −29.0# | −11.0 | |
| | 50 | −20.0# | −4.0 | |
| | 10 | −18.0// | −8.0 | |
| | 1 | | | |
| | 0.1 | | | |
| GSK-7975A | 100 | −94.0* | | 2.3 |
| | 50 | −88.0* | | |
| | 10 | −9.0 | | |
| | 1 | 9.0 | | |
| | 0.1 | | | |
| Synta 66 | 100 | −89.0* | | 8.8 |
| | 50 | −74.0* | | |
| | 10 | 6.0 | | |
| | 1 | 9.0 | | |
| | 0.1 | | | |

TABLE 5-continued

Effects of 1-[4-(phenylalkoxy)phenylethyl]-1H-pyrazole 6βc and substituted 1-[4-(phenylalkoxy)phenylethyl]-1H-1,2,4-triazole 6β(j-l) on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect on amplitude of SOCE Peak [a] | Effect on amplitude of Tg Peak [a] | $IC_{50}$ (μM) [b] |
|---|---|---|---|---|
| SKF-96365 | 100 | −58.7* | −8.0 | 60 |
| | 50 | −44.3# | −11.1// | |
| | 10 | −15.4// | −6.6 | |
| | 1 | −26.4# | 6.5 | |
| | 0.1 | −3.4 | 2.4 | |

[a] % of inhibition (—) or activation.

Controlled with DMSO 100%.

[b] $IC_{50}$ expressed in μM are the average of three assays, ±0.5 μM.

TABLE 6

Effects of 1-(4-hydroxyphenylalkyl)-1H-azole 9α, 9β, 12α, 12β and their precursors 8α, 8β, 11α, 11β on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect of on amplitude of SOCE Peak [a] | Effect on amplitude of Tg Peak [a] | $IC_{50}$ (μM) [b] |
|---|---|---|---|---|
| 9αd | 100 | −7.0 | 4.0 | |
| | 50 | 9.0 | 13.0// | |
| | 10 | 5.0 | 15.0// | |
| | 1 | | | |
| | 0.1 | | | |
| 9αa | 100 | 3.0 | −12.0// | |
| | 50 | −4.0 | −1.0 | |
| | 10 | 2.0 | 13.0// | |
| | 1 | | | |
| | 0.1 | | | |
| 9αe | 100 | −21.0# | −15.0// | |
| | 50 | −5.0 | −8.0 | |
| | 10 | 6.0 | −3.0 | |
| | 1 | | | |
| | 0.1 | | | |
| 9αc | 100 | −33.0# | 6.0 | |
| | 50 | −16.0// | 1.0 | |
| | 10 | −23.0# | −6.0 | |
| | 1 | | | |
| | 0.1 | | | |
| 9βb | 100 | −12.0// | −8.0 | |
| | 50 | −10.0// | −14.0// | |
| | 10 | −8.0 | −8.0 | |
| | 1 | | | |
| | 0.1 | | | |
| 12αa | 100 | 2.5 | 7.4 | |
| | 50 | −0.9 | 4.3 | |
| | 10 | 2.2 | 2.7 | |
| | 1 | | | |
| | 0.1 | | | |
| 12αa_bis | 100 | 37.8# | −7.9 | |
| | 50 | 60.5* | −7.3 | |
| | 10 | 44.5# | −13.0// | |
| | 1 | | | |
| | 0.1 | | | |

TABLE 6-continued

Effects of 1-(4-hydroxyphenylalkyl)-1H-azole 9α, 9β, 12α, 12β and their precursors 8α, 8β, 11α, 11β on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect of on amplitude of SOCE Peak [a] | Effect on amplitude of Tg Peak [a] | $IC_{50}$ (μM) [b] |
|---|---|---|---|---|
| 12αd | 100 | −6.4 | 4.6 | |
| | 50 | 3.0 | 4.2 | |
| | 10 | 2.7 | 6.0 | |
| | 1 | | | |
| | 0.1 | | | |
| 12αe | 100 | −8.0 | −28.0# | |
| | 50 | −18.0// | −29.0# | |
| | 10 | −5.0 | −11.0* | |
| | 1 | | | |
| | 0.1 | | | |
| 11βa | 100 | −16.0// | −3.0 | |
| | 50 | −31.0# | −17.0// | |
| | 10 | −32.0# | −20.0# | |
| | 1 | | | |
| | 0.1 | | | |
| 12βa | 100 | −12.0// | −8.0 | |
| | 50 | −10.0// | −14.0// | |
| | 10 | −8.0 | −8.0 | |
| | 1 | | | |
| | 0.1 | | | |
| 12αb | 100 | −3.0 | 0.0 | |
| | 50 | 1.0 | 4.0 | |
| | 10 | 25.0# | 7.0 | |
| | 1 | | | |
| | 0.1 | | | |
| 12αc | 100 | 1 | 5.0 | |
| | 50 | 3 | 2.0 | |
| | 10 | 20# | 11.0// | |
| | 1 | | | |
| | 0.1 | | | |
| 11αe | 100 | −88.0* | −20.0# | 40.0 |
| | 50 | −54.0* | −9.0 | |
| | 10 | −33.0# | −8.0 | |
| | 1 | −20.0# | | |
| | 0.1 | −23.0# | | |
| 8αa | 100 | −23.0# | −7.0 | |
| | 50 | −9.0 | 5.0 | |
| | 10 | −20.0# | 1.0 | |
| | 1 | | | |
| | 0.1 | | | |
| 8αc | 100 | −24.0# | −32.0# | |
| | 50 | −9.0 | 10.0* | |
| | 10 | −14.0// | 10.0* | |
| | 1 | | | |
| | 0.1 | | | |
| 8βb | 100 | −35.0# | −6.0 | |
| | 50 | −41.0# | 2.0 | |
| | 10 | −27.0# | −3.0 | |
| | 1 | −23.0# | −9.0 | |
| | 0.1 | −19.0// | −23.0// | |
| 8βc | 100 | −31.0# | −21.0# | |
| | 50 | −22.0# | −2.0 | |
| | 10 | −12.0// | 4 | |
| | 1 | | | |
| | 0.1 | | | |
| 8βa | 100 | −25.0# | −12.0// | |
| | 50 | −27.0# | −14.0// | |
| | 10 | −30.0# | −20.0# | |
| | 1 | | | |
| | 0.1 | | | |
| 11αb | 50 | −51.0* | −2.0 | 6.8 |
| | 10 | −29.0# | 2.0 | |
| | 5 | 16.0// | −2.0 | |
| | 1 | 41.0# | 0.0 | |
| | 0.1 | 28.0# | 11.0// | |

TABLE 6-continued

Effects of 1-(4-hydroxyphenylalkyl)-1H-azole 9α, 9β, 12α, 12β and their precursors 8α, 8β, 11α, 11β on store-operated $Ca^{2+}$ entry in PLP-B lymphocytes, compared to known standard SOCE inhibitor (SKF-96365, GSK-7975A, Synta 66). In the following table, "white" represents "No effect", i.e., a value between 0 and 10%; "//" represents a "Moderate effect", i.e., value between 10% and 20%; "#" represents a "Significant effect", i.e., a value between 20% and 50%; and "*" represents a "Very significant effect", i.e., a value between >50%.

| Compound | Concentration (μM) | Effect of on amplitude of SOCE Peak [a] | Effect on amplitude of Tg Peak [a] | $IC_{50}$ (μM) [b] |
|---|---|---|---|---|
| 11αc | 100 | −35.0# | 3.0 | 1.6 |
| | 50 | −54.0* | −12.0 | |
| | 10 | −31.0# | −10.0 | |
| | 1 | 26.0# | 4.0 | |
| | 0.1 | 67.0* | 16.0// | |
| GSK-7975A | 100 | −94.0 | | 2.3 |
| | 50 | −88.0 | | |
| | 10 | −9.0 | | |
| | 1 | 9.0 | | |
| | 0.1 | | | |
| Synta 66 | 100 | −89.0 | | 8.8 |
| | 50 | −74.0 | | |
| | 10 | 6.0 | | |
| | 1 | 9.0 | | |
| | 0.1 | | | |
| SKF-96365 | 100 | −58.7* | −8.0 | 60 |
| | 50 | −44.3# | −11.1// | |
| | 10 | −15.4// | −6.6 | |
| | 1 | −26.4# | 6.5 | |
| | 0.1 | −3.4 | 2.4 | |

[a] % of inhibition (—) or activation.
Controlled with DMSO 100%.
[b] $IC_{50}$ expressed in μM are the average of three assays, ±0.5 μM.

TABLE 7

Effects of compound 6αa on store-operated $Ca^{2+}$ entry in HEK 293 and HEK 651 HS1 tumor cell lines, compared to known standard SOCE inhibitor (SKF-96365, and GSK-7975A). In the following table, "white" represents "No effect", i.e., a value between 0 and 10%; "light gray" represents a "Moderate effect", i.e., value between 10% and 20%; "medium gray" represents a "Significant effect", i.e., a value between 20% and 50%; and "dark gray" represents a "Very significant effect", i.e., a value between >50%.

| | | HEK 293 | | HEK 651 HS1 | |
|---|---|---|---|---|---|
| Compound | Concen-tration (μM) | Effect on amplitude of SOCE peak[a] | $IC_{50}$ (μM)[b] | Effect on amplitude of SOCE peak | $IC_{50}$ (μM)[b] |
| 6αa DAD 3-473 | 50 | −91 | 5.1 | −86 | 25 |
| | 10 | −73 | | −35 | |
| | 5 | −15 | | −5 | |
| | 1 | 8 | | | |
| | 0.1 | | | | |
| GSK-7975A | 50 | −87 | 2.0 | −72 | 44 |
| | 10 | −75 | | −22 | |
| | 5 | −66 | | −19 | |
| | 1 | −31 | | −2 | |
| | 0.1 | −7 | | 0 | |

TABLE 7-continued

Effects of compound 6αa on store-operated $Ca^{2+}$ entry in HEK 293 and HEK 651 HS1 tumor cell lines, compared to known standard SOCE inhibitor (SKF-96365, and GSK-7975A). In the following table, "white" represents "No effect", i.e., a value between 0 and 10%; "light gray" represents a "Moderate effect", i.e., value between 10% and 20%; "medium gray" represents a "Significant effect", i.e., a value between 20% and 50%; and "dark gray" represents a "Very significant effect", i.e., a value between >50%.

| | | HEK 293 | | HEK 651 HS1 | |
|---|---|---|---|---|---|
| Compound | Concentration (μM) | Effect on amplitude of SOCE peak[a] | $IC_{50}$ (μM)[b] | Effect on amplitude of SOCE peak | $IC_{50}$ (μM)[b] |
| SKF-96365 | 50 | −33 | ND[c] | −63 | 40 |
| | 10 | −4 | | −17 | |
| | 5 | −23 | | −9 | |
| | 1 | −21 | | −6 | |
| | 0.1 | −25 | | −8 | |

[a]% of inhibition (—) or activation.
Controlled with DMSO 100%.
[b]$IC_{50}$ expressed in μM are the average of three assays, ±0.5 μM.
[c]ND: Not determined.

Conclusion

The objective was to identify innovative modulators of SOCE that inhibit SOCE without inhibiting the release of $Ca^{2+}$ from endoplasmic reticulum $Ca^{2+}$ stores. The other objective was to select inhibitors with a better inhibition on SOCE than SKF-96365. The molecules from the 6α series were found to be the most effective and the 6αa molecule was found to be the best candidate in the 6α series (Table 6). In conclusion, the compound 6αa is a new inhibitor of SOCE with an efficiency superior or equal to that of previously described SOCE inhibitors such as GSK-7975A (Table 7).

III. SOCE Inhibition by Inventive Compound 6αa and Comparison with GSK-7975A and SKF-93365

Example 31

A. Materials and Methods

Methods for Measurement of Intracellular Calcium Levels

Intracellular calcium levels were monitored at 37° C. using the FlexStation 3™ (Molecular Devices, Berkshire, UK), a fluorescence plate reader measuring time-resolved intracellular $Ca^{2+}$ concentration in a 96-well format with cells loaded with the dual-wavelength fluorescent calcium-sensitive dye Fura-2AM.

Intracellular $Ca^{2+}$ stores were depleted with 2 μM Thapsigargin (an inhibitor of ER SERCA pumps) under $Ca^{2+}$-free conditions to determine the magnitude of intracellular $Ca^{2+}$ release. Next, the cells were returned to $Ca^{2+}$-containing Hepes-buffered solution to measure SOCE. The magnitude of SOCE was estimated as the maximal values of normalized fluorescence ratio following $Ca^{2+}$ re-addition.

The data were stored for later analysis by using Softmax-Pro (Molecular Devices), Excel and Graph Pad Prism software (Graph Pad Software, La Jolla, CA, USA).

Methods for Functional Assays on B Cells (JOK Cells).

Cell Viability Assays. JOK cells were treated with test compounds (GSK-7975-A, SKF-93365 and 6αa) or solvent for 48 hours. JOK cells viability was then assessed using LIVE/DEAD cell viability assays kit (Abcam). Differentially labeled live and dead cells with fluorescent dyes are analyzed by flow cytometry.

Cell Proliferation Assays. Cultured JOK cells were seeded in 96-well culture plates with or without inhibitors. After 48 hours, cell proliferation was assessed using WST-8 assay (Sigma Aldrich). The absorbance was read at 450 nm on a plate reader.

Cell Cycle Analysis. JOK cells were incubated with or without test compounds (GSK-7975-A, SKF-93365 and 6αa) for 48 hours and then washed with cold PBS and fixed with 70% ethanol for 30 minutes at room temperature. Cell cycle was analyzed using propidium iodide (PI). Cell-cycle distribution was determined by PI-staining using flow cytometry and analyzed by Kaluza 1.3.

Apoptosis Assay. Apoptosis of JOK cells were determined by Annexin V-FITC/PI staining (Biolegend) using flow cytometry. The percentage of annexin V-FITC and propidium iodide-negative cells were assessed using Kaluza 1.3.

Migration Protocol. Migration chambers (transwells) (Transwell 5.0 m polycarbonate membrane Costar) were coated overnight (37° C., 5% $CO_2$) with 100 μL of fibronectine solution containing BSA (1 mg/ml) and LHC Basal Medium. Primary HUmbilical Vein Endothelial Cells (HUVEC) were seeded in each transwell (100 000/well) and cultured for 24 hours (37° C., 5% $CO_2$). To evaluate B cell migration, JOK cells were added (300 000/well) to each transwell upper chamber containing RPMI 1640 medium (BioWest) containing 0.5% BSA and SDF1 (200 ng/ml) was added in the bottom chamber. Cells were cultures in the presence or absence of a test compound (GSK-7975-A, SKF-93365 and 6αa) or solvent. After 24 hours (37° C., 5% $CO_2$), migrated cells were collected in the bottom chambers and counted by flow cytometry. The percentages of migration were calculated for each experimental collection.

Methods for Functional Assays on Pancreatic Cancer Cells (PANC-1 Cells).

Analysis of Cell Proliferation. For PANC-1 cell proliferation and cell cytotoxicity measurements, $10^6$ cells were seeded in 96 well-plates in 100 μL of DMEM medium. Cells were incubated for 24 hours at 37° C. with 3 different SOCE inhibitors (GSK-7975-A, SKF-93365 and 6αa) at 2 different concentrations (5 and 20 μM) compared to DMSO and untreated cells. Cell proliferation was evaluated using the Cell Titer kit proliferation assay (Promega). Cytotoxicity was evaluated using the Cell Tox green cytotoxicity assay (Promega). All the kits were used following manufacturer recommendations and using a plate reader.

Analysis of Cell Apoptosis. For PANC-1 cell apoptosis measurements, $5\times10^6$ cells were seeded in 12 well-plates. Cells were incubated for 24 hours with a test compound (GSK-7975-A, SKF-93365 and 6αa) at two different concentrations (5 and 20 μM) compared to DMSO and untreated cells at 37° C. After washing, cells were taken off plates using an enzyme-free solution. Cells were centrifuged for 5 minutes at 1500 rpm and suspended in 50 mL of PBS containing 1 μL of AnnexinV-FiTC and 1 μL of propidium iodide (PI) for 15 minutes at room temperature in the dark. Evaluation of Annexin and PI staining was performed using a flow cytometer (Navios, Beckman Counter) to evaluate cell apoptosis and necrosis.

B. Results.

Figure 3:
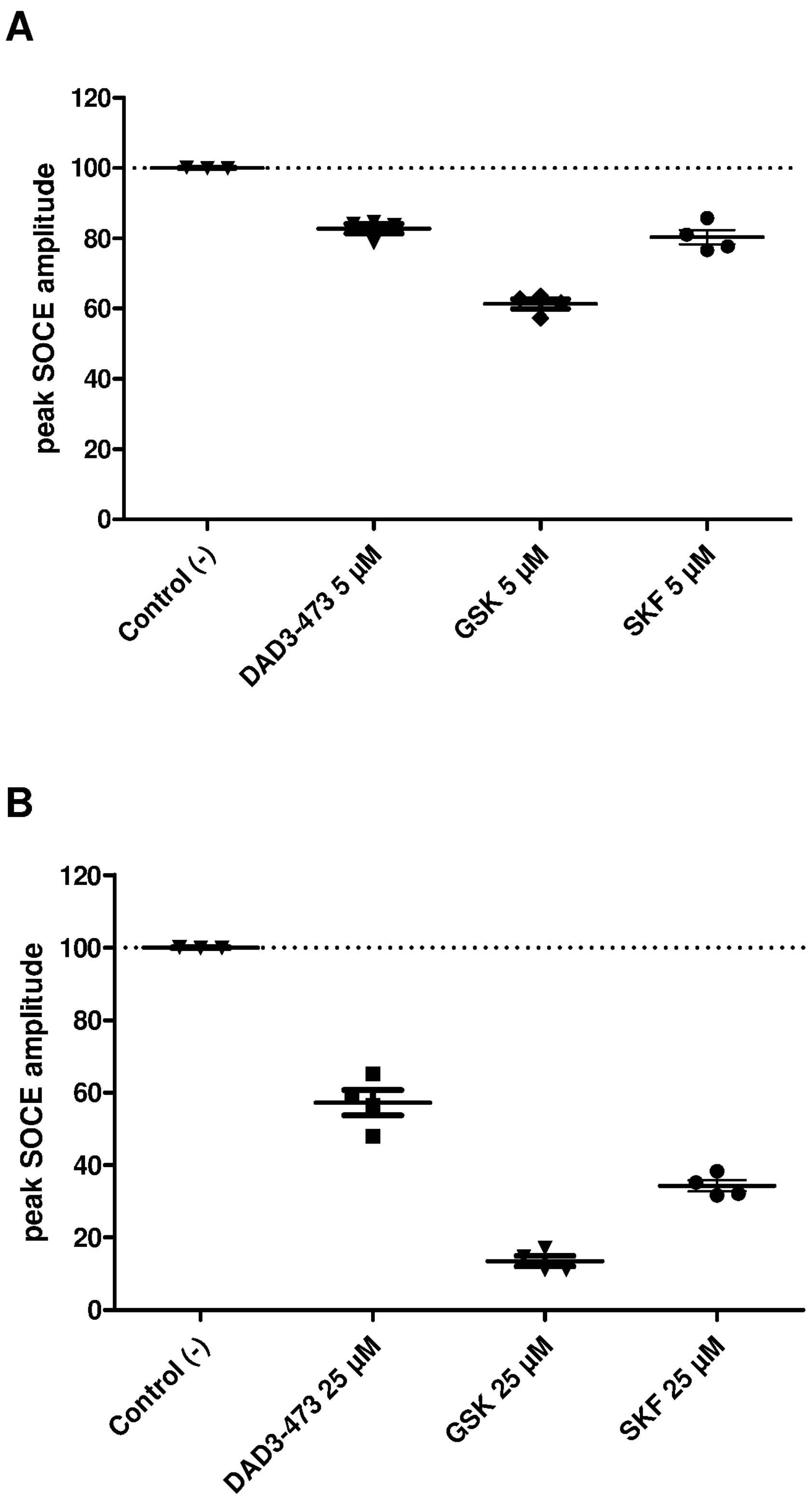
FIG. 3. SOCE Inhibition by 6αa, GSK-7975-A and SKF-93365 in a B Cell Line. SOCE inhibition of JOK B cells after ER $Ca^{2+}$ store depletion using thapsigargin, when the inventive compound 6αa (DAD 3-473), the SOCE inhibitor GSK-7975A, and the SOCE inhibitor SKF-93365 were added at the time of $Ca^{2+}$ re-addition. Each compound was added at a final concentration of 5 μM (A) or at a final concentration of 25 μM (B).
Figure 6:
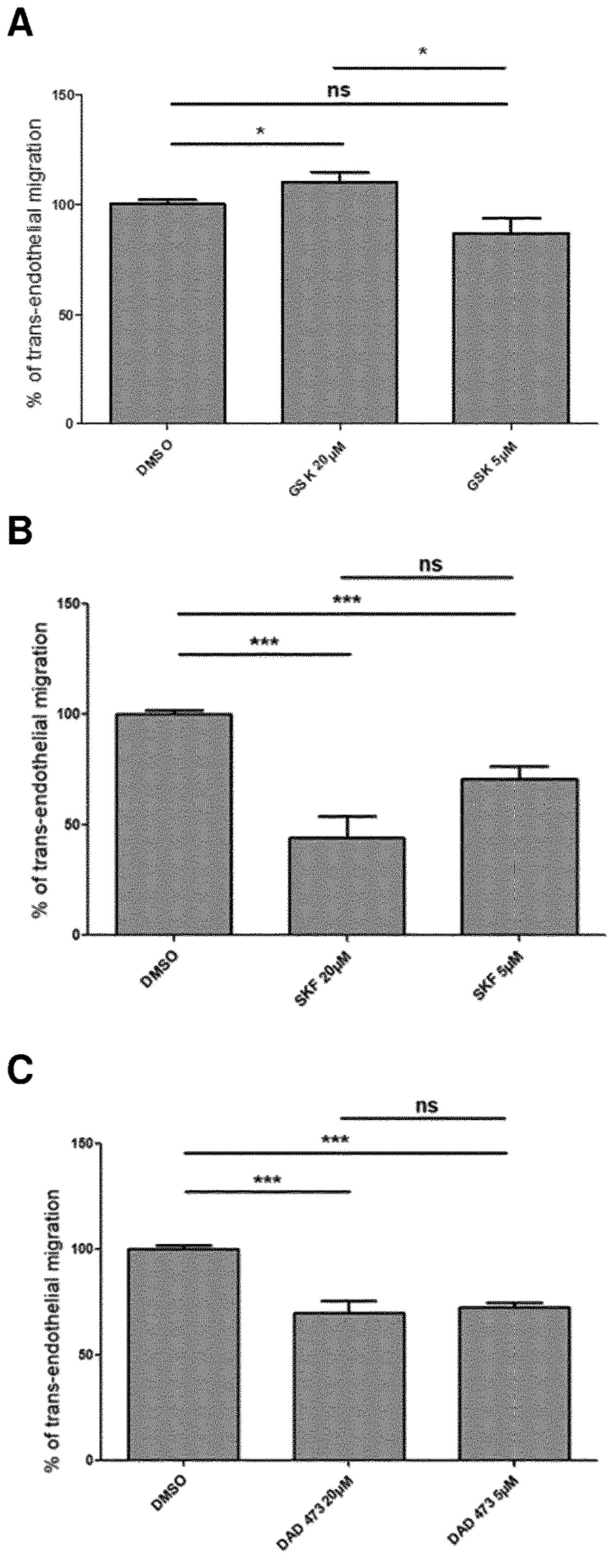
FIG. 6. In vitro Effects of 6αa, GSK-7975-A and SKF-93365 on B Cell Trans-Epithelial Migration. In each experimental approach, JOK cells were treated for 24 hours with 2 different concentrations (5 μM and 20 μM) of the SOCE inhibitor GSK-7975A (A), the SOCE SKF-93365 (B) and the inventive compound 6αa (DAD 3-473) (C). The effects of the different inhibitors on trans-epithelial migration were evaluated after 24 hours. Histograms represent for each experimental condition individual values and the mean±SEM of n observations. Data were normalized to the mean values obtained for cells treated with the DMSO control. Data are analyzed by non parametric Mann Withney analysis, *P<0.05, P<0.01 and *P<0.001.

Effects of Drug Treatment on JOK B Cells Intracellular Calcium Levels. The results are presented on FIGS. 3 and 4. FIG. 3 and FIG. 4 show that compound 6αa, as observed in the case of GSK-7975A and SKF-93365 at two different concentrations (5 and 20 µM), significantly reduces the amplitude of SOCE compared to control irrespective of the incubation time with the drugs (FIG. 3: 1 hour incubation; FIG. 4A: 5 minute incubation; FIG. 4B: 15 minute incubation; FIG. 4C: 30 minute incubation). The amplitude of $Ca^{2+}$ release from the endoplasmic stores was not found to be significantly affected by in the presence of 6αa, GSK-7975A and SKF-93365.

Figure 7:
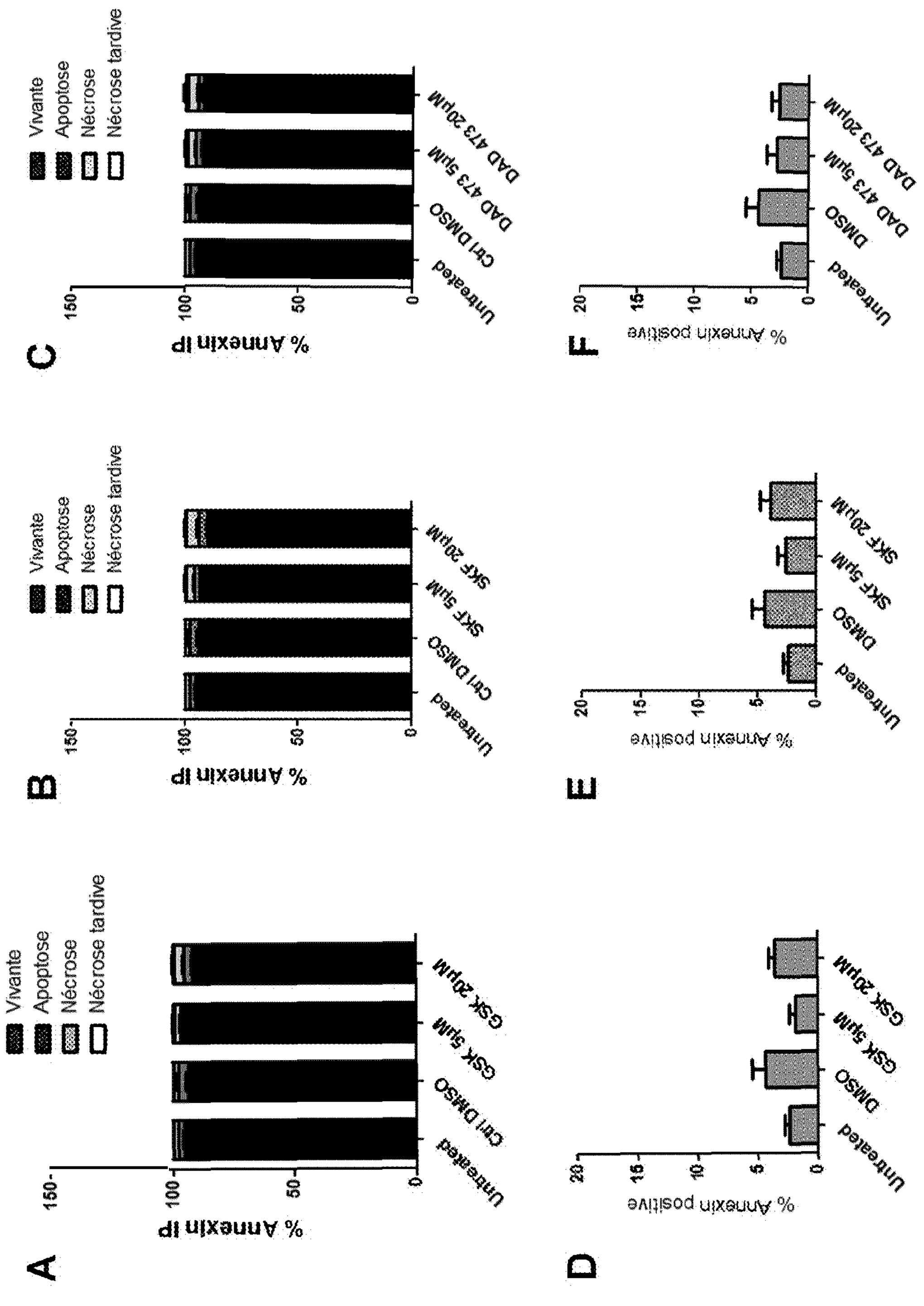
FIG. 7. In vitro Effects of 6αa, GSK-7975-A and SKF-93365 on B Cell Death. JOK cells were treated for 24 hours with 2 different concentrations of the three SOCE inhibitors (5 μM and 20 μM) or with control DMSO. Percentages of living cells, necrotic cells or apoptotic cells submitted to GSK-7975A (A), SKF-93365 (B), and 6αa (DAD 3-473) (C) treatment were normalized to the DMSO treatment conditions. Histograms present the amounts of apoptotic cells (annexin/PI positive cells) detected in each experimental condition after treatment with GSK-7975A (D), SKF-93365 (E), and 6αa (DAD 3-473) (F). Data are expressed as mean±SEM of n observations (n=2). Data are analyzed with non parametric Mann Withney analysis, *P<0.05, P<0.01 and *P<0.001.
Figure 8:
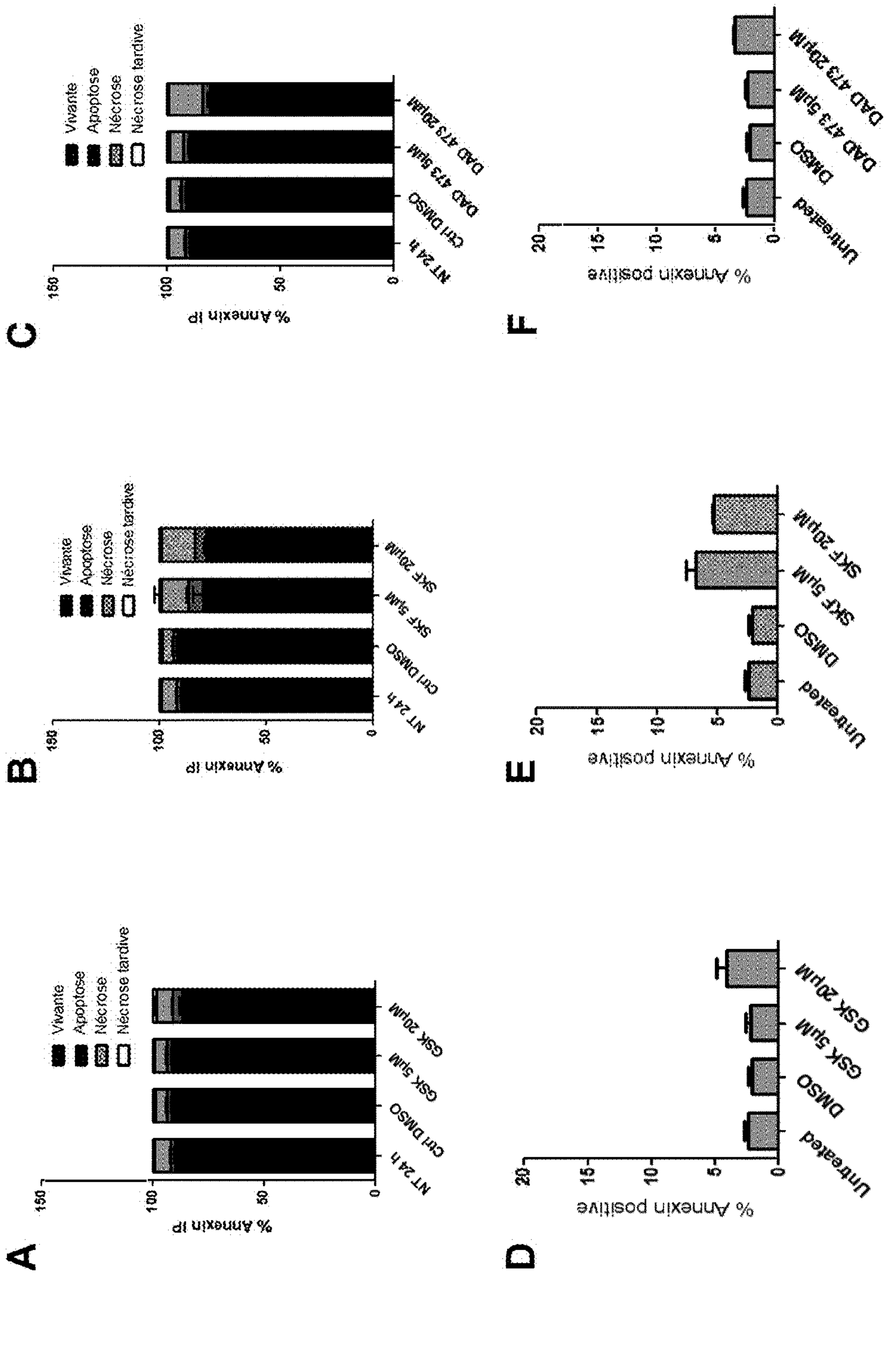
FIG. 8. In vitro Effects of 6αa, GSK-7975-A and SKF-93365 on HUVEC Cell Death. HUVEC cells were treated for 24 hours with 2 different concentrations (5 μM and 20 μM) of the three SOCE inhibitors (5 μM and 20 μM) or with control DMSO. Cell death was analyzed by flow cytometry following Annexin/Propidium Iodide labeling. Percentages of living cells, necrotic cells and apoptotic cells submitted to GSK-7975A (A), SKF-93365 (B), and 6αa (DAD 3-473) (C) treatment were normalized to the DMSO treatment conditions. Histograms present the amounts of apoptotic cells (annexin/PI positive cells) detected in each experimental condition after treatment with GSK-7975A (D), SKF-93365 (E), and 6αa (DAD 3-473) (F). Data are expressed as mean±SEM of n observations (n=2). Data are analyzed with non parametric Mann Withney analysis, *P<0.05, P<0.01 and *P<0.001.

Functional Effects of drugs on JOK Cells. The results are presented on FIGS. 5 to 8. FIG. 5 shows that the inventive compound 6αa significantly reduces JOK proliferation and affects cell cycle without significant reduction of cell survival. FIGS. 7 and 8 show that the inventive compound 6αa does not induce death of B cells and of HUVEC cells, respectively. FIGS. 7 and 8 show that the inventive compound 6αa, GSK-7975A and SKF-93365, at a concentration of 5 or 20 µM, do not induce apoptosis or necrosis of cells treated for 48 hours. However, the inventive compound 6αa used with 5 or 20 µM does significantly inhibit transendothelial migration through HUVEC of JOK cells whereas GSK-7975A does not.

Figure 9:
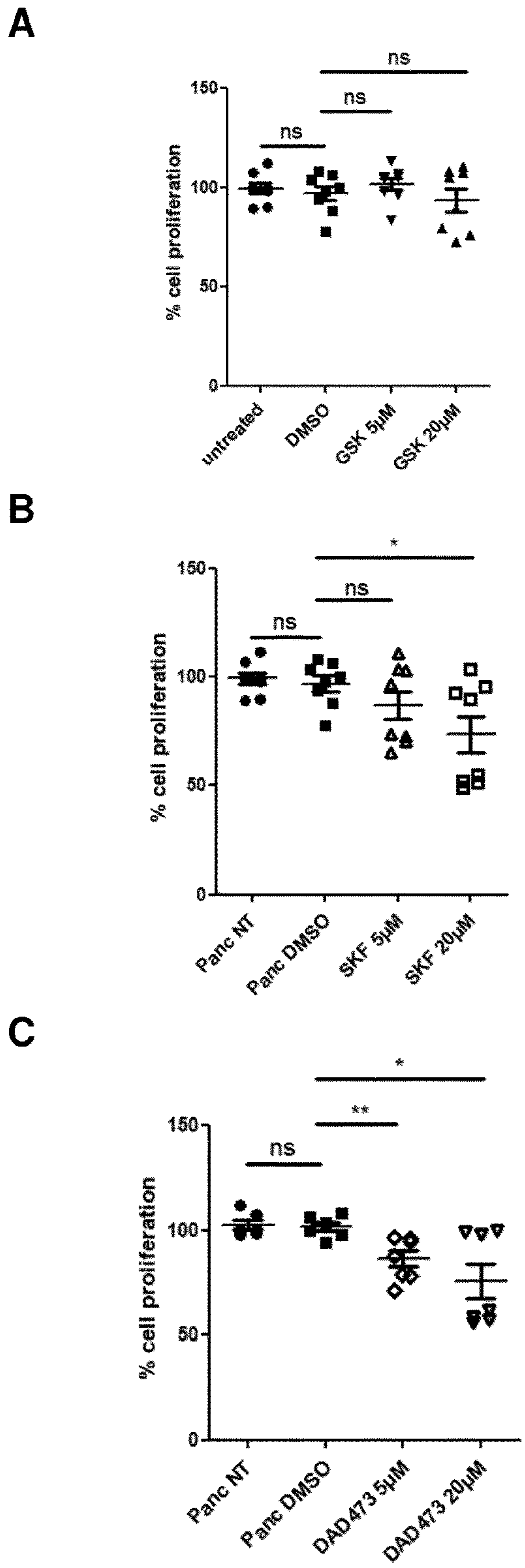
FIG. 9. Effects of 6αa, GSK-7975-A and SKF-93365 on Pancreatic Cancer Cells (PANC-1) Proliferation. In each experimental approach, PANC-1 cells were treated for 24 hours with (A) the SOCE inhibitor GSK-7975A, (B) the SOCE inhibitor SKF-93365, and (C) with the inventive compound 6αa (DAD 3-473) used at 2 different concentrations (5 μM and 20 μM). Evaluation of Panc-1-Wt cell proliferation was performed using an MTS assay. Histograms represent for each experimental condition the individual values and the mean±SEM of n observations. Data were normalized to the mean values obtained for untreated cells. Data are analyzed by non parametric Mann Withney analysis, *P<0.05, P<0.01 and *P<0.001.
Figure 10:
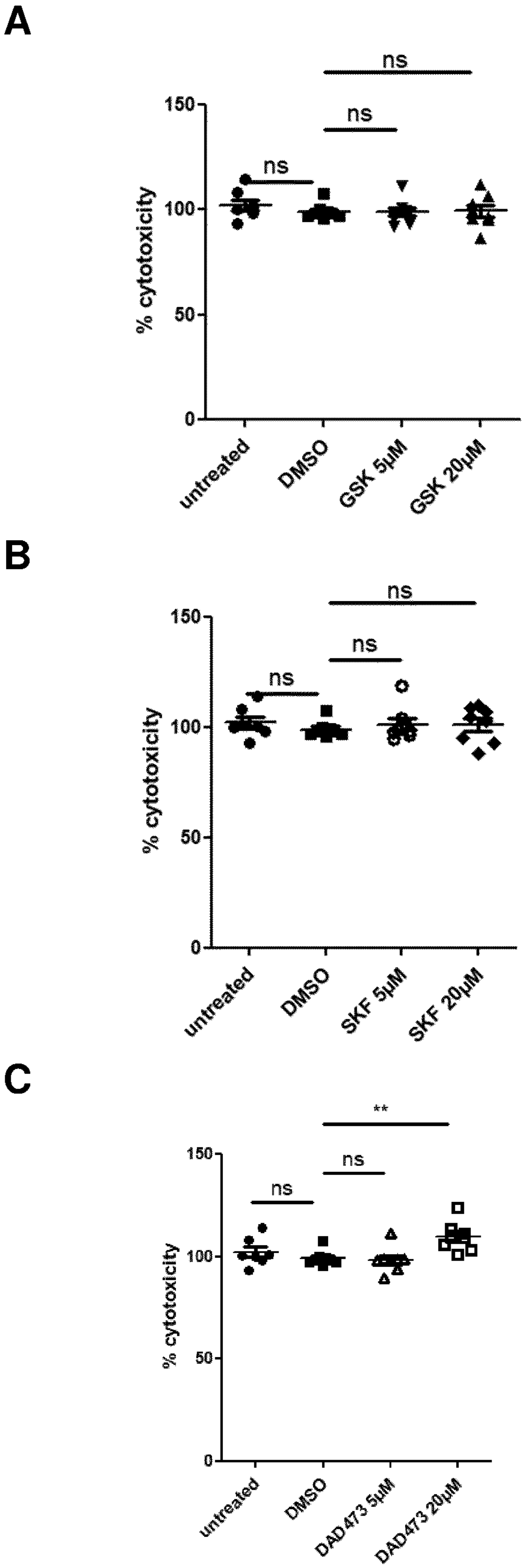
FIG. 10. In vitro Effects of 6αa, GSK-7975-A and SKF-93365 on Pancreatic Cancer Cells Cytotoxicity. In each experimental approach, PANC-1 cells were treated for 24 hours with (A) the SOCE inhibitor GSK-7975A, (B) the SOCE inhibitor SKF-93365, and (C) with the inventive compound 6αa (DAD 3-473) used at 2 different concentrations (5 μM and 20 μM). Evaluation of cytotoxic effects was evaluated with Cytotox Green assay. Histograms represent for each experimental condition the individual values and the mean±SEM of n observations. Data were normalized to the mean values obtained for untreated cells. Data are analyzed by non parametric Mann Withney analysis, *P<0.05, P<0.01 and *P<0.001.
Figure 11:
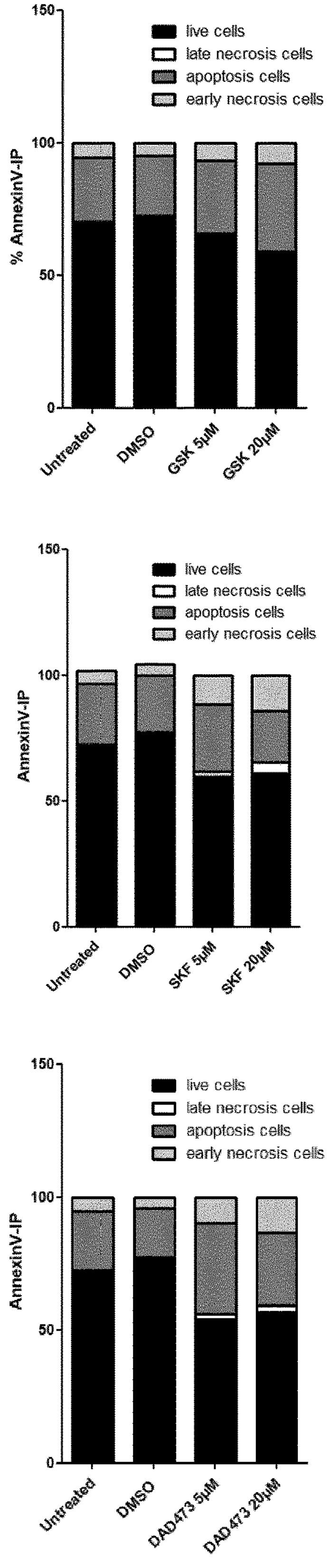
FIG. 11. In vitro Effects of 6αa, GSK-7975-A and SKF-93365 on Pancreatic Cancer Cells Death. PANC-1 cells were treated with (A) GSK-7975A, (B) SKF-93365 and (C) 6αa (DAD 3-473) at 2 different concentrations (5 and 20 μM) or with control DMSO for 24 hours. Cell death was analyzed by flow cytometry using Annexin/Propidium Iodide labeling. The percentages of living cells, necrotic cells and apoptotic cells submitted to SOCE inhibitor treatment were normalized to values obtained with the DMSO treatment condition. Data are expressed as mean±SEM of n observations (n=4).

Functional Effects of Drugs on Pancreatic Cancer Cells PANC-1. The results are presented on FIGS. 9 to 11. FIG. 9 shows that the inventive compound 6αa significantly reduces PANC-1 proliferation and reduces it to a greater extent than GSK-7975A and of SKF-93365. FIG. 10 shows that the inventive compound 6αa induces cytotoxicity in cancer PANC-1 cells whereas GSK-7975A and SKF-93365 display no cytotoxic effects against these cancer cells. FIG. 11 shows that the inventive compound 6αa induces PANC-1 cells by apoptosis even at a concentration of 5 µM.

IV Synthetic Pathway for the Preparation of Amido or Sulfamido Analogues of Inventive SOCE Inhibiter 6αa

Example 32

Synthesis of a Common Intermediate. The intermediate (compound 5 below), which is common to the preparation of an amido analogue of compound 6αa and to the preparation of a sulfamido analogue of compound 6αa, may be synthesized according to the following scheme.

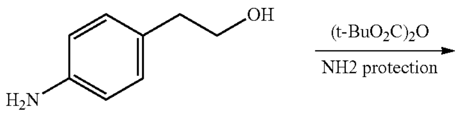

1: 4-aminophenylethanol

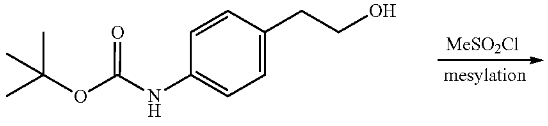

2: carbamate

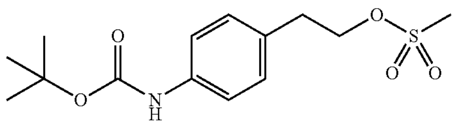

3: mesylated carbamate

-continued

3

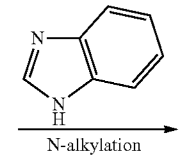

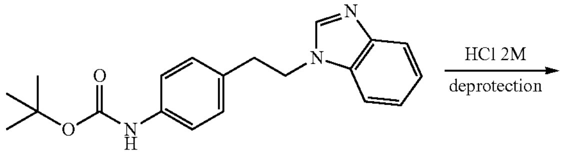

4: carbamate de benzimidazole

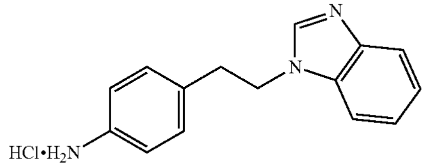

5: common intermediate

Synthesis of an Amido Analogue of Compound 6αa. An amido analogue of compound 6αa may be synthesized from the common intermediate 5 according to the following scheme.

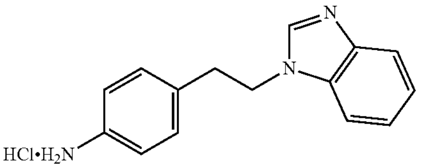

+

5: common intermediate

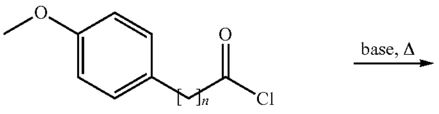

6: Acid chloride

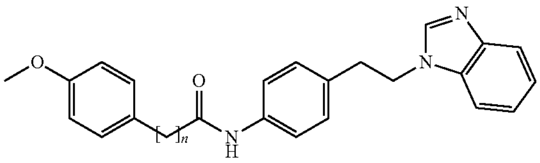

7: Amido analogue of 6αa

By reacting different acid chlorides with the common intermediate, different amino analogues may be obtained, as shown in the Table 8.

TABLE 8

Acid chlorides and corresponding amido analogues 7.

| Acid chlorides | Amido analogues |
| --- | --- |
| 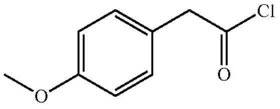 6a: 4-methoxyphenyl acetyl chloride | 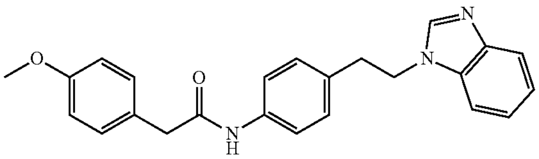 [SMILES: COc1ccc(CC(=O)Nc2ccc(CCn3cnc4ccccc43)cc2)cc1] 7a: n = 1 |
| 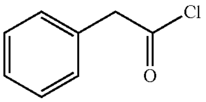 6b: 4-methoxyphenyl acetyl chloride | 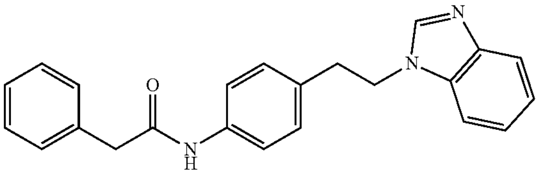 [SMILES: O=C(Cc1ccccc1)Nc1ccc(CCn2cnc3ccccc32)cc1] 7b: n = 1 |
| 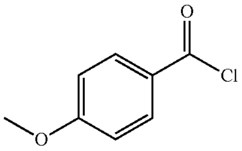 6c: 4-methoxybenzoyl chloride | 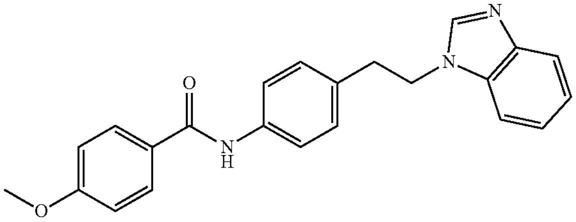 [SMILES: COc1ccc(C(=O)Nc2ccc(CCn3cnc4ccccc43)cc2)cc1] 7c: n = 0 |
| 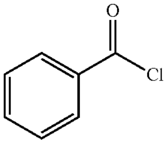 6d: benzoyl chloride | 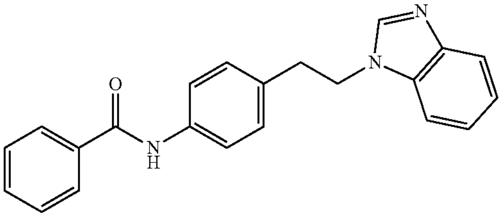 [SMILES: O=C(Nc1ccc(CCn2cnc3ccccc32)cc1)c1ccccc1] 7d: n = 0 |

Synthesis of a Sulfamido Analogue of Compound 6αa. A sulfamido analogue of compound 6αa may be synthesized from the common intermediate 5 according to the following scheme.

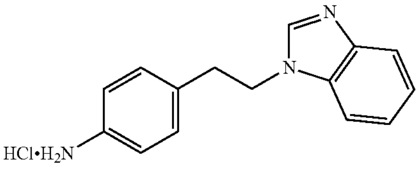

5: common intermediate

+

-continued

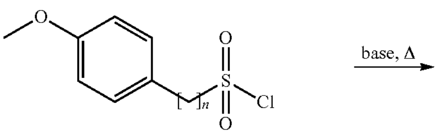

8: sulfonyl chloride

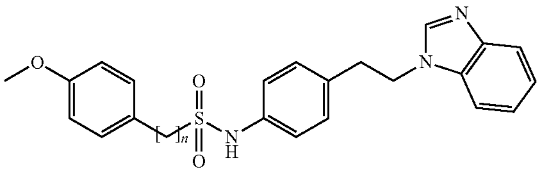

9: sulfamido analogue of 6αa

By reacting different sulfonyl chlorides with the common intermediates, different sulfamido analogues may be obtained, as shown in the Table 9.

TABLE 9

| Sulfonyl chlorides | Sulfamido analogues |
|---|---|
| Sulfonyls chlorides and corresponding sulfamido analogues 9. | |
| 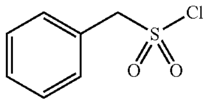 [SMILES: O=S(=O)(Cl)Cc1ccccc1] | 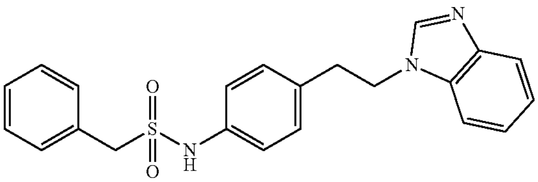 [SMILES: O=S(=O)(Cc1ccccc1)Nc1ccc(CCn2cnc3ccccc32)cc1] |
| 8a: α-toluenesulfonyl chloride | 9a: n = 1 |
| 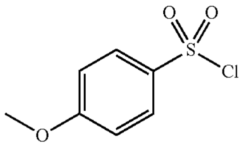 | 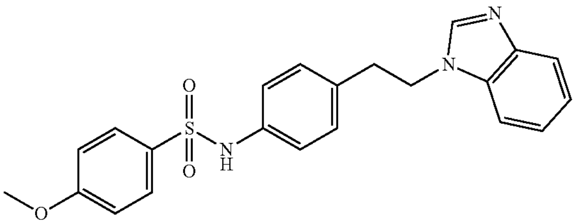 [SMILES: COc1ccc(S(=O)(=O)Nc2ccc(CCn3cnc4ccccc43)cc2)cc1] |
| 8b: 4-methoxybenzene sulfonyl chloride | 9b: n = 0 |
| 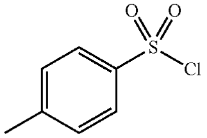 | 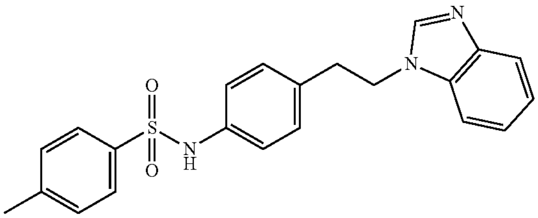 [SMILES: Cc1ccc(S(=O)(=O)Nc2ccc(CCn3cnc4ccccc43)cc2)cc1] |
| 8c: 4-methylbenzene sulfonyl chloride | 9c: n = 0 |
| 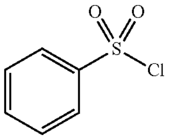 | 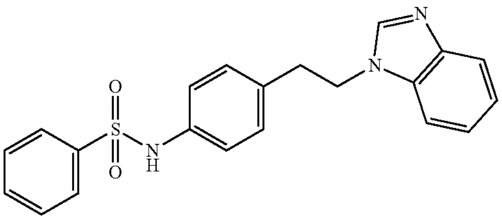 [SMILES: O=S(=O)(Nc1ccc(CCn2cnc3ccccc32)cc1)c1ccccc1] |
| 8d: benzene sulfonyl chloride | 9d: n = 0 |

What is claimed is:

1. An aromatic azole compound, (1) wherein said aromatic azole compound has chemical formula (I):

(I)

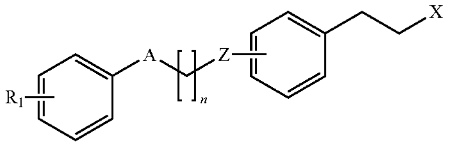

wherein:

$R_1$ is one, two, three, four or five substituents, wherein each of the substituents is independently selected from H, OH, a halogen, $NH_2$, an alkoxy, an aryloxy, $OCH_2OR$, wherein R is an alkyl group, and O-THP, wherein THP is tetrahydropyranyl;

A is $CH_2$ or O;

if A is $CH_2$, then n=0, 1 or 2, and if A is O, then n=2 or 3;

Z is O, NH, NHCO or CONH, NR, wherein R is an alkyl group, $NHSO_2$ or $SO_2NH$;

X is one of the following groups:

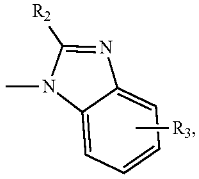
, and
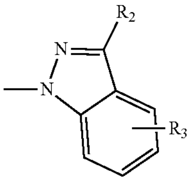

wherein:

$R_2$ is H, Cl, Br or $CF_3$; and $R_3$ is one, two, three or four substituents, wherein each of the substituents is independently selected from H, OH, $CF_3$, F, Cl, $NH_2$, COOH, and $CONH_2$;

or a pharmaceutically acceptable salt thereof, or (2) wherein said aromatic azole compound has the chemical formula of one of the following compounds:

6βu

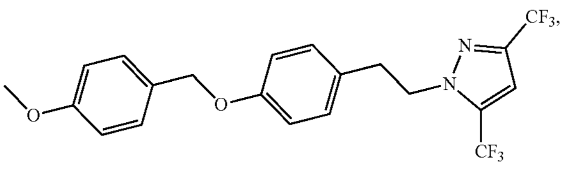

(DAD 2.334)

6βq

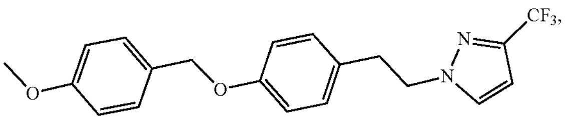

(DAD 2.333)

-continued

6βm

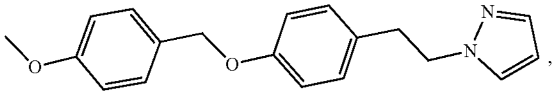

(DAD 2.306)

6βg

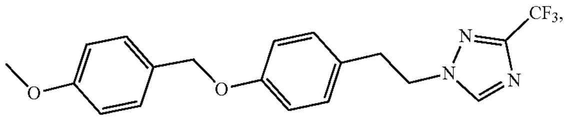

(DAD 3.472)

6βd

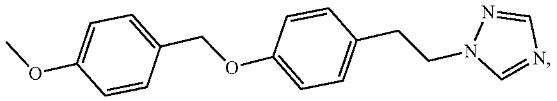

(DAD 3.468)

6βv

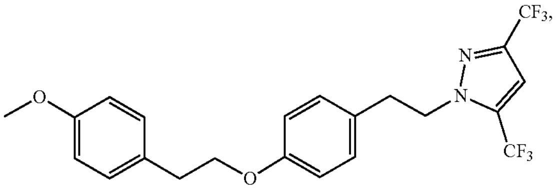

(DAD 2.266)

6βr

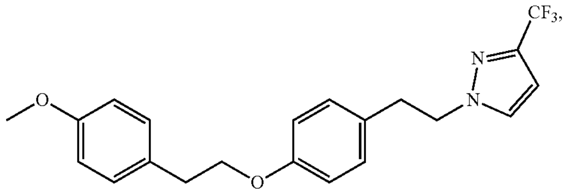

(DAD 3.362)

6βn

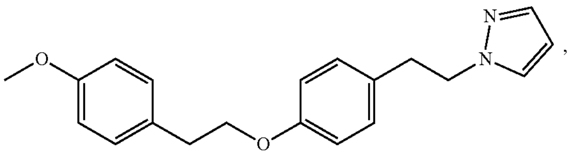

(DAD 2.307)

6βr

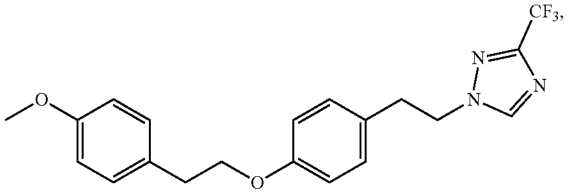

(DAD 3.473)

-continued

6βd

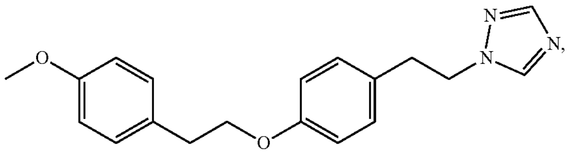

(DAD 3.469)

6βw

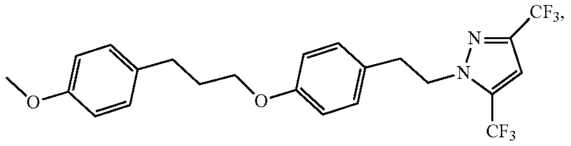

(DAD 2.335)

6βs

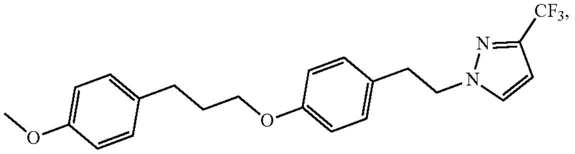

(DAD 2.276)

6βp

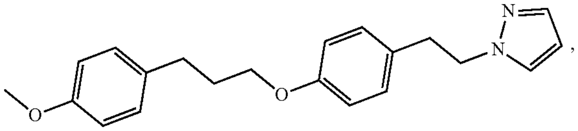

(DAD 2.308)

6βs

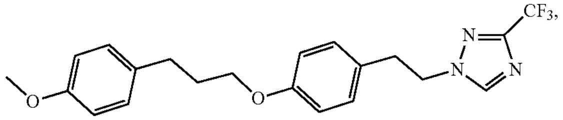

(DAD 3.474)

6βe

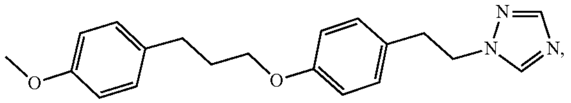

(DAD 3.470)

6βf

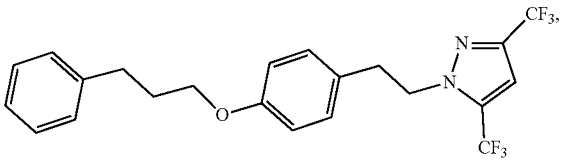

(DAD 2.300)

-continued

6βt

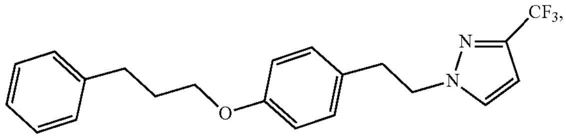

(DAD 2.300)

6βi

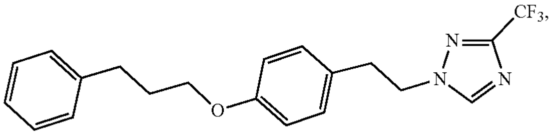

(DAD 3.475)

6βy

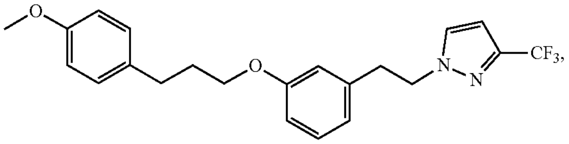

(DAD 3.531)

6βz

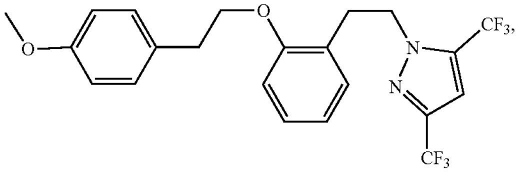

(DAD 3.536)

6βaa

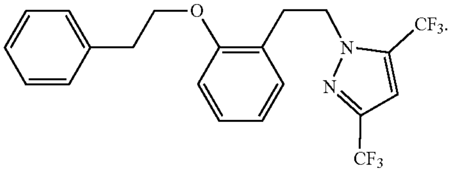

(DAD 3.535)

2. The aromatic azole compound according to claim 1, wherein the aromatic azole compound of chemical formula (I) has the chemical formula (II):

(II)

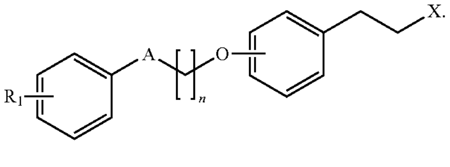

3. The aromatic azole compound according to claim 2, wherein the aromatic azole compound of chemical formula (I) has the chemical formula (III):

(III)
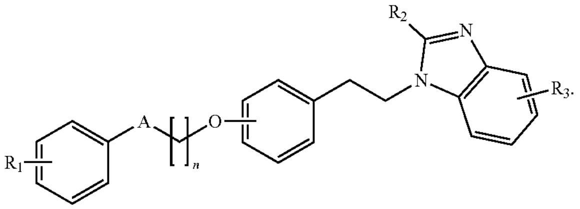
4. The aromatic azole compound according to claim 1, wherein the aromatic azole compound of chemical formula (I) has the chemical formula of one of the following compounds:
(DAD 4-546)
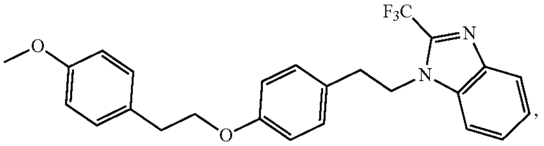
6αc
(VAL 1-76)
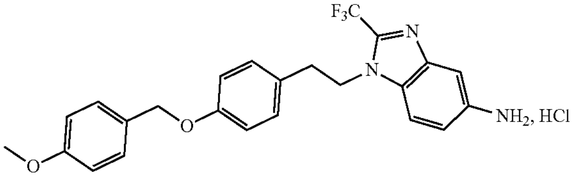
6αt
(VAL 1-77)
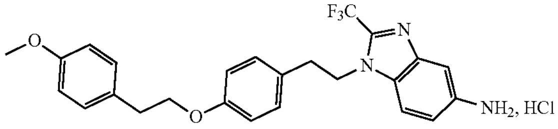
6αm
(VAL 1-75)
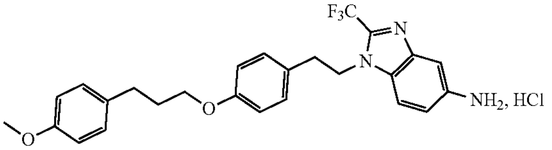
6αu
(VAL 1-64)
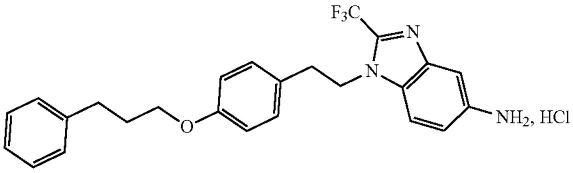
6αv
-continued
(DAD 4-548)
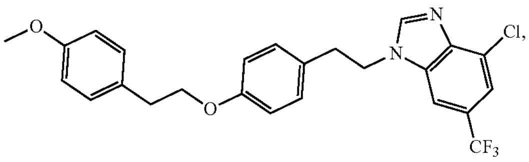
6αe
(DAD 4-547)
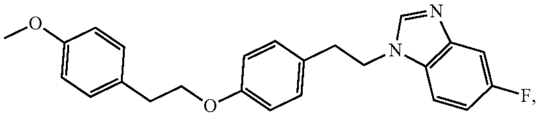
6αd
(DAD 4-551)
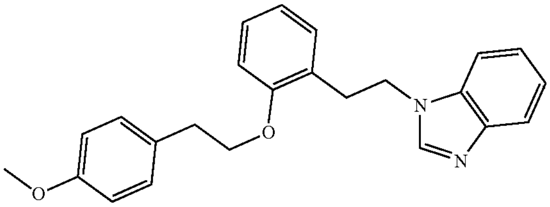
6αo
(DAD 4-552)
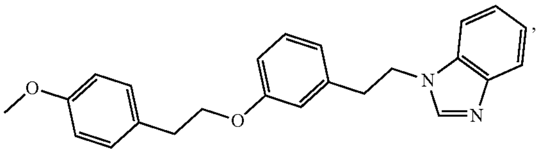
6αp
(DAD 4-553)
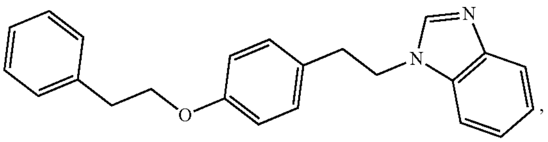
6αab
(DAD 4-566)
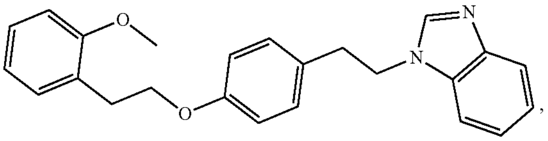
6αac
(DAD 4-567)
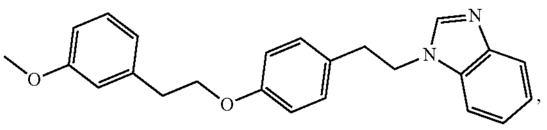
6αad -continued (DAD 4-568)

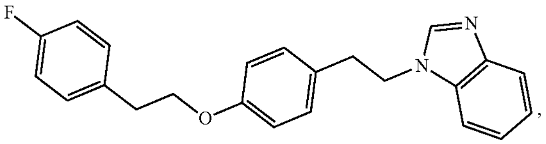

6αd (DAD 4-570)

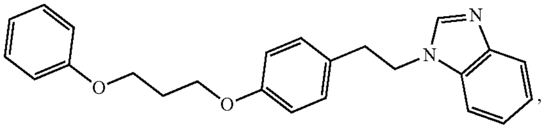

6αs (DAD 4-569)

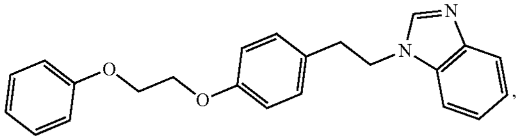

6αae (DAD 3-473)

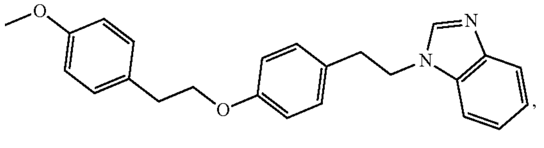

6αa (DAD 3-475)

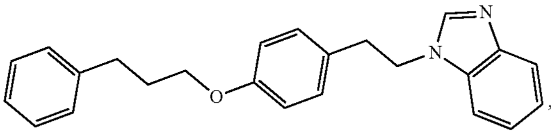

6αm (DAD 3-474)

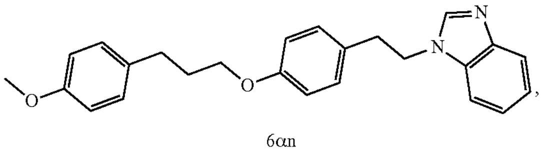

6αn (DAD 4-472)

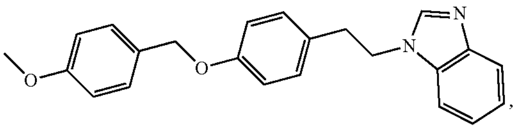

6αz (DAD 4-573)

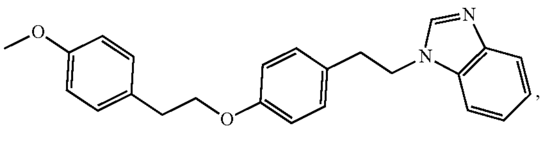

6αb

-continued (DAD 4-574)

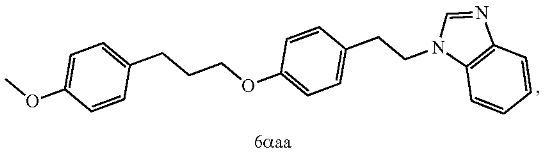

6αaa (DAD 4-575)

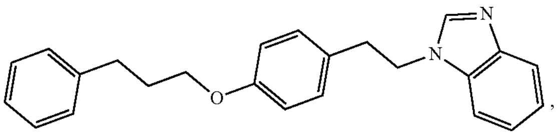

6αab (DAD 4.610)

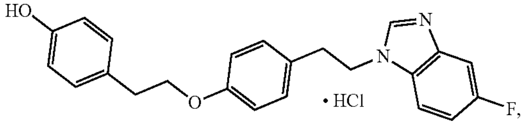

and (DAD 4.609)

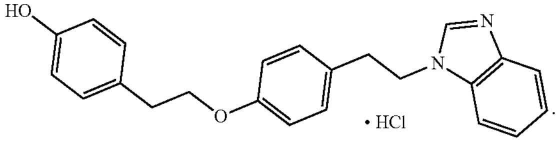

5. The aromatic azole compound according to claim 4, wherein the aromatic azole compound is selected from the group consisting of:

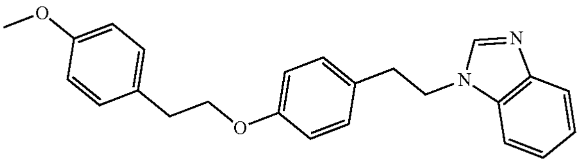

(6αa,DAD 3-473),

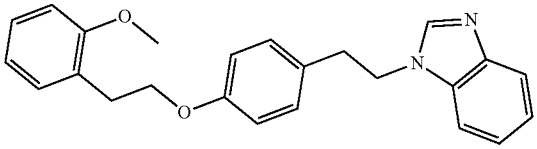

(6αac,DAD 4-566), and

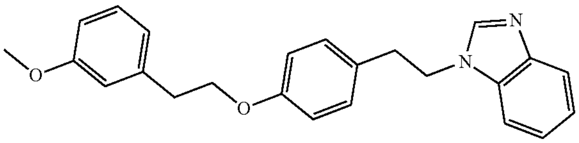

(6αad,DAD 4-567).

6. A pharmaceutical composition comprising an effective amount of at least one aromatic azole compound according to claim 1, and a pharmaceutically acceptable carrier or excipient.

7. A method for treating a disease associated with SOCE dysregulation or dysfunction in a subject, the method comprising a step of administering to the subject a therapeutically effective amount of an aromatic azole compound according to claim 1 or a pharmaceutical composition thereof, wherein the disease associated with SOCE dysregulation or dysfunction is selected from the group consisting of immunodeficiency diseases, allergies, cardiovascular diseases, cardiorespiratory diseases, vascular diseases, skeletal muscle diseases, and thromboses;

or wherein the disease associated with SOCE dysregulation or dysfunction is:

an inflammatory disease selected from the group consisting of inflammatory diseases of the musculoskeletal system, of the pulmonary system, of the cardiovascular system, of the gastrointestinal system, of the skin, of the neurologic system, of the central nervous system, of the hematologic system, and of the renal system;

or a cancer selected from the group consisting of breast, prostate, liver, lung, colon, cervical, ovarian, kidney, bladder, nasopharyngeal, epidermoid, esophageal, stomach, pancreatic, cervical, thyroid, neck cancer, skin, head and neck cancers, malignant tumors of the central and peripheral nervous system, hematopoietic tumors of the lymphoid lineage, and hematopoietic tumors of myeloid lineage.

8. The method according to claim 7, wherein the disease associated with SOCE dysregulation or dysfunction is selected from the group consisting of inflammatory bowel diseases, pancreatitis, rheumatoid arthritis, multiple sclerosis, asthma, psoriasis, liver cancers and pancreatic cancers.

* * * * *